United States Patent [19]

Olin et al.

[11] 3,979,202

[45] Sept. 7, 1976

[54] META-BIFUNCTIONAL BENZENES AND HERBICIDAL COMPOSITIONS

[75] Inventors: John F. Olin, Ballwin; Philip C. Hamm, Glendale, both of Mo.

[73] Assignee: Monsanto Company, St. Louis, Mo.

[22] Filed: Feb. 6, 1975

[21] Appl. No.: 547,539

Related U.S. Application Data

[60] Division of Ser. No. 40,742, May 26, 1970, Pat. No. 3,865,867, which is a continuation-in-part of Ser. No. 647,202, June 19, 1967, abandoned.

[52] U.S. Cl. ............................... 71/98; 260/455 A; 260/471 C
[51] Int. Cl.² ...................................... A01N 9/12
[58] Field of Search ............... 260/455 A, 471 C; 71/111, 98

[56] References Cited
UNITED STATES PATENTS

| | | | |
|---|---|---|---|
| 3,036,112 | 5/1962 | Lynn | 71/111 |
| 3,252,986 | 5/1966 | Gadekar | 260/471 C |
| 3,404,975 | 10/1968 | Wilson | 260/471 C |
| 3,535,101 | 10/1970 | Boroschewski et al. | 71/111 |
| 3,642,891 | 2/1972 | Teach | 71/111 |
| 3,723,474 | 3/1973 | Teach et al. | 260/455 A |
| 3,778,473 | 12/1973 | Kornis | 71/111 |
| 3,792,994 | 2/1974 | Baker et al. | 260/471 C |
| 3,806,537 | 4/1974 | Dorschner et al. | 260/455 R |
| 3,829,464 | 8/1974 | Kornis et al. | 260/471 C |
| 3,836,570 | 9/1974 | Szabo | 260/471 C |
| 3,865,867 | 2/1975 | Olin et al. | 71/111 |
| 3,867,426 | 2/1975 | Olin et al. | 71/111 |
| 3,879,441 | 4/1975 | Boroschewski et al. | 71/111 |
| 3,897,493 | 7/1975 | Teach | 71/111 |

OTHER PUBLICATIONS
J. Org. Chem., pp. 346–353, (1942).

*Primary Examiner*—Lewis Gotts
*Assistant Examiner*—D. R. Phillips
*Attorney, Agent, or Firm*—Richard H. Shear

[57] ABSTRACT

Meta-bifunctional of the general formula

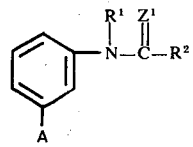

wherein A is selected from the groups

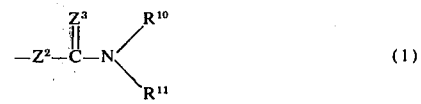 (1)

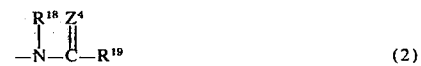

(2)

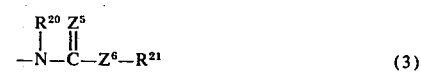

(3)

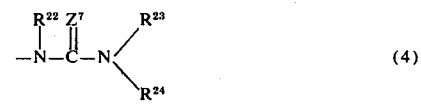

(4)

These compounds possess herbicidal activity.

6 Claims, No Drawings

META-BIFUNCTIONAL BENZENES AND HERBICIDAL COMPOSITIONS

This is a division of application Ser. No. 40,742 filed May 26, 1970, now U.S. Pat. No. 3,865,867, which in turn is a continuation-in-part of application Ser. No. 647,202, filed June 19, 1967 now abandoned.

This invention relates to novel meta-bifunctional substituted benzenes. This invention further relates to herbicidal compositions and methods of herbicidal use utilizing the novel meta-bifunctional substituted benzenes of this invention.

The novel meta-bifunctional substituted benzenes of this invention are of the formula

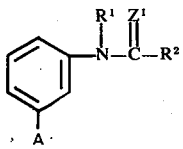

wherein
$Z^1$ is selected from the group consisting of oxygen and sulfur;
$R^1$ is selected from the group consisting of
I. hydrogen,
II. $R^3 — [B]_n$ - wherein B is selected from the group consisting of carbonyl and oxygen; $R^3$ is selected from the group consisting of alkyl having a maximum of 12 carbon atoms, alkenyl having a maximum of 7 carbon atoms and alkynyl having at least 3 and a maximum of 6 carbon atoms; and $n$ is an integer from 0 to 1; and
III. $R^6O — [R^5O]_m — R^4$ - wherein $R^4$ is alkylene of not more than 4 carbon atoms; $R^5$ is alkylene of not more than 4 carbon atoms; $R^6$ is selected from the group consisting of alkyl and alkenyl of not more than 6 carbon atoms and $m$ is an integer from 0 to 1;
$R^2$ is selected from the group consisting of
I. hydrogen,
II. hydrocarbyl selected from the group consisting of alkyl having a maximum of 12 carbon atoms, alkenyl having a maximum of 8 carbon atoms, alkynyl having a maximum of 6 carbon atoms and haloalkyl having a maximum of 6 carbon atoms and a maximum of 3 halogen atoms;
III. $R^6O — [R^5O]_m — R^4$ - wherein $R^4$, $R^5$, $R^6$ and $m$ are as previously defined,
IV. cycloalkyl and alkylcycloalkyl having 3 to 7 ring carbon atoms and a maximum of 4 chain carbon atoms;
V. phenyl and substituted phenyl having a maximum of two substituents said substituent being selected from the group consisting of halogen, alkyl having a maximum of four carbon atoms and — COOH; and
VI. aralkyl of the formula

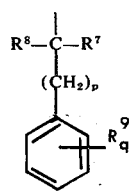

wherein $R^7$ is selected from the group consisting of hydrogen, alkyl having a maximum of 4 carbon atoms, alkenyl having a maximum of 3 carbon atoms and haloalkyl having a maximum of 4 carbon atoms and a maximum of three halogen atoms; $R^8$ is selected from the group consisting of hydrogen, alkyl having a maximum of 4 carbon atoms and haloalkyl having a maximum of 4 carbon atoms and a maximum of 3 halogen atoms; $R^9$ is independently selected from the group consisting of alkyl having a maximum of 4 carbon atoms, alkoxy having a maximum of 2 carbon atoms, — COOH, and halogen; $p$ is one of the integers zero to two; and $q$ is one of the integers zero to two; and A is selected from the group consisting of

 (1)

wherein
$Z^2$ and $Z^3$ are each independently selected from the group consisting of oxygen and sulfur;
$R^{10}$ is selected from the group consisting of alkyl having a maximum of 15 carbon atoms, alkenyl having a maximum of 12 carbon atoms, chloroalkyl having a maximum of 15 carbon atoms and a maximum of 3 halogen atoms, chloroalkenyl having a maximum of 12 carbon atoms and a maximum of 3 halogen atoms, alkoxyalkyl having a maximum of 12 carbon atoms, cycloalkyl having 3 to 7 ring carbon atoms and a maximum of 4 chain carbon atoms, phenyl, substituted phenyl having a maximum of two substituents, said substituents being selected from the group consisting of halogen, nitro and alkyl having a maximum of 4 carbon atoms, — $CH_2CH_2$ — O — phenyl, — $CH_2CH_2$ — O — naphthyl, — $CH_2$ — CH = CH — phenyl, the group

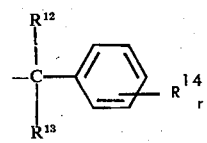

wherein $R^{12}$ and $R^{13}$ are each independently selected from the group consisting of hydrogen, alkyl having a maximum of 4 carbon atoms, alkenyl having a maximum of 3 carbon atoms chloroalkyl having a maximum of 3 carbon atoms and a maximum of 3 halogen atoms, chloroalkenyl having a maximum of 3 carbon atoms and 3 halogen atoms, provided that only one of $R^{12}$ and $R^{13}$ can be alkenyl or chloroalkenyl; $R^{14}$ is selected from the group consisting of halogen, alkyl having a maximum of 4 carbon atoms, nitro, alkoxy having a maximum of 3 carbon atoms, and $r$ is one of the integers zero to two; the group

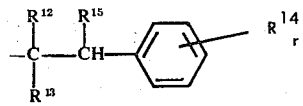

wherein $R^{15}$ is selected from the group consisting of alkyl and alkenyl each having a maximum of 4 carbon atoms, provided that $R^{15}$ is other than alkenyl where either $R^{12}$ or $R^{13}$ is alkenyl, and $R^{12}$, $R^{13}$, $R^{14}$ and $r$ are as previously defined; and the group

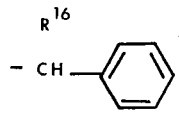

wherein $R^{16}$ is selected from the group consisting of phenyl and naphthyl; $R^{11}$ is selected from the group consisting of hydrogen, alkyl having a maximum of 6 carbon atoms, cycloalkyl having 5 to 7 carbon atoms, alkenyl having a maximum of 4 carbon atoms and chloroalkyl having a maximum of 3 carbon atoms and a maximum of 3 halogen atoms, chloroalkenyl having a maximum of 4 carbon atoms and a maximum of 3 halogen atoms; $R^{10}$ and $R^{11}$ can together with the nitrogen atom form a group selected from the group consisting of

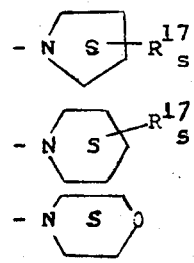

wherein $R^{17}$ is alkyl having a maximum of 3 carbon atoms and $S$ is one of the integers zero to two;

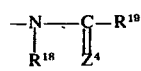  (2)

wherein $Z^4$ is selected from the group consisting of oxygen and sulfur;

$R^{18}$ is selected from the group consisting of
I. hydrogen,
II. $R^3 - [B]_n$ - wherein B is selected from the group consisting of carbonyl and oxygen, $R^3$ is selected from the group consisting of alkyl having a maximum of 12 carbon atoms, alkenyl having a maximum of 7 carbon atoms and alkynyl having at least 3 and a maximum of 6 carbon atoms; and $n$ is an integer from 0 to 1; and
III. $R^6O - [R^5O]_m - R^4$ - wherein $R^4$ is alkylene of not more than 8 carbon atoms; $R^5$ is alkylene of not more than 4 carbon atoms; $R^6$ is selected for the group consisting of alkyl and alkenyl of not more than 6 carbon atoms; and $m$ is an integer from 0 to 1; and $R^{19}$ is selected from the group consisting of
I. hydrogen,
II. hydrocarbyl selected from the group consisting of alkyl having a maximum of 15 carbon atoms, alkenyl having a maximum of 8 carbon atoms, alkynyl having at least 3 and a maximum of 6 carbon atoms and haloalkyl having a maximum of 6 carbon atoms and a maximum of 3 halogen atoms;
III. $R^6O - [R^5O]_m - R^4$ wherein $R^4$, $R^5$, $R^6$ and $m$ are as previously defined,
IV. cycloalkyl and alkylcycloalkyl having 3 to 7 ring carbon atoms and a maximum of 4 chain carbon atoms;
V. phenyl and substituted phenyl having a maximum of two substituents said substituent being selected from the group consisting of halogen, alkyl having a maximum of 4 carbon atoms and — COOH; and
VI. aralkyl of the formula

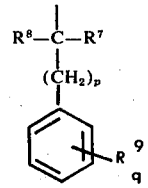

wherein $R^7$ is selected from the group consisting of hydrogen, alkyl having a maximum of 4 carbon atoms, alkenyl having a maximum of 3 carbon atoms and haloalkyl having a maximum of 4 carbon atoms and a maximum of three halogen atoms, $R^8$ is selected from the group consisting of hydrogen, alkyl having a maximum of 4 carbon atoms and haloalkyl having a maximum of 4 carbon atoms and a maximum of 3 halogen atoms; $R^9$ is independently selected from the group consisting of alkyl having a maximum of 4 carbon atoms, alkoxy having a maximum of 2 carbon atoms, — COOH, and halogen; $p$ is one of the integers 0 to 2 and $q$ is one of the integers 0 to 2;

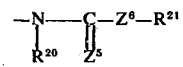  (3)

wherein $Z^5$ and $Z^6$ are each independently selected from the group consisting of oxygen and sulfur;

$R^{20}$ is selected from the group consisting of hydrogen, alkyl having a maximum of 6 carbon atoms and alkenyl having a maximum of 6 carbon atoms; and $R^{21}$ is selected from the group consisting of alkyl having a maximum of 8 carbon atoms, alkenyl having a maximum of 6 carbon atoms, cycyloalkyl having from 3 to 7 ring carbon atoms; cyclohexenyl, phenyl, substituted phenyl having a maximum of two substituents said substituents being selected from the group consisting of halogen, nitro and alkyl having a maximum of 4 carbon atoms, the group

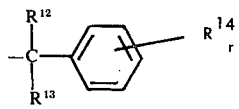

and the group

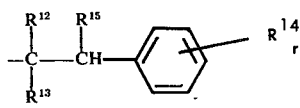

wherein $R^{12}$, $R^{13}$, $R^{14}$, $R^{15}$ and $r$ are as previously defined; and

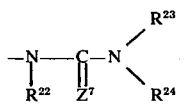 (4)

wherein $Z^7$ is selected from the group consisting of oxygen and sulfur; $R^{22}$ is selected from the group consisting of hydrogen, alkyl having a maximum of 8 carbon atoms and alkenyl having a maximum of 6 carbon atoms; $R^{23}$ is selected from the group consisting of alkyl having a maximum of 12 carbon atoms, alkenyl having a maximum of 7 carbon atoms, alkoxy having a maximum of 6 carbon atoms, chloroalkyl having a maximum of 6 carbon atoms and a maximum of 3 halogen atoms, chloroalkenyl having a maximum of 6 carbon atoms and a maximum of 3 halogen atoms, phenyl, substituted phenyl having a maximum of two substituents said substituents being selected from the group consisting of halogen, nitro and alkyl having a maximum of 4 carbon atoms, the group

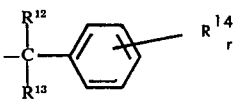

, and the group

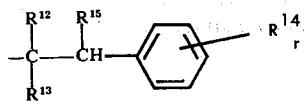

wherein $R^{12}$, $R^{13}$, $R^{14}$, $R^{15}$ and $r$ are as previously defined; $R^{24}$ is selected from the group consisting of hydrogen, alkyl having a maximum of 12 carbon atoms and alkenyl having a maximum of 8 carbon atoms; $R^{23}$ and $R^{24}$ can with the nitrogen form the group selected from the group consisting of

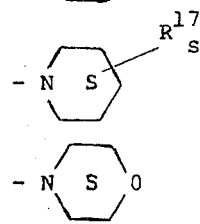 and

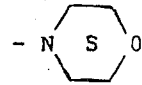

wherein $R^{17}$ and $s$ are as previously defined.

As a first preferred embodiment of this invention are the compounds in which $R^1$ is selected from the group consisting of hydrogen, alkoxy having a maximum of 6 carbon atoms, alkyl having a maximum of 6 carbon atoms and alkenyl having a maximum of 6 carbon atoms; $Z^1$, $R^2$ and A are as previously defined.

Another preferred embodiment of this invention are the compounds of the formula

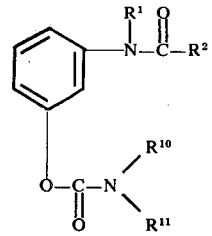

wherein $R^1$ is selected from the group consisting of hydrogen and alkyl having a maximum of six carbon atoms; $R^2$ is selected from the group consisting of hydrogen, alkyl having a maximum of 12 carbon atoms, alkenyl having a maximum of 8 carbon atoms haloalkyl having a maximum of 6 carbon atoms and a maximum of 3 halogen atoms; cycloalkyl having 3 to 7 ring carbon atoms, substituted cycloalkyl having 3 to 7 ring carbon atoms and a maximum of 4 chain carbon atoms, phenyl, substituted phenyl having a maximum of two substituents said substituent being selected from the group consisting of halogen and alkyl having a maximum of 4 carbon atoms, and aralkyl of the formula

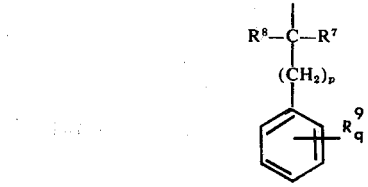

wherein $R^7$ is selected from the group consisting of hydrogen, alkyl having a maximum of 4 carbon atoms, alkenyl having a maximum of 3 carbon atoms and haloalkyl having a maximum of 4 carbon atoms and a maximum of 3 halogen atoms; $R^8$ is selected from the group consisting of hydrogen, and alkyl having a maximum of 4 carbon atoms; $R^9$ is independently selected from the group consisting of alkyl having a maximum of 4 carbon atoms, alkoxy having a maximum of 2 carbon atoms and halogen; $p$ is one of the integers 0 to 1, and $q$ is one of the integers 0 to 2; $R^{10}$ is selected from the group consisting of alkyl having 8 to 15 carbon atoms, alkenyl having 8 to 12 carbon atoms, chloroalkyl having 4 to 12 carbon atoms and a maximum of 3 halogen atoms, chloroalkenyl having a maximum of 12 carbon atoms and a maximum of 3 halogen atoms, alkoxyalkyl having a maximum of a total of 12 carbon atoms, cycloalkyl having 3 to 7 ring carbon atoms, substituted having 3 to 7 ring carbon atoms and a maximum of 4 chain carbon atoms, —CH$_2$CH$_2$—O—phenyl, —CH$_2$CH$_2$—O—naphthyl, —CH$_2$CH=CH—phenyl, the group

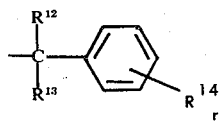

wherein $R^{12}$ and $R^{13}$ are each independently selected from the group consisting of hydrogen, alkyl having a maximum of 4 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, provided that only one of $R^{12}$ and $R^{13}$ can be alkenyl or chloroalkenyl; $R^{14}$ is selected from the group consisting of halogen, alkyl having a maximum of 4 carbon atoms, nitro, alkoxy having a maximum of 3 carbon atoms; and $r$ is one of the integers 0 to 2, the group

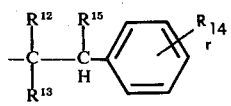

wherein $R^{15}$ is selected from the group consisting of alkyl and alkenyl each having a maximum of 4 carbon atoms, provided that $R^{15}$ is other than alkenyl when either $R^{12}$ or $R^{13}$ is alkenyl or chloroalkenyl, and $R^{12}$, $R^{13}$, $R^{14}$ and $r$ are as previously defined, and the group

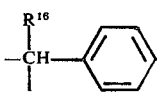

wherein $R^{16}$ is selected from the group consisting of phenyl and naphthyl; $R^{11}$ is selected from the group consisting of hydrogen, alkyl having a maximum of 6 carbon atoms, alkenyl having a maximum of 4 carbon atoms and chloroalkyl having a maximum of 3 carbon atoms and a maximum of 3 halogen atoms, chloroalkenyl having a maximum of 4 carbon atoms and a maximum of 3 halogen atoms; $R^{10}$ and $R^{11}$ can together with the nitrogen atom form a group selected from the group consisting of

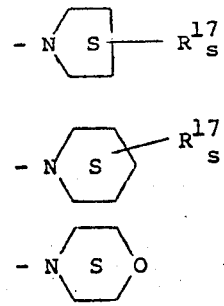

wherein $R^{17}$ is alkyl having a maximum of 3 carbon atoms and $s$ is one of the integers 0 to 2.

A still more preferred embodiment are the compounds of the formula

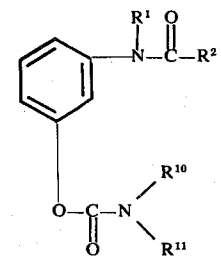

wherein $R^1$ is selected from the group consisting of hydrogen and alkyl having a maximum of three carbon atoms; $R^2$ is selected from the group consisting of alkyl having at least 8 and a maximum of 15 carbon atoms, alkenyl having at least 7 and a maximum of 10 carbon atoms, haloalkyl having at least 3 and a maximum of 6 carbon atoms and a maximum of 3 halogen atoms, phenyl, substituted phenyl having a maximum of two substituents said substituent being selected from the group consisting of halogen and alkyl having a maximum of four carbon atoms and aralkyl of the formula

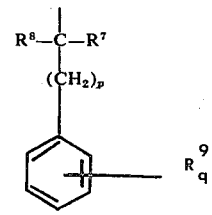

wherein $R^7$ is selected from the group consisting of hydrogen, alkyl having a maximum of 4 carbon atoms, alkenyl having a maximum of 3 carbon atoms and haloalkyl having a maximum of 4 carbon atoms and a maximum of 3 halogen atoms; $R^8$ is selected from the group consisting of hydrogen and alkyl having a maximum of 4 carbon atoms; $R^9$ is independently selected from the group consisting of alkyl having a maximum of 4 carbon atoms, alkoxy having a maximum of 2 carbon atoms and halogen; $p$ is one of the integers 0 to 1; and $q$ is one of the integers 0 to 2; $R^{10}$ is selected from the group consisting of alkyl having 8 to 15 carbon atoms, alkenyl having 8 to 12 carbon atoms, chloroalkyl having 4 to 12 carbon atoms and a maximum of 3 halogen atoms, chloroalkenyl having a maximum of 12 carbon atoms and a maximum of 3 halogen atoms, alkoxyalkyl having a maximum of a total of 12 carbon atoms, cycloalkyl having 3 to 7 ring carbon atoms, substituted having 3 to 7 ring carbon atoms and a maximum of 4 chain carbon atoms, —CH$_2$CH$_2$—O—phenyl, —CH$_2$CH$_2$—O—naphthyl, —CH$_2$CH=CH—phenyl, the group

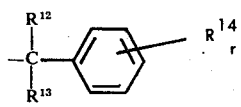

wherein R$^{12}$ and R$^{13}$ are each independently selected from the group consisting of hydrogen, alkyl having a maximum of 4 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, provided that only one of R$^{12}$ and R$^{13}$ can be alkenyl or chloroalkenyl; R$^{14}$ is selected from the group consisting of halogen, alkyl having a maximum of 4 carbon atoms, nitro, alkoxy having a maximum of 3 carbon atoms; and r is one of the integers zero to two, the group

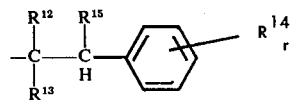

wherein R$^{15}$ is selected from the group consisting of alkyl and alkenyl each having a maximum of 4 carbon atoms, provided that R$^{15}$ is other than alkenyl when either R$^{12}$ or R$^{13}$ is alkenyl or chloroalkenyl, and R$^{12}$, R$^{13}$, R$^{14}$ and r are as previously defined, and the group

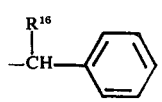

wherein R$^{16}$ is selected from the group consisting of phenyl and naphthyl; R$^{11}$ is selected from the group consisting of hydrogen, alkyl having a maximum of 6 carbon atoms, alkenyl having a maximum of 6 carbon atoms, alkenyl having a maximum of 4 carbon atoms and chloroalkyl having a maximum of 3 carbon atoms and a maximum of 3 halogen atoms; R$^{10}$ and R$^{11}$ can together with the nitrogen atom form a group selected from the group consisting of

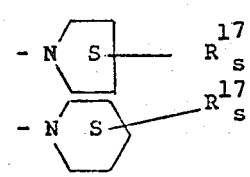

wherein R$^{17}$ is alkyl having a maximum of 3 carbon atoms and $s$ is one of the integers zero to two.

A further embodiment are the compounds of the formula

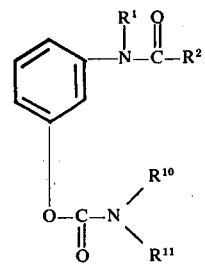

wherein R' is selected from the group consisting of hydrogen and alkyl having a maximum of 3 carbon atoms; R$^2$ is selected from the group consisting of alkyl having at least 8 and a maximum of 15 carbon atoms, alkenyl having at least 8 and a maximum of 10 carbon atoms, haloalkyl having at least 3 carbon atoms and a maximum of 6 carbon atoms and a maximum of 3 halogen atoms, cycloalkyl having at least 3 and a maximum of 6 carbon atoms, phenyl, substituted phenyl having a maximum of two substituents said substituent being independently selected from the group consisting of halogen and alkyl having a maximum of 4 carbon atoms, and aralkyl of the formula

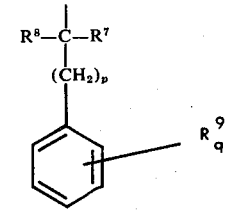

wherein R$^7$ is selected from the group consisting of hydrogen, alkyl having a maximum of 4 carbon atoms, alkenyl having a maximum of 3 carbon atoms and haloalkyl having a maximum of 4 carbon atoms and a maximum of 3 halogen atoms; R$^8$ is selected from the group consisting of hydrogen and alkyl having a maximum of 4 carbon atoms; R$^9$ is independently selected from the group consisting of alkyl having a maximum of 4 carbon atoms, alkoxy having a maximum of 2 carbon atoms and halogen; $p$ is one of the integers 0 to 1; and $q$ is one of the integers 0 to 2; R$^{10}$ is selected from the group consisting of —CH$_2$CH$_2$O—phenyl, —CH$_2$CH$_2$O—naphthyl, —CH$_2$CH=CH—phenyl, the group

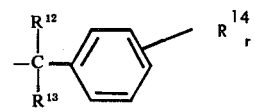

wherein $R^{12}$ and $R^{13}$ are each independently selected from the group consisting of hydrogen, alkyl having a maximum of 4 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, provided that only one of $R^{12}$ and $R^{13}$ is alkenyl or chloroalkenyl; $R^{14}$ is selected from the group consisting of halogen, alkyl having a maximum of 4 carbon atoms, nitro, alkoxy having a maximum of 3 carbon atoms, and $r$ is one of the integers 0 to 2, the group

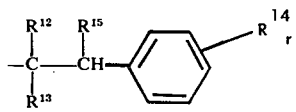

wherein $R^{15}$ is selected from the group consisting of alkyl and alkenyl each having a maximum of 4 carbon atoms, provided that $R^{15}$ is other than alkenyl when either $R^{12}$ or $R^{13}$ is alkenyl, and $R^{12}$, $R^{13}$, $R^{14}$ and $r$ are as previously defined, and the group

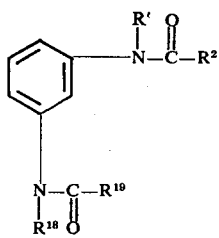

wherein $R^{16}$ is selected from the group consisting of phenyl and naphthyl.

Another preferred embodiment of this invention are the compounds of the formula

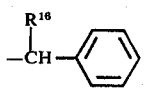

wherein $R'$ and $R^{18}$ are independently selected from the group consisting of hydrogen and alkyl having a maximum of 6 carbon atoms; and $R^2$ and $R^{19}$ are independently selected from the group consisting of hydrogen, alkyl having a maximum of 15 carbon atoms, alkenyl having a maximum of 10 carbon atoms, haloalkyl having a maximum of 6 carbon atoms and a maximum of 4 halogen atoms; cycloalkyl having 3 to 7 ring carbon atoms, substituted cycloalkyl having 3 to 7 ring carbon atoms and a maximum of 4 carbon atoms, phenyl, substituted phenyl having a maximum of two substituents said substituents being independently selected from the group consisting of halogen and alkyl having a maximum of four carbon atoms; —CH$_2$CH$_2$O—phenyl, —CH$_2$CH$_2$O—naphthyl, —CH$_2$CH=CH—phenyl, the group

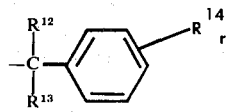

wherein $R^{12}$ and $R^{13}$ are each independently selected from the group consisting of hydrogen, alkyl having a maximum of 4 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, provided that only one of $R^{12}$ and $R^{13}$ can be alkenyl or chloroalkenyl; $R^{14}$ is independently selected from the group consisting of halogen, alkyl having a maximum of 4 carbon atoms, nitro, alkoxy having a maximum of 3 carbon atoms, and $r$ is one of the integers 0 to 2, the group

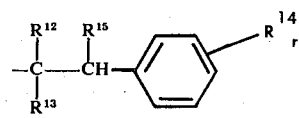

wherein $R^{15}$ is selected from the group consisting of alkyl and alkenyl each having a maximum of 4 carbon atoms, provided that $R^{15}$ is other than alkenyl when either $R^{12}$ or $R^{13}$ is alkenyl or chloroalkenyl, and $R^{12}$, $R^{13}$, $R^{14}$ and $r$ are as previously defined, and the group

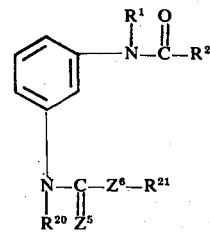

wherein $R^{16}$ is selected from the group consisting of phenyl and naphthyl.

Another preferred embodiment of this invention are the compounds of the formula

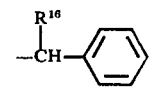

wherein $R^1$ is selected from the group consisting of hydrogen, alkoxy having a maximum of 6 carbon atoms, alkyl having a maximum of 6 carbon atoms and alkenyl having a maximum of 6 carbon atoms; $R^2$ is selected from the group consisting of alkyl having a maximum of 12 carbon atoms, alkenyl having a maximum of 10 carbon atoms, haloalkyl having a maximum of 6 carbon atoms and a maximum of four carbon atoms, cycloalkyl having 3 to 7 ring carbon atoms and a maximum of 4 chain carbon atoms, phenyl, substituted phenyl having a maximum of two substituents, said substituent being selected from the group consisting of halogen, alkyl having a maximum of four carbon atoms and —COOH, and the group

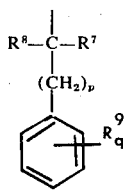

wherein $R^7$ is selected from the group consisting of hydrogen, alkyl having a maximum of 4 carbon atoms, alkenyl having a maximum of 3 carbon atoms, and haloalkyl having a maximum of 4 carbon atoms and a maximum of three halogen atoms; $R^8$ is selected from the group consisting of hydrogen, alkyl having a maximum of 4 carbon atoms and haloalkyl having a maximum of 4 carbon atoms and a maximum of 3 halogen atoms; $R^9$ is independently selected from the group consisting of alkyl having a maximum of 4 carbon atoms, alkoxy having a maximum of 2 carbon atoms, —COOH and halogen; $p$ is one of the integers 0 to 2; $R^{20}$, $R^{21}$, $Z^5$ and $Z^6$ are as previously defined.

Another preferred embodiment of this invention are the compounds of the formula

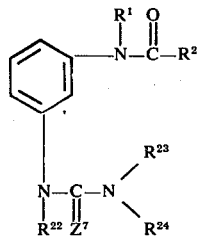

whererin $R^1$ is selected from the group consisting of hydrogen, alkoxy having a maximum of 6 carbon atoms, alkyl having a maximum of 6 carbon atoms and alkenyl having a maximum of 6 carbon atoms; $R^2$ is selected from the group consisting of alkyl having a maximum of 12 carbon atoms, alkenyl having a maximum of 10 carbon atoms, haloalkyl having a maximum of 6 carbon atoms and a maximum of four carbon atoms, cycloalkyl having 3 to 7 ring carbon atoms and a maximum of 4 chain carbon atoms, phenyl, substituted phenyl having a maximum of two substituents, said substituent being selected from the group consisting of halogen, alkyl having a maximum of four carbon atoms and —COOH, and the group

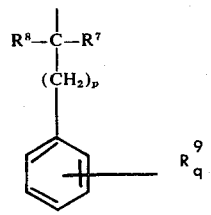

wherein $R^7$ is selected from the group consisting of hydrogen, alkyl having a maximum of 4 carbon atoms, alkenyl having a maximum of 3 carbon atoms, and haloalkyl having a maximum of 4 carbon atoms and a maximum of three halogen atoms; $R^8$ is selected from the group consisting of hydrogen, alkyl having a maximum of 4 carbon atoms and haloalkyl having a maximum of 4 carbon atoms and a maximum of 3 halogen atoms; $R^9$ is independently selected from the group consisting of alkyl having a maximum of 4 carbon atoms, alkoxy having a maximum of 2 carbon atoms, —COOH and halogen; $p$ is one of the integers 0 to 2; and $q$ is one of the integers 0 to 2; $Z^7$ is oxygen; $R^{22}$ is selected from the group consisting of hydrogen, alkyl having a maximum of 6 carbon atoms and alkenyl having a maximum of 6 carbon atoms; $R^{23}$ is selected from the group consisting of alkoxy having a maximum of 6 carbon atoms, chloroalkenyl having a maximum of 6 carbon atoms and a maximum of 3 halogen atoms, the group

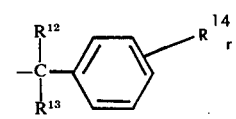

, and the group

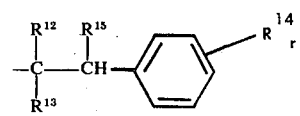

wherein $R^{12}$, $R^{13}$, $R^{14}$, $R^{15}$ and $r$ are as previously defined; and $R^{24}$ is selected from the group consisting of hydrogen, alkyl having a maximum of 12 carbon atoms and alkenyl having a maximum of 12 carbon atoms; $R^{23}$ and $R^{24}$ can with the nitrogen form the group consisting of

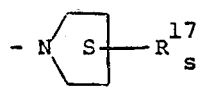

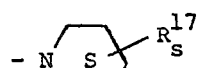    and

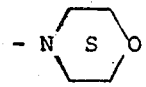

The novel compounds of this invention possess herbicidal activity.

The term "plant" as used herein and in the appended claims, is inclusive of dormant seeds, germinant seeds, germinative seeds, emerging seedlings and established woody and herbaceous vegetation including the roots and above-ground portions.

The term "control" as used herein and in the appended claims is inclusive of the actions of (1) killing, (2) inhibiting growth, reproduction of proliferation, and (3) removing, destroying or otherwise diminishing the occurrence and activity of plants and is applicable to any of the stated actions, or any combination thereof.

The terms "alkyl", "alkenyl", "alkynyl", "alkylene" and the like as used herein and in the appended claims are inclusive of both straight and branched chain radicals.

In the above formula $R^3$ $+B+_{\overline{n}}$ can be such as methyl, ethyl, n-propyl, isopropyl, n-butyl, sec-butyl, isobutyl, tertbutyl, amyl, hexyl, heptyl, octyl, nonyl, decyl, dodecyl, tetra-decyl, hexadecyl, octadecyl and the various homologues and isomers of alkyl having from 1 to 12 carbon atoms, alkenyl such as vinyl, allyl, n-butenyl-1, n-butenyl-2, n-pentenyl-2, n-hexenyl-2, 2,3-dimethylbutenyl-2, n-heptenyl, n-decenyl, n-dodecenyl and the various homologues and isomers of alkenyl having 2 to 12 carbon atoms, alkynyl such as propargyl, n-butynyl-2, n-pentynyl-3 and the various homologues and isomers of alkynyl having from 3 to 12 carbon atoms, alkoxy such as methoxy, ethoxy, n-propoxy, isopropoxy, n-butoxy, sec-butoxy, isobutoxy, tert-butoxy, hexoxy, heptoxy, dodexocy, and the various homologues and isomers of alkoxy having from 1 to 12 carbon atoms, alkenoxy such as allyloxy, n-butenoxy, n-pentenoxy, n-hexenoxy, 2,3-dimethylbutenoxy, n-heptenoxy, n-dodecenoxy and the various homologues and isomers of alkenoxy having 2 to 12 carbon atoms, alkynoxy such as propargoxy, n-butynoxy and the various homologues and isomers of alkynoxy having from 3 to 12 carbon atoms, and acyl such as methylcarbonyl, ethylcarbonyl, isopropylcarbonyl, sec-butylcarbonyl, tert-butylcarbonyl, heptylcarbonyl, decylcarbonyl, hexadecylcarbonyl, allylcarbonyl, n-butenylcarbonyl, n-pentenylcarbonyl, 2,3-dimethylbutenylcarbonyl, n-decenylcarbonyl, propargylcarbonyl, n-butynylcarbonyl and the various homologues and isomers of acyl of not more than 12 carbon atoms.

In the above formula $R^6O$—$(R^5O)_{\overline{m}}R^4$- can be alkoxyalkyl, alkenoxyalkyl, alkoxyalkoxyalkyl, alkenoxyalkoxyalkyl, dialkoxyalkyl, alkenoxy (alkoxy) alkyl, alkenoxyalkoxy (alkoxy) alkyl and alkoxyalkoxy (alkoxy) alkyl such as 2-methoxyethyl, 4-ethoxy-2-methylbutyl, 2-ethoxyethyl, 3-propoxypropyl, 4-methoxybutyl, 4-methoxy-2-ethylbutyl, 4-butoxybutyl, 2-allyloxyethyl, 2-butenoxyethyl, 4-butenoxybutyl, 2-(2-methoxyethoxy) ethyl, 2-(2-butoxyethoxy)ethyl, 4-(3-methoxypropoxy)butyl, 2-(3-allyloxypropoxy)ethyl, 2-(2-butenoxyethoxy)ethyl, 4,4-dimethoxybutyl, 2,2-diethoxyethyl, 2,4-dimethoxybutyl, 4,4-diethoxybutyl, 2-methoxy-4-allyloxybutyl, 2-ethoxy-2-propenoxyethyl, 4-(2-allyloxyethoxy)-2-methoxybutyl, 2-(4-methoxybutoxy) -2-methoxyethyl, 4-(2-methoxyethoxy)-4-butoxybutyl and the like.

In the above formula $R^2$ can be hydrogen, the alkyl, alkenyl and alkynyl listed above for $R^3$ —$(B)_{\overline{n}}$, alkoxyalkyl and alkenoxyalkyl such as methoxyethyl, ethoxyethyl, propoxypropyl, methoxybutyl, butoxybutyl, allyloxyethyl, butenoxyethyl, butenoxybutyl, ethoxyoctyl, butoxydecyl, butenoxyoctyl and the like; cycloalkyl, alkylcycloalkyl, cycloalkenyl and alkylcycloalkenyl such as cyclopentyl, 3-methoxycyclopentyl, 5-methylcyclopentyl, 3,4-dimethylcyclopentyl, 2,5-dimethylcyclopentyl, 3,4-dimethylcyclopentyl, 5-(tert-butyl)-cyclopentyl, 1-cyclohexyl, 3-methylcyclohexyl, 3,4-dimethylcyclohexyl, 2,4-dimethylcyclohexyl, 3-methylcyclohexyl, 4-butylcyclohexyl, 2,6-dimethylcyclohexyl, 3,3-dimethylcyclohexyl, 6-(tert-butyl) cyclohexyl, cycloheptyl, 3-methylcycloheptyl, 3,4-dimethylcycloheptyl, 7-methylcycloheptyl, 4,5-dimethylcycloheptyl, 6-methylcycloheptyl, 7-methylcycloheptyl, 7-(tert-butyl)cycloheptyl, 4-isopropylcycloheptyl, and the like, and aryl, alkaryl, aralkyl, and aralkenyl such as phenyl, tolyl, ethylphenyl, butylphenyl, xylyl, t-butylphenyl, diethylphenyl, diphenylmethyl, benzyl, phenylethyl, and the like.

Representative $R^{10}$ include by way of example, hydrogen, haloalkyl such as chloromethyl, iodomethyl, bromomethyl, fluoromethyl, chloroethyl, iodoethyl, bromoethyl, dichloroethyl, diiodoethyl, dibromoethyl, chloro-n-propyl, bromo-n-propyl, iodoisopropyl, bromo-n-butyl, bromo-tert-butyl, 1,3,3-trichlorobutyl, 1,3,3-tribomobutyl, chloropentyl, bromopentyl, 2,3-dichloropentyl, 3,3-dibromopentyl, chlorohexyl, bromohexyl, 2,4-dichlorohexyl, 1,3-dibromohexyl, 1,3,4-trichlorohexyl, chloroheptyl, bromoheptyl, fluoroheptyl, 1,3-dichloroheptyl, 1,4,4-trichloroheptyl, 2,4-dichloromethylheptyl, chlorooctyl, bromooctyl, iodooctyl, 2,4-dichloromethylhexyl, 2,4-dichlorooctyl, 2,4,4-trichloromethylpentyl, 1,3,5-tribromooctyl and the halogenated straight and branched chain nonyl, decyl, undecyl, dodecyl, tridecyl, tetradecyl, pentadecyl, hexadecyl and octdecyl; haloalkenyl such as chlorovinyl, bromovinyl, chloroallyl, bromoallyl, 3-chloro-n-butenyl-1, 3-chloro-n-pentenyl-1, 4-chloro-n-hexenyl-2, 3-4-dichloromethylpentenyl-1, 3-fluoro-n-heptenyl-1, 1,3,3-trichloro-n-heptenyl-5, 1,3,5-trichloro-n-octenyl-6, 2,3,3-trichloromethylpentenyl-4 and the various homologues and isomers of haloalkenyl having 2 to 12 carbon atoms; haloaryl such as o-chlorophenyl, m-chlorophenyl, m-bromophenyl, p-chlorophenyl, 2,4-dichlorophenyl, 3,5-dichlorophenyl, 2,5-diiodophenyl, and the like.

The meta bifunctional compounds of this invention can be prepared by a process represented by the following syntheses:

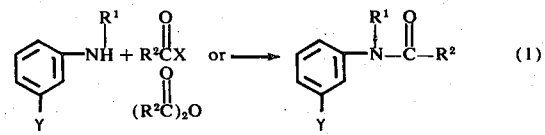

wherein Y is $SH_3$—OH or $NO_2$; X is chloro or bromo and $R^1$ and $R^2$ are as previously defined.

When Y is hydroxyl or mercapto the following synthesis represents a mode of preparation of the desired compounds:

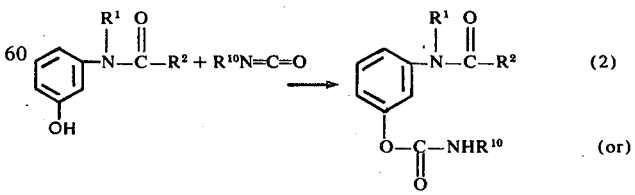

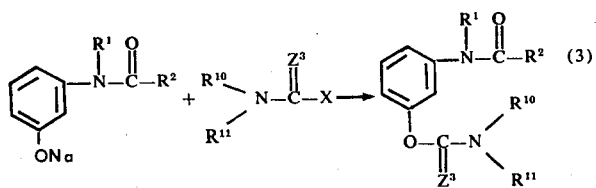
(3)
wherein $R^1$, $R^2$, $R^{10}$, $R^{11}$, $Z^3$ and X are as previously defined.
When Y is nitro the following synthesis represents a mode of preparation of the desired compounds:
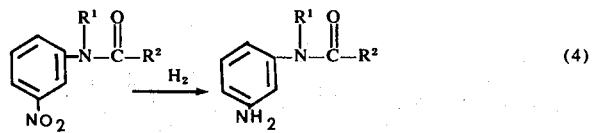
(4)
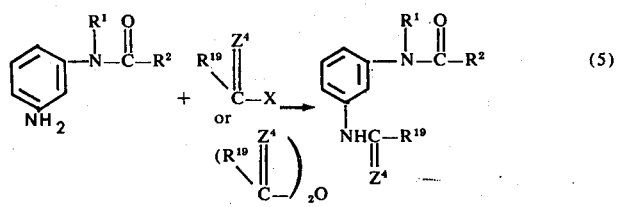
(5)
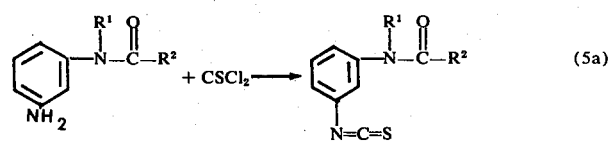
(5a)
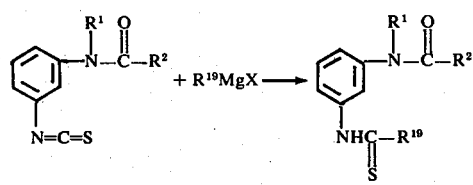
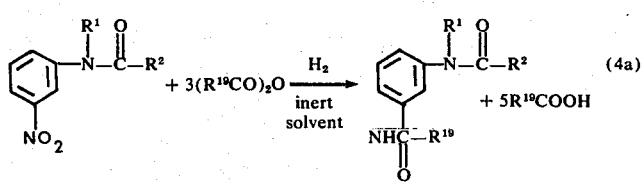
(4a)
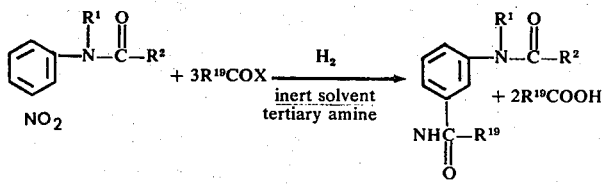
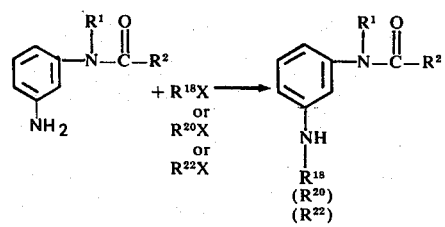
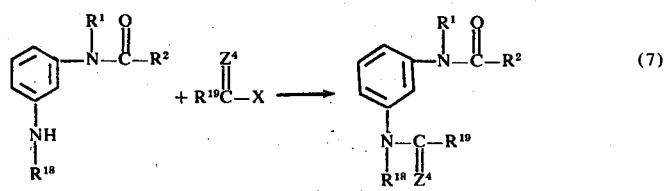
(7)

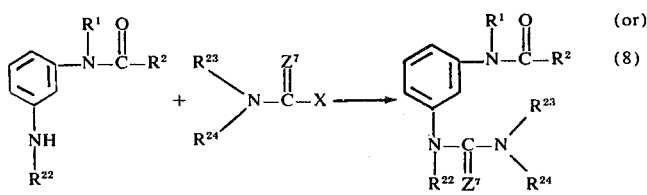

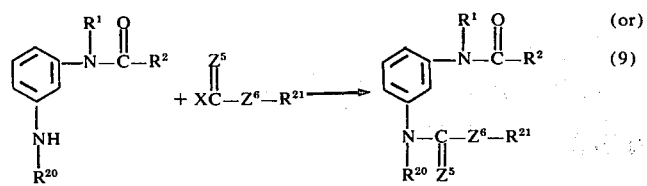

wherein $R^1$, $R^2$, $R^{18}$, $R^{19}$, $R^{20}$, $R^{21}$, $R^{22}$, $R^{23}$, $R^{24}$, $Z^4$, $Z^5$, $Z^6$, $Z^7$ and X are as previously defined.

The above reactions are represented equations as to modes of preparation of the desired compounds. Other modes are available and are listed in the literature and the following examples.

In reaction (1), where Y is hydroxy or mercapto, the reaction of the 3'-hydroxyamines or 3'-mercaptoamines with acyl halides or the appropriate anhydride can be carred out in various ways.

Normally it is desired for maximum yield that the amine be present in at least an equimolar amount to the acyl halide or the anhydride and preferably the halide or anhydride is in excess because of relative cost of the reagents. The reaction is suitably carried out at a temperature from about 0°C. to about 15°C. However, higher or lower temperatures can be used, the temperature not being critical. For example, temperatures above about 40°C. are generally employed when no acid acceptor is used and often in the range of about 80°-150°C.

With an acyl halide Reaction I is preferably carried out in the presence of an acid acceptor and an inert organic medium. When reactive acyl halides are utilized the reaction is carried out in an aqueous medium. Aqueous organic medium, such as aqueous ethyl acetate can also be utilized. The acid acceptor is generally present in at least equimolar amounts based on the amount of hydrogen halide formed in the reaction. Suitable acid acceptors, e.g. alkaline-acting or basic materials capable of binding the acid evolved in the reaction are the tertiary amines such as trimethylamine, triethylamine, pyridine, quaternary ammonium hydroxides, N-ethylmorpholine and the like; inorganic bases such as odium hydroxide and potassium hydroxide, sodium and potassium carbonate, bicarbonate and the like. An excess of amine reactant also serves as an acid acceptor.

With the anhydride Reaction I is preferably carried out in the presence of an aqueous medium.

The separation of the resulting reaction product, which are usually crystalline solids, from reaction mixture I is readily accomplished. For example, the salt, such as a tertiary amine hydrochloride salt formed during the reaction because of the presence of a tertiary amine compound therein as an acid acceptor, is separated from the product containing reaction mixture by simple means such as filtration and the solvent is removed from the resulting filtrate by stripping or distillation, preferably low temperature vacuum distillation. The product can be purified by any of the conventional means well known in the art, e.g. fractional distillation under reduced pressure, selective extraction, ractional distillation using a carrier gas or any suitable combination of these. Normally the product is sufficiently pure so that no recrystallization is necessary. If desired the product can be subjected to film distillation, recrystallization or a combination of both for further purification.

Reaction (2), as represented by the reaction of 3'-hydroxyanilides and isocyanates, can be carried out in a variety of ways. Reaction (2) is usually carried out with substantially equimolar amounts of reactants but a small excess of either reactant can be employed if desired. Reaction (2) can be carried out by simply admixing the reactants and heating at a suitable temperature, for example, from about 39°C. to about 80°C. However, reaction temperature is not critical and higher (e.g. 100°C.) or lower (e.g. 20°C.) temperatures can be employed.

Reaction (2) is advantageously carried out in the presence of at least one of the acid acceptors useful in Reaction I and an inert organic media. The amount of acid acceptor (catalyst) utilized is dependent upon the nature of the isocyanate — primary isocyanates requiring less catalyst than tertiary isocyanates. Inert organic media which can be used in Reaction (2) include, for example, hydrocarbons such as benzene, toluene, xylene, cyclohexane, methylcyclohexane, n-heptane, n-hexane and the like, organic halides such as carbon tetrachloride, n-butylchloride, ethylenedichloride, tetrachloroethylene, chlorobenzene and the like, ethyl acetate, dimethylformamide and ethers such as diethyl ether, dibutyl ether, bis(2-methoxyethyl)ether, tetrahydrofuran and the like.

The separation of the resulting reaction product from reaction mixture (2) is readily accomplished. The solvent can be removed by filtration, stripping or distillation, preferably low temperature vacuum distillation. The product if desired can be purified by any of the conventional means well known in the art, e.g. fractional distillation under reduced pressure, selective extraction, fractional distillation using a carrier gas, film distillation, recrystallization, elution or any suitable combination of these methods.

Reaction (3) of the sodium phenates of 3'-hydroxyanilides and carbamoyloxy halides is usually carried out by simply admixing the reactants and heating in the presence of an inert organic medium such as those listed above for Reaction (2). Separation of the resulting reaction product from Reaction mixture (3) is carried out by the methods described above for Reaction (2). A preferred method is to dissolve the substituted phenol in methanol and add a stoichemetric amount of 25% sodium methoxide in methanol. Approximately an equal volume of "diethyleneglycol dimethyl ether" (bix(2-methoxyethyl)ether) is added, the methanol removed under vacuum, leaving a slurry of the phenoxide in "diglyme". This is heated with the carbamoyl chloride, sodium chloride precipitating. The salt is filtered off; washed with diglyme and the filtrate vacuum evaporated to removed the solvent.

The 3'-(carbamoyloxy)anilides of this invention are liquid or crystalline solid materials which are generally insoluble in water but somewhat soluble in many organic solvents, for example alcohols, ketones, hydrocarbons such as benzene, toluene, xylene and the like and chlorohydrocarbons such as chlorobenzene, carbon tetrachloride and the like.

The starting m-nitroanilines utilized in reaction schemes 4 through 9 are commercially available or can be easily prepared by the process of reaction scheme 6.

Hydrogenation of the nitro group may be of any of the procedures known to those skilled in the art, such as catalytic hydrogenation; metal-acid combination such as iron-acid; metalalcohol combination such as zinc dust or aluminum amalgams and aqueous alcohol; lithium aluminum hydride and the like.

The procedure used may depend upon the groups already present on the ring. These procedures are also well known to those skilled in the art. The preferred procedure is catalytic hydrogenation utilizing 5% palladium on charcoal.

The order of addition, as will be illustrated by the following schemes, to the ring is not critical.

In the preparation of the product of reaction scheme 8, the following scheme illustrates other reaction that yield the desired product and also the lack of necessity for a strict order of addition.

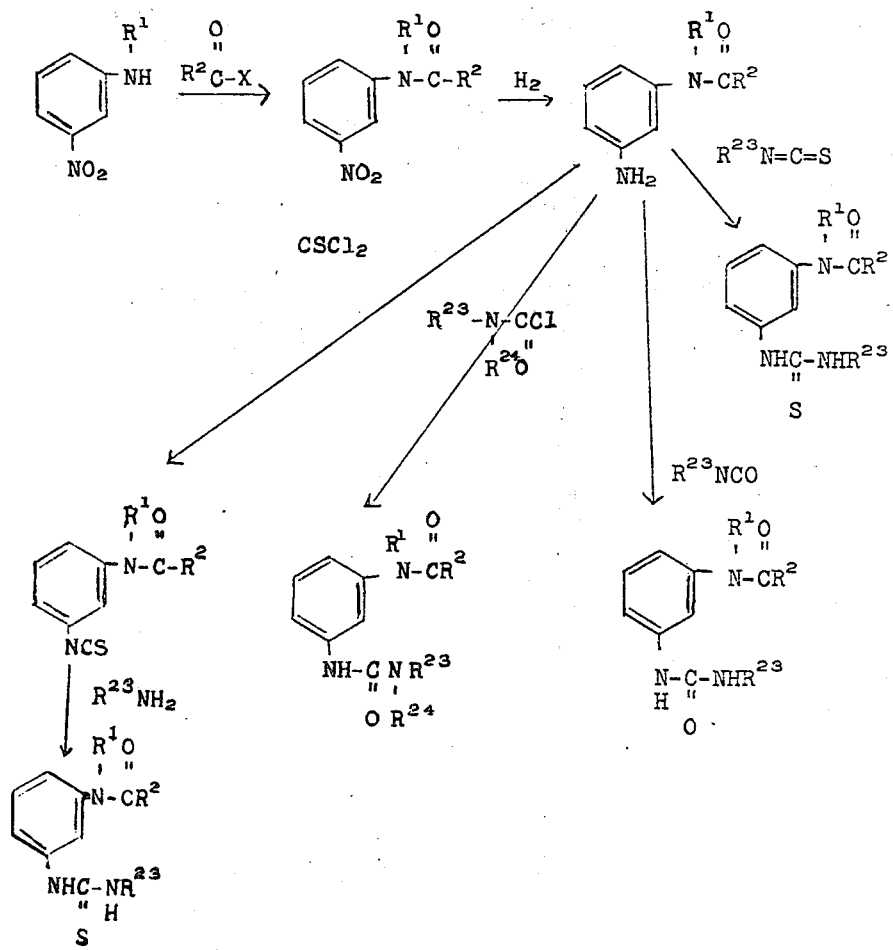

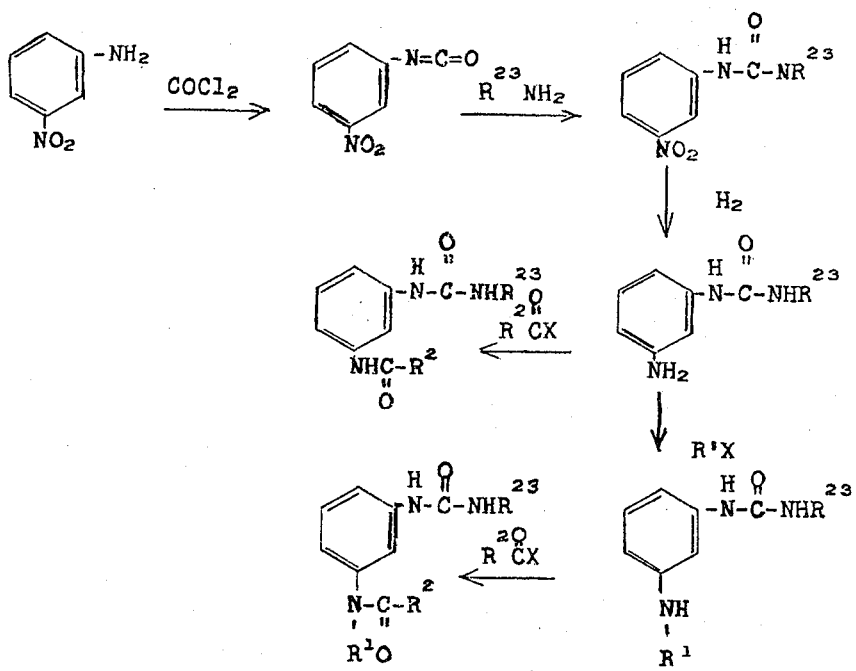

From the above reaction scheme it is seen that the starting m-nitroaniline may be reacted to form the amido group, by the known procedures which have been described previously, followed by hydrogenation of the nitro group. Conversion of the resultant amino group to a urea is illustrated by three procedures: (a) through the formation of an isocyanate or thioisocyanate followed by reaction with an amine; (b) by reaction with a substituted carbamyl chloride; and (c) by reaction with an isothiocyanate. It will be shown later that procedure (a) substituting an alcohol for the amine reactant yields the product of reaction scheme 9.

From the above reaction scheme it is seen that ureido-amido compounds can also be prepared by first converting m-nitroaniline to the isocyanate or the isothiocyanate. These compounds are commercially available. The resultant isocyanate is reacted with an amine to yield the m-nitrourea compound. The nitro group is then reduced and the amido group formed.

In the formation of the compounds of reaction scheme 5, there can either be a stepwise formation of the amido groups — starting from nitroaniline or if $R^2$ and $R^{19}$ are the same both amido groups can be formed at the same time by reaction of a m-diamine.

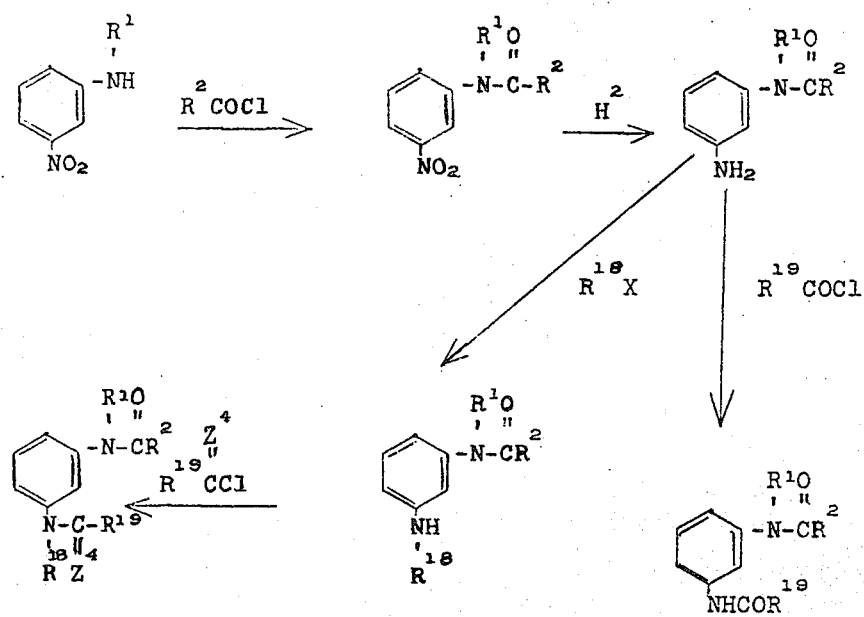

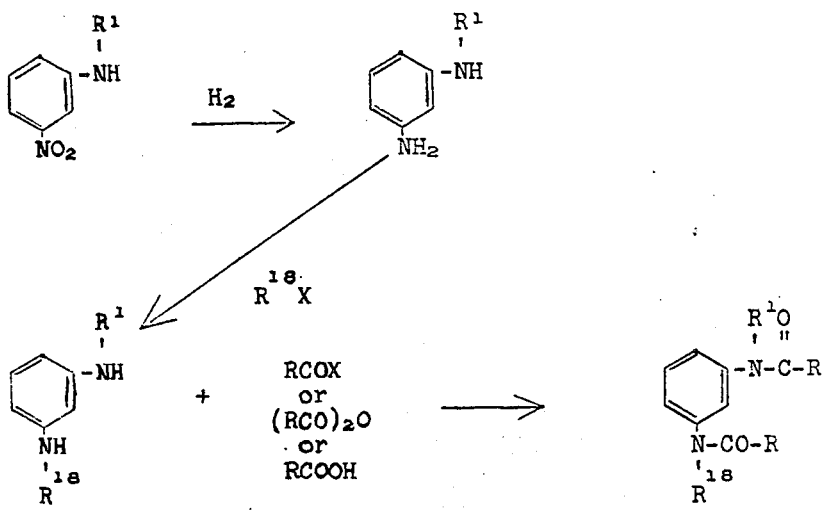

In the stepwise addition m-nitroaniline is reacted to introduce the first amido group. The nitro group is then reduced to the amino group, which can then be reacted to form a secondary amine followed by reaction to form an amido group or reacted directly to the amido group.

If both $R^2$ and $R^{19}$ are the same, the appropriate m-phenylenediamine can be reacted to form the di-amido compound.

In the formation of the product of reaction scheme 9, the following illustrates the variety of procedures available and the different order of addition, or formation of groups.

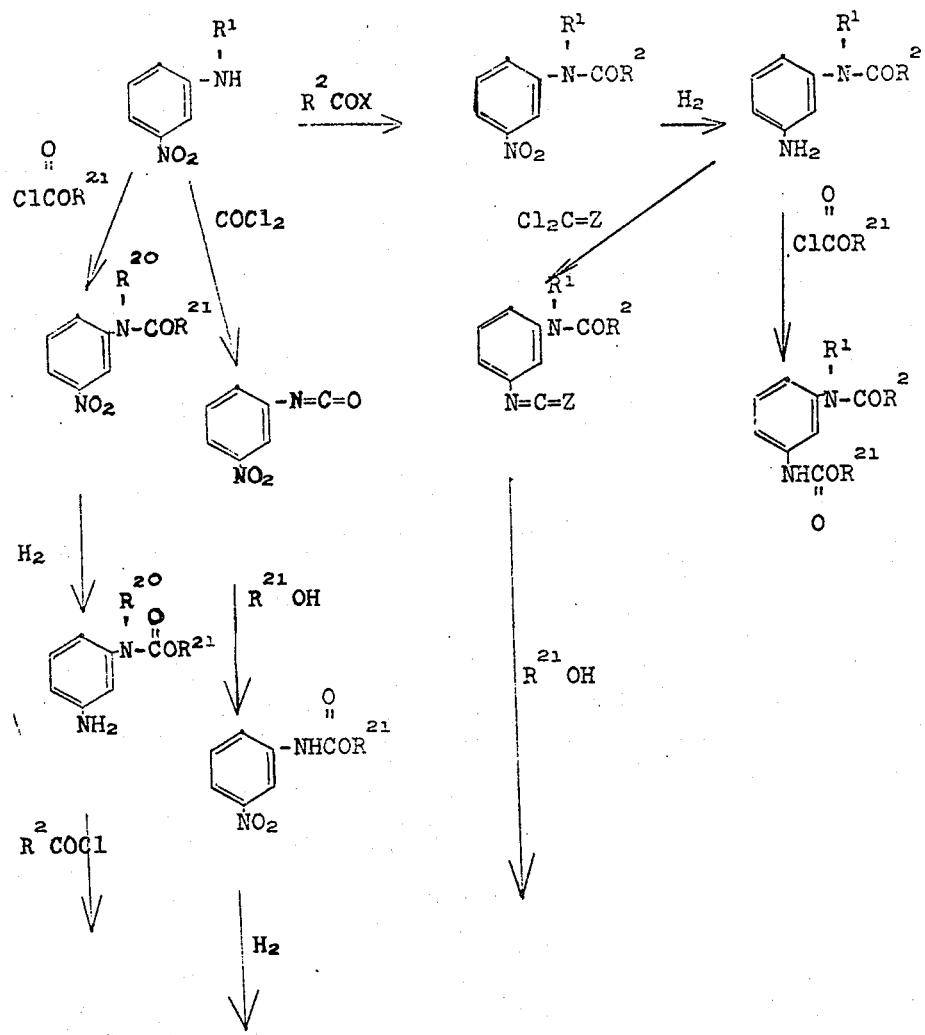

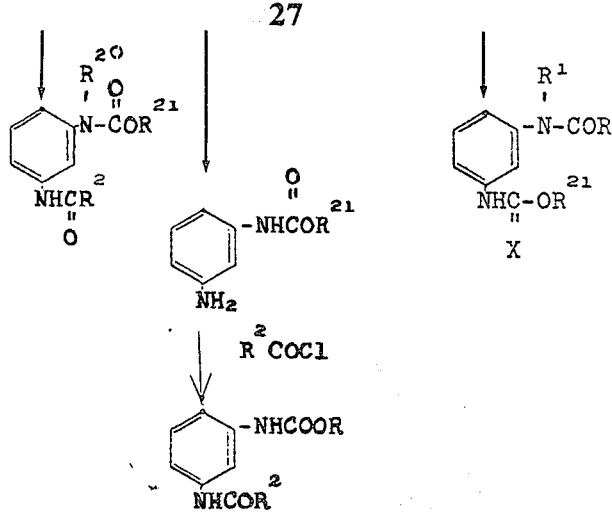

The starting m-nitroaniline can be reacted to form either the amido group; an isocyanate or a carbanilate. The nitro group is then reduced to the amino group and further reacted to form the required amido or carbanilate group.

The above reaction schemes show the interrelationship of the four groups of compounds. The reactions, starting compounds, intermediates and/or reactants to form each group are common to the groups.

It will be shown hereinafter that this interrelationship of the four groups also extends to their herbicidal activity.

The following examples will illustrate the invention. In the following examples as well as in the specification and appended claims, parts and percent are by weight unless otherwise indicated.

EXAMPLE 1

This example describes the preparation of 3'-hydroxypropionanilide. A reaction vessel in an ice bath is charged with 54.5 parts of m-aminophenol, 50 parts of $NaHCO_3$ and 150 parts of ice. Propionyl chloride, 50 parts, is added to the reaction vessel with stirring over about a 20 minute period, the temperature increasing to a maximum of about 10°C. The reaction mixture is stirred for about 2 hours at a temperature of about 5°C. The bath is removed and stirring is continued for an additional 16 hours at room temperature. The solids are removed from the reaction mixture by filtration, washed separately with water and benzene and air dried to give 73 parts of 3'-hydroxypropionanilide, m.p. 181–182°C.

EXAMPLE 2

This example describes the preparation of 3'-hydroxy-2-methylvaleranilide. A reaction vessel in an ice bath is charged with 163.5 parts of m-aminophenyl, 165 parts of $K_2CO_3$, 300 parts of water, 400 parts of ice and 450 parts of ethyl acetate. Valeryl chloride, 216 parts, is added dropwise with stirring over about a 90 minute period, the temperature increasing to a maximum of about 10°C. The bath is removed and stirring is continued for an additional 2 hours at room temperature. The reaction mixture is cooled to about 8°C and the solids are removed by filtration, washed separately with water and benzene and air dried to give 144 parts of 3'-hydroxy-2-methylvaleranilide, m.p. 136°–137°C.

Calc'd for $C_{12}H_{17}NO_2$: C, 69.54; H, 8.27. Found: C, 69.51; H, 8.37.

EXAMPLE 3

This example describes the preparation of 3'-hydroxy-2-methylpropionanilide. A reaction vessel in an ice bath is charged with 163.5 parts of m-aminophenol, 165 parts of $K_2CO_3$, 300 parts of water, 400 parts of ice and 450 parts of ethyl acetate. Isobutyryl chloride, 148 parts, is added dropwise with stirring over about a 90 minute period, the temperature rising to a maximum of about 10°C. The bath is removed and stirring is continued for an additional 2 hours at room temperature. The reaction mixture is cooled to about 8°C and the solids are removed by filtration, washed separately with water and benzene and air dried to give 225 parts of 3'-hydroxy-2-methylpropionanilide, m.p. 181°–182°C.

Calc'd for $C_{10}H_{13}NO_2$: C, 67.01; H, 7.31. Found: C, 66.97; H, 7.32.

EXAMPLE 4

This example describes the preparation of 3'-hydroxycinnamanilide. A reaction vessel in an ice bath is charged with 54.5 parts of m-aminophenol, 46 parts of $K_2CO_3$, 100 parts of water and 100 parts of ethyl acetate. Cinnamoyl chloride, 92 parts, is added to the reaction mixture with stirring over about a 1 hour period, the temperature increasing to a maximum of 15°C. The reaction mixture is stirred for about 2 hours at a temperature of about 5°C. Benzene, 100 parts, is added to the reaction mixture which is then filtered. The solids are washed separately with water and benzene and air dried to give 117 parts of 3'-hydroxycinnamanilide, m.p. 222°–223°C.

Calc'd for $C_{15}H_{13}NO_2$: C, 75.30; H, 5.48; N, 5.85. Found: C, 75.53; H, 5.68; N, 5.81.

EXAMPLE 5

This example describes the preparation of 3'-hydroxy-2-phenylacetanilide. A reaction vessel in an ice bath is charged with 54.5 parts of m-aminophenol, 46 parts of $K_2CO_3$, 100 parts of water and 100 parts of ethyl acetate. Phenylacetyl chloride, 85 parts, is added to the reaction mixture with stirring over about a 1 hour period, the temperature increasing to a maximum of 15°C. The reaction mixture is stirred for about 2 hours at a temperature of about 5°C. Benzene, 100 parts, is added to the reaction mixture which is then filtered. The solids are recrystallized from benzene/ethyl acetate, air dried and recrystallized from an aqueous solution of methyl alcohol to give 88 parts of product, m.p. 151°–152°C.

Calc'd for $C_{14}H_{13}NO_2$: C, 73.99; H, 5.77; N, 6.46. Found: C, 73.82; H, 5.67; N, 6.40.

EXAMPLE 6

This example describes the preparation of 3'-hydroxy-2-methylacrylanilide. A reaction vessel in an ice bath is charged with 209 parts of m-aminophenol, 178 parts of $K_2CO_3$, 400 parts of water, 400 parts of ice and 500 parts of ethyl acetate. Methylacrylyl chloride, 200 parts, is added over about a 90 minute period, the temperature increasing to a maximum of about 10°C. The reaction mixture is stirred for about 30 minutes at a temperature of 5° to 10°C. The bath is removed and 300 ml. of benzene are added to the reaction mixture. The reaction mixture is filtered and the solids are washed separately with (1) a 50:50 ethyl acetate/benzene mixture, (2) water, (3) a 5% aqueous solution of HCl and (4) water. The solids are dried under vacuum to give 309 parts of 3'-hydroxy-2-methylacrylanilide, m.p. 173°–175°C.

Calc'd for $C_{10}H_{11}NO_2$: C, 67.78; H, 6.26; N, 7.90. Found: C, 67.69; H, 6.21; N, 7.87.

EXAMPLE 7

This example describes the preparation of 3'-hydroxy-2,2,2-trichloroacetanilide. A reaction vessel equipped with external cooling is charged with 88 parts of m-aminophenol, 100 parts of $K_2CO_3$, 200 parts of water and 500 parts of ice. Trichloroacetyl chloride, 173 parts, is added with stirring over about a 2 hour period, the temperature increasing to a maximum of about 10°C. The reaction mixture is stirred for about 16 hours at a temperature of about 5°C. The bath is removed and the oil layer of the reaction mixture is separated by decantation, admixed with water and ethyl ether and evaporated under vacuum to remove the solvent. The residue crystals are dissolved in hot methyl alcohol, and the solution filtered. The filtrate is combined with water, cooled to about −15°C. and filtered to recover the solid product which is then washed with a 50% aqueous solution of methyl alcohol (cold) and air dried. The product amounts to about 170 parts, m.p. 122°–123°C.

Calc'd for $C_8H_6Cl_3NO_2$: C, 37.75; H, 2.38; Cl, 41.79. Found: C, 37.70; H, 2.39; Cl, 41.62.

EXAMPLE 8

This example describes the preparation of 3'-(methylcarbamoyloxy)propionanilide. A reaction vessel containing 100 parts of anhydrous dimethylformamide (DMF) and 20 parts of 3'-hydroxypropionanilide is charged with 10 parts of methyl isocyanate. No apparent reaction occurs until one part of triethylamine is added at which time the temperature increases exothermically to about 38°C. The reaction mixture is heated to about 80°C, cooled slightly and vacuum distilled to remove DMF. The residue is dissolved in methyl alcohol and filtered. The filtrate is heated, admixed with water and cooled. The solids which form upon cooling are removed by filtration to give 17.5 parts of product, m.p. 156°–160°C.

Calc'd for $C_{11}H_{14}N_2O_3$: C, 59.45; H, 6.35; N, 12.61. Found: C, 59.51; H, 6.43; N, 12.47.

EXAMPLE 9

This example describes the preparation of 3'-(t-butylcarbamoyloxy)propionanilide. A reaction vessel containing 100 parts of anhydrous dimethylformamide (DMF) and 20 parts of 3'-hydroxypropionanilide is charged with 12 parts of t-butyl isocyanate. No apparent reaction occurs until one part of triethylamine is added at which time the temperature increases exothermically to about 38°C. The reaction mixture is heated to about 80°C, cooled slightly and vacuum distilled to remove DMF. The solid residue is crystallized from hot methyl alcohol to give 13 parts of product, m.p. 197°C at 0.2°C/minute.

Calc'd for $C_{14}H_{20}N_2O_3$: C, 63.62; H, 7.63; N, 10.60. Found: C, 63.55; H, 7.64; N, 10.71.

EXAMPLE 10

This example describes the preparation of 2-methyl-3'-(methylcarbamoyloxy)propionanilide. A reaction vessel containing 100 parts of anhydrous dimethylformamide (DMF) is charged with 27 parts of 3'-hydroxy-2-methylpropionanilide and 11.4 parts of methyl isocyanate. No apparent reaction occurs until one part of triethylamine is added to the reaction mixture at which time the temperature increase exothermically to about 45°C. The reaction mixture is heated to about 90°C, cooled slightly and the DMF removed by evaporation under vacuum. The solid residue is dissolved in hot methyl alcohol and crystallized from an aqueous methyl alcohol solution to give 19 parts of product, m.p. 157.5°–158.5°C.

Calc'd for $C_{12}H_{16}N_2O_3$: C, 61.00; H, 6.83; N, 11.86. Found: C, 60.92; H, 6.79; N, 11.70.

EXAMPLE 11

This example describes the preparation of 2-methyl-3'-(methylcarbamoyloxy)propionanilide. A reaction vessel containing 100 parts of ethyl acetate and 27 parts of 3'-hydroxy-2-methylpropionanilide is charged with 11.4 parts of methyl isocyanate and one part of triethylamine. The reaction mixture is refluxed for about 1 hour, cooled and filtered. The solid is washed with ethyl acetate and air dried to give 36 parts of product, m.p. 157.5°–158.5°C.

Calc'd for $C_{12}H_{16}N_2O_3$: C, 61.00; H, 6.83; N, 11.86. Found: C, 60.89; H, 6.92; N, 11.72.

EXAMPLE 12

This example describes the preparation of 3'-(ethylcarbamoyloxy)-2-methylacrylanilide. A reaction vessel is charged with 100 parts of ethyl acetate, 17.7 parts of 3'-hydroxy-2-methylacrylanilide, 10.7 parts of ethyl isocyanate and one part of triethylamine. The reaction mixture is heated at reflux with stirring for about 1 hour and then 100 parts of benzene are added. After cooling, the solids are removed from the reaction mixture by filtration, washed with an ethyl acetate/benzene mixture and air dried to give 17.5 grams of product, m.p. 143°–145°C.

Calc'd for $C_{13}H_{16}N_2O_3$: C, 62.89; H, 6.50; N, 11.28. Found: C, 62.91; H, 6.70; N, 11.24.

EXAMPLE 13

The procedure of Example 12 is substantially repeated using 15 parts of n-butyl isocyanate in place of the 10.7 parts of ethyl isocyanate. The 3'-(t-butylcarbamoyloxy)-2-methylacrylanilide amounts to 20.5 parts, m.p. 147°–148°C.

Calc'd for $C_{15}H_{20}N_2O_3$: C, 65.20; H, 7.30; N, 10.14. Found: C, 65.21; H, 7.47; N, 10.24.

EXAMPLE 14

The procedure of Example 12 is substantially repeated using 13.8 parts of cyclohexyl isocyanate in place of 10.7 parts of ethyl isocyanate. The 3'-(cyclohexylcarbamoyloxy)-2-methylacrylanilide amounts to 15.5 parts, m.p. 191°–193°C.

Calc'd for $C_{17}H_{22}N_2O_3$: C, 67.53; H, 7.33: N, 9.27. Found: C, 67.40; H, 7.40; N, 9.10.

EXAMPLE 15

The procedure of Example 12 is substantially repeated using 16.9 parts of p-chlorophenyl isocyanate in place of the 10.7 parts of ethyl isocyanate. The 3'-(p-chlorocarbamoyloxy)-2-methylacrylanilide amounts to 27.7 parts, m.p. 176°–177°C.

Calc'd for $C_{17}H_{15}ClN_2O_3$: C, 61.73; H, 4.57; N, 8.47. Found: C, 61.86; H, 4.75; N, 8.52.

EXAMPLE 16

A reaction vessel is charged with 100 parts of ethyl acetate, 17.7 parts of 3'-hydroxy-2-methylacrylanilide, 23.3 parts of 1,1,3,3-tetramethylbutyl isocyanate and 4 parts of triethylamine. The reaction mixture is heated at reflux for about 18 hours with stirring, and then 100 parts of benzene and 50 parts of hexane are added. The reaction mixture is cooled to −15°C and filtered. The solids are washed with hexane and recrystallized from aqueous alcohol to give 12.5 parts of 3'-(1,1,3,3-tetramethylbutylcarbamoyloxy)-2-methylacrylanilide, m.p. 118°–120°C.

Calc'd for $C_{19}H_{28}N_2O_3$: C, 68.64; H, 8.49; N, 8.43. Found: C, 68.56; H, 8.42; N, 8.38.

EXAMPLE 17

A reaction vessel is charged with 100 parts of ethyl acetate, 16.3 parts of 3'-hydroxyacrylanilide, 29.5 parts of octadecyl isocyanate and one part of triethylamine. The reaction mixture is heated at reflux for about 1 hour, cooled to 20°C and filtered. The solids are washed with ethyl acetate and air dried to give 40.5 parts of 3'-(octadecylcarbamoyloxy)acrylanilide, m.p. 124°–126°C.

Calc'd For $C_{28}H_{46}N_2O_3$: C, 73.32; H, 10.11; N, 6.11. Found: C, 73.50; H, 10.24; N, 6.26.

EXAMPLE 18

The procedure of Example 17 is substantially repeated using 17.7 parts of 3'-hydroxycrotonanilide in place of the 16.3 parts of 3'-hydroxyacrylanilide. The 3'-(octadecylcarbamoyloxy)crotonanilide amounts to 41.5 parts, m.p. 134°–136°C.

Calc'd for $C_{29}H_{48}N_2O_3$: C, 73.68; H, 10.42; N, 5.93. Found: C, 73.59; H, 10.20; N, 6.09.

EXAMPLE 19

The procedure of Example 17 is substantially repeated except that 17.7 parts of 3'-hydroxycyclopropanecarboxanilide is used in place of the 16.3 parts of 3'-hydroxyacrylanilide. The 3'-(octadecylcarbamoyloxy)cyclopropanecarboxanilide amounts to 39.5 parts, m.p. 147.5°–149.5°C.

Calc'd for $C_{28}H_{46}N_2O_3$: C, 73.32; H, 10.11; N, 6.11. Found: C, 73.51; H, 10.32; N, 5.78.

EXAMPLE 20

A reaction vessel is charged with 100 parts of ethyl acetate and 17.7 parts of 3'-hydroxy-2-methylacrylanilide and heated with stirring to about 65°C. Phenyl isocyanate, 12 parts, is added. No apparent reaction occurs until one part of triethylamine is added to the reaction mixture. After a slight exothermic increase in temperature, the reaction mixture is heated at reflux for one-half hour, cooled and filtered. The solids are washed with ethyl acetate and air dried to give 22.8 parts of 3'-(phenylcarbamoyloxy)-2-methylacrylanilide, m.p. 177°–178°C.

Calc'd for $C_{17}H_{16}N_2O_3$: C, 68.91; H, 5.44; N, 9.45. Found: C, 68.76; H, 5.54; N, 9.67.

EXAMPLE 21

The procedure of Example 20 is substantially repeated using 16.9 parts of 1-naphthyl isocyanate in place of the 12 parts of phenyl isocyanate. After addition of the one part of triethylamine, 100 additional parts of ethyl acetate are added. The reaction mixture is then refluxed for about one-half hour, cooled and filtered. The solids are washed with ethyl acetate and air dried to give 31.5 parts of 2-methyl-3'-(1-naphthylcarbamoyloxy)acrylanilide, m.p. 195°–196°C.

Calc'd for $C_{21}H_{18}N_2O_3$: C, 72.82; H, 5.24; N, 8.09. Found: C, 72.63; H, 5.27; N, 8.24.

EXAMPLE 22

The procedure of Example 20 is substantially repeated using 15.4 parts of o-chlorophenyl isocyanate in place of the 12 parts of phenyl isocyanate. The 3'-(o-chlorophenylcarbamoyloxy)-2-methylacrylanilide amounts to 21 parts, m.p. 120°–123°C.

Calc'd for $C_{17}H_{15}ClN_2O_3$: C, 61.73; H, 4.57; N, 8.47. Found: C, 61.65; H, 4.56; N, 8.37.

EXAMPLE 23

The procedure of Example 20 is substantially repeated using 14.9 parts of p-methoxyphenyl isocyanate in place of the 12 parts of phenyl isocyanate. The 3'-(p-methoxyphenylcarbamoyloxy)-2-methylacrylanilide amounts to 26.5 parts, m.p. 175°–176°C.

Calc'd for $C_{18}H_{18}N_2O_4$: C, 66.25; H, 5.56; N, 8.58. Found: C, 66.52; H, 5.79; N, 8.36.

EXAMPLE 24

A reaction vessel is charged with 100 parts of ethyl acetate, 17.7 parts of 3'-hydroxycrotonanilide and 18.8 parts of 3,4-dichlorophenyl isocyanate. The reaction mixture is heated to about 55°C and one part of triethylamine is added. An additional 100 parts of ethyl acetate is added and the reaction mixture heated at reflux for about one-half hour, cooled and filtered. The solids are washed with ethyl acetate and air dried to give 31 parts of 3'-(3,4-dichlorophenylcarbamoyloxy)-crotonanilide, m.p. 193°–194°C.

Calc'd for $C_{17}H_{14}Cl_2N_2O_3$: C, 55.91; H, 3.86; N, 7.67. Found: C, 56.10; H, 4.14; N, 7.81.

EXAMPLE 25

This example describes the preparation of N-isopropyl-3'-(methylcarbamoyloxy)propionanilide. A reaction vessel is charged with 20.7 parts of 3'-hydroxy-N-isopropylpropionanilide, 100 parts of ethyl acetate, 6.9 parts of methyl isocyanate and one part triethylamine. The reaction mixture is refluxed with stirring for about 1 hour, diluted with hexane, seeded for crystal formation, and let stand for about 16 hours. The reaction mixture is filtered and the solids are washed with hexane/ethyl acetate and air dried to give 20 parts of product, m.p. 96°–99°C.

Calc'd for $C_{14}H_{20}N_2O_3$: C, 63.62; H, 7.63; N, 10.60. Found: C, 63.80; H, 7.62; N, 10.61.

EXAMPLE 26

The procedure of Example 25 was repeated using 12 parts of t-butyl isocyanate in place of the 6.9 parts of methyl isocyanate. The N-isopropyl-3'-(t-butylcarbamoyloxy)propionanilide amounts to 25.5 parts, m.p. 110°–112°C.

Calc'd for $C_{17}H_{26}N_2O_3$: C, 66.64; H, 8.55; N, 9.14. Found: C, 66.79; H, 8.59; N, 9.04.

EXAMPLE 27

This example describes the preparation of 3'-(dimethylcarbamoyloxy)-2-methylpropionanilide. A reaction vessel is charged wih 90 parts of 3'-hydroxy-2-methylpropionanilide, 300 parts of bis(2-methoxyethyl)ether(diglyme) and 108 parts of 25% solution of sodium methoxide in methyl alcohol. The reaction mixture is stirred until solution occurs and then vacuum distilled until diglyme appears in the distillate. Dimethylcarbamoyl chloride, 54 parts, is added dropwise to the distillate over about 10 minutes, the temperature increasing exothermically to about 104°C. The reaction mixture is heated to about 100°C for 25 minutes, cooled and filtered. The filtrate is evaporated under vacuum to about 25 parts. The 25 parts of filtrate are combined with about 125 parts of water and the aqueous mixture is cooled to about 5°C and filtered. The solids are washed with water and air dried to give 109 parts of product, m.p. 120°–122°C.

Calc'd for $C_{13}H_{18}N_2O_3$: C, 62.38; H, 7.25; N, 11.19. Found: C, 62.20; H, 7.41; N, 11.27.

EXAMPLE 28

This example describes the preparation of 3'-(diphenylcarbamoyloxy)-2-methylpropionanilide. A reaction vessel is charged with 45 parts of 3'-hydroxy-2-methylpropionanilide, 150 parts of diglyme and 54 parts of 25% solution of sodium methoxide in methyl alcohol. The reaction mixture is stirred until solution occurs and then vacuum distilled until diglyme appears in the distillate. Diphenylcarbamoylchloride, 58 parts, is added to the distillate with stirring, the temperature increasing exothermically to about 80°C. The reaction mixture is heated at about 120°C for one-half hour, cooled to about 90°C and filtered. The filtrate is admixed with 250 parts of methyl alcohol, cooled to about 0°C and filtered. The solids are washed with methyl alcohol and air dried to give 67 parts of product, m.p. 162.5°–163.5°C.

Calc'd for $C_{23}H_{22}N_2O_3$: C, 73.78; H, 5.92; N, 7.48. Found: C, 73.66; H, 6.09; N, 7.62.

EXAMPLE 29

This example describes the preparation of a portion of the reaction mixture used in Examples 30, 31 and 32. A vessel is charged with 165 parts of 3'-hydroxypropionanilide, 300 parts of diglyme and 216 parts of a 25% solution of sodium methoxide in methyl alcohol and a clear solution results. The solution is vacuum distilled until take-off temperature is 55°C at a pressure of 20 mm. of mercury. The residue, a straw-colored syrup amounting to 459.5 parts, is diluted with 250 parts of diglyme to form 709.5 parts of a mixture consisting primarily of the sodium phenate of 3'-hydroxypropionanilide and diglyme.

EXAMPLE 30

A reaction vessel containing 236.5 parts of the mixture prepared in Example 29 is charged with 50 parts of 1-piperidinecarbonyl chloride, the temperature increasing exothermically to about 90°C. The reaction mixture is heated at about 100°C for 1 hour, cooled to 50°C and filtered. The filtrate is vacuum distilled to a pot temperature of about 95°C. The residue is crystallized from hot methyl alcohol and the solids are washed with methyl alcohol and air dried to give 71 parts of 3'-(1-piperidinecarboxy)propionanilide, m.p. 93°–94°C.

Calc'd for $C_{15}H_{20}N_2O_3$: C, 65.20; H, 7.30; N, 10.14. Found: C, 65.34; H, 7.53; N, 10.02.

EXAMPLE 31

The procedure of Example 30 is substantially repeated using 94 parts of 4-morpholinecarbonyl chloride in place of the 50 parts of 1-piperidinecarbonyl chloride. The 3'-(4-morpholinecarboxy)propionanilide amounts to 68.5 parts, m.p. 162°–163°C.

Calc'd for $C_{14}H_{16}N_2O_4$: C, 60.42; H, 6.52; N, 10.07. Found: C, 60.20; H, 6.66; N, 10.12.

EXAMPLE 32

A reaction vessel containing 236.5 parts of the mixture prepared in Example 29 is charged with 65.9 parts of methyl(2,6-xylyl)carbamoyl chloride. The reaction mixture is heated with stirring at a temperature of about 100°C to 120°C for about 2½ hours, cooled and filtered. The filtrate is vacuum distilled to a pot temperature of 95°C. The residue is crystallized from methyl alcohol and the solids are air dried to give 91 parts of 3'-(N-methyl-2,6-dimethylcarbaniloyloxy)propionanilide.

Calc'd for $C_{19}H_{22}N_2O_3$: C, 69.92; H, 6.79; N, 8.58. Found: C, 69.93; H, 6.68; N, 8.60.

EXAMPLE 33

This example describes the preparation of 3'-(diethylthiocarbamoyloxy)propionanilide. A reaction vessel containing 33 parts of the sodium with phenate of 3'-hydroxypropionanilide is charged with 32 parts of diethylthiocarbamoyl chloride, the temperature increasing to a maximum of about 85°C. The reaction mixture is heated at 100°C for 15 minutes, cooled to 60°C and filtered. The filtrate is allowed to stand for 16 hours and a resinous material separates. The resinous material is crystallized from methyl alcohol and air dried to give 22 parts of product, m.p. 140°–141°C.

Calc'd for $C_{14}H_{20}N_2O_2S$: C, 59.97; H, 7.90; S, 11.44. Found: C, 59.85; H, 7.43; S, 11.47.

EXAMPLE 34

This example describes the preparation of 3'-amino-2,2-dimethylpropionanilide. A reaction vessel, in a water bath, was charged wih 525 parts m-nitroaniline, 1760 parts benzene and 340 parts pyridine. To this mixture was added, with stirring, 500 parts pivaloyl chloride over a period of about an hour, keeping the temperature between about 25° to 35°C. The resultant oil was washed with warm water and the organic layer concentrated to half its volume and methylcyclohexane added. Upon cooling pale-tan crystals separated out and were removed by filtration, and washed with hexane — m.p. 115°–116°C. A rocking autoclave was charged with 805 parts and 908 parts isopropyl alcohol and pressurized to 1000 psi with hydrogen. Reaction temperature increased as the pressure decreased reaching a temperature of 90°C at 0 psi with hydrogen. Repressurized three times to 500 psi. When the temperature dropped to 60°C and the pressure remained essentially constant, the vessel was emptied and washed with additional isopropanol alcohol. The combined organic was heated to reflux and filtered. Upon chilling of filtrate a solid separated which was removed by filtration, washed with 70% aqueous isopropyl alcohol, and dried — m.p. 155°–156°C.

EXAMPLE 35

This example describes the preparation of m-(2,2-dimethylpropionamido)phenylisothiocyanate. A reaction vessel was charged with 500 parts water, 500 parts ice, 373 parts and 137 parts thiophosgene. To the mixture was added, with vigorous stirring, 193 parts 3'-amino-2,2-dimethylpropionanilide over about a 10 minute period. The resultant mixture was stirred for an additional 15 minutes keeping the temperature at about 6°–7°C. To the resultant mixture was added 396 parts hexane and the mixture stirred for about 10 minutes at about 35°C. The mixture was chilled to 5°C, filtered and the solid washed with hexane, then water and dried — m.p. 141°–142°C.

EXAMPLE 36

This example describes the preparation of 1,1-dimethyl-3-[m-(2,2-dimethylpropionamido)phenyl]-thiourea. To a reaction vessel charged with 25 parts dimethylamine and 79 parts methanol was added 40 parts m-(2,2-dimethylpropionamido)phenylisothiocyanate and the resultant mixture refluxed for about 2 minutes. To the mixture was added 132 parts benzene and 87 parts toluene and the resultant mixture filtered. The filtrate was distilled under reduced pressure until crystals appeared in the residue. The distillation was continued at atmospheric pressure until the take-off temperature was about 68°C. The residue, on standing crystallized. The crystals were filtered off and washed with benzene and air dried. The crystals were heated on a water bath at 50°–60°C and 0.1 mm. pressure for a period of 4 hours. — m.p. 141.5°–142°C. Recrystallized from ethyl propionate — m.p. 141°–142°C.

EXAMPLE 37

This example describes the preparation of 3'-aminopropionanilide. m-Nitropropionanilide, prepared from m-nitroaniline and propionylchloride according to Example 34, was charged to a rocking autoclave with 897 parts isopropyl alcohol and 15 parts 5% Pd. on charcoal. The apparatus was purged and pressurized to 1000 psi with hydrogen. Upon rocking, the reaction temperature rose to about 125°C. Cooled reaction mixture to 50°C and repressurized to 500 psi with hydrogen. Reaction temperature rose to 100°C. Cooled reaction mixture to 70°C and repressurized to 500 psi. Reaction temperature rose to 90°C. Cooled reaction mixture to 70°C and repressurized to 500 psi with hydrogen. No temperature increase occurred. Maintained this temperature for about 2 hours without much loss in pressure. The mixture was filtered and the filtrate vacuumed distilled to a pot temperature of about 90°–100°C at 0.2 mm. The residue was cooled and seeded yielding an off-white solid — m.p. 92°–93.5°C.

EXAMPLE 38

This example describes the preparation of 1,1-dimethyl-3-(m-propionamidophenyl)urea. To a suitable reaction vessel was charged 16.4 parts 3'-aminopropionanilide, 10.8 parts dimethylcarbamoyl chloride, 8.7 parts pyridine and 62 parts dioxane. The resultant mixture was stirred about one-half hour and then let stand for about 18 hours. After standing about 1 hour a brownish "tar" separated from solution. After standing for about 18 hours, water was added to the mixture until the tar dissolved and the resultant mixture cooled to below 0°C for about 1 hour during which time crystallization occurred. The mixture was filtered and the crystals washed with 50% aqueous methanol and air dried — m.p. 62°–70°C. Recrystallized from 35% aqueous methanol — m.p. 70.5°–71.5°C.

EXAMPLE 39

This example describes the preparation of 1-allyl-3-(m-propionanilide)urea. To a suitable reaction vessel was charged 8.2 parts 3'-aminopropionanilide, 52 parts dioxane and 4.6 parts allylisocyanate. The resultant mixture was heated to about 80°C and 45 parts benzene added. The mixture was let stand overnight and the solid which formed on standing was removed by filtration, washed with benzene and dried — m.p. 173°–174°C.

EXAMPLE 40

This example describes the preparation of 3'-isothiocyanatopropinanilide. To a suitable vessel was charged 75 parts thiophosgene, 500 parts ice, 300 parts water and 300 parts chloroform. To the resultant mixture was added over a 10 minute period, with stirring, 82 parts 3'-aminopropionanilide. A solid material separated from the mixture. Due to the presence of the ice, the reaction temperature remained at about 5°C for the first hour, then rose to room temperature during the second hour as the ice melted. n-Hexane, 198 parts was added to the mixture, stirred a few minutes and filtered. The product — a whitish-tan powder — was washed with water then hexane and dried — m.p. 102°–102.5°C.

EXAMPLE 41

This example describes the preparation of 1-methoxy-1-methyl-3-(m-propionamidophenyl)thiourea. To a suitable reaction vessel was charged 10.3 parts 3'-isothiocyanatopropionanilide and 39.5 parts methanol. To the resultant mixture was added a methanolic solution of O,N-dimethylhydroxylamine, containing 4.9 parts of the hydroxylamine. (The hydroxylamine solution was prepared by the neutralization, in methanol, of the hydroxylamine hydrochloride with sodium methoxide.) The resultant solution was heated to about 60°C and maintained at this temperature for about 15 minutes. Hot water was added to the mixture until the final volume was about 3 times the original file. This solution was cooled to below 0°C and maintained at this temperature overnight. The crystals which separated out on standing, were removed by filtration, washed with water and air dried — m.p. 129°–130°C.

EXAMPLE 42

This example describes the preparation of 1,1-dimethyl-3-(m-aminophenyl)urea. To a suitable reaction vessel was charged 100 parts m-nitrophenylisocyanate and 361 parts dioxane. Dimethylamine (47 parts) was passed over the resultant mixture which was being stirred. The mixture was heated to about 70°C and 300 parts water added, the mixture filtered and water added to the filtrate until cloudiness appeared. This required about 200 parts additional water. The mixture was cooled to about 15°C and seeded. The desired product — pale yellow flakes — were removed by filtration, washed with 50% aqueous methanol and air dried — m.p. 126°–127°C.

The above product was charged to a rocking autoclave with 487 parts dioxane and 5 parts 5% palladium on charcoal. Autoclave was pressurized with hydrogen to 1000 psi and the autoclave rocked and repressurized as needed until uptake of hydrogen had substantially stopped. The mixture was filtered and the filtrate vacuum distilled until about one-third of its volume had been removed. To the residue was added 66 parts methanol and the mixture heated to reflux, cooled, filtered and the filtrate heated to reflux. To this solution was added 300 parts water, the mixture cooled to below 0°C and maintained at this temperature overnight. The mixture was then distilled until about two-thirds of its volume was removed. A thick mass separated from solution which was removed and dissolved in 198 parts hot isopropanol, filtered and 220 parts benzene added to the filtrate. The resultant mixture was in an ice bath and seeded. The resultant precipitate was removed by filtration, washed with benzenethylacetate solution and air dried — m.p. 125°–126°C.

EXAMPLE 43

This example describes the preparation of 1,1-dimethyl-3-[3'-(2,2,2-trimethylacetamido)phenyl]urea. To a suitable reaction vessel was added 36 parts 1,1-dimethyl-3-(m-aminophenyl)urea, 28 parts potassium carbonate, 90 parts ethyl acetate 200 parts ice and 50 parts water. To the resultant mixture was added, with stirring, 36 parts pivaloyl chloride over a 20 minute period. The mixture was then stirred about 1 hour and an additional 90 parts ethyl acetate added. The water layer was separated. The organic layer was heated to about 65°C and then cooled. The desired product — which separated as a solid — was removed by filtration, washed with a benzene-hexane mixture, then water and dried. The product was recrystallized from methanol — m.p. 192°–193°C.

EXAMPLE 44

This example describes the preparation of 3'-propionamidocyclopropylcarboxanilide. To a suitable reaction vessel was charged 16.2 parts 3'-aminopropionanilide, 13.8 parts potassium carbonate, 100 parts water, 200 parts ice and 90 parts ethyl acetate. To this mixture was added, with stirring, a solution of cyclopropylcarbonyl chloride in benzene (prepared from 15.8 parts cyclopropylcarbonyl chloride and 26 parts benzene) over a 5 minute period. To the resultant mixture was added 99 parts n-hexane and then stirring continued for an additional one-half hour. The mixture was filtered and the solid, which is the desired product, was washed with benzene, water air dried. Solid recrystallized from aqueous methanol — m.p 199°–200°C.

EXAMPLE 45

The preparation of 3'-crotonamidopropionanilide was carried out by the procedure described in Example 44, substituting 15.8 parts crotonyl chloride for the cyclopropylcarbonyl chloride. The product, after recrystallization from aqueous methanol, melted at 195°–197°C.

EXAMPLE 46

This example describes the preparation of 3'-(2,2-dimethylvaleramido)2,2-dimethylvaleranilide. To a suitable reaction vessel, cooled in a water bath, was charged 87 parts m-phenylenediamine, 790 parts acetone and 190 parts triethylamine. To this solution was added, with stirring, 260 parts 2,2-dimethylvaleryl chloride. The resultant solution was added to 1000 parts water, whereupon an oil separated out which crystallized. The solid, which is the desired product, was washed with 5% hydrochloric acid, 5% sodium hydroxide, water and dried — m.p. 109°–111°C.

EXAMPLE 47

The preparation of 3'-(2,2-dimethylpropionamido)-3,3-dimethylbutyranilide was carried out by the procedure described in Example 44, substituting 20.2 parts 3,3-dimethylbutyryl chloride for the cyclopropylcarbonyl chloride. The desired product melted at 184°–185°C.

Analysis Calc'd: C, 70.31; H, 9.03; N, 9.5. Found: C, 70.39; H, 9.14; N, 9.50.

EXAMPLE 48

The preparation of 3'-(2-methylvaleramido)-2,2,3-trimethyl-4-pentenanilide was carried out by the procedure described in Example 44, substituting 20.6 parts 3'-amino-2-methylvaleranilide for the 3'-aminopropionanilide and 24.1 parts of 4-pentenoyl chloride for the cyclopropylcarbonyl chloride. The desired product melted at 112°–115°C.

Analysis, Calc'd: C, 72.91; H, 8.87; N, 8.51. Found: C, 73.04; H, 9.24; N, 8.32.

EXAMPLE 49

This example describes the preparation of 3'-(propionamido)-2,2-dimethyl-4-pentenoanilide. To a suitable reaction vessel was charged 3.2 parts 3'-aminopropionanilide, 7 parts potassium carbonate, 25 parts water, 31 parts benzene, 13 parts toluene and 50 parts ice. To this mixture was added, with stirring, in one portion a benzene solution of 2,2-dimethyl-4-pentenoyl chloride (prepared from 8.8 parts 2,2-dimethyl-4-pentenoyl chloride and 22 parts benzene). The resultant mixture was stirred for 5 minutes and then warmed, with stirring for about 30 minutes until a temperature of about 25°C was obtained. To this mixture was added 66 parts n-hexane and the mixture, after stirring, filtered and the desired product, which was a solid, washed with hexane, water and air dried — m.p. 119.5°–121.5°C. Recyrstallized from benzene — m.p. 123°–125°C.

Analysis, Calc'd: C, 70.24; H, 7.75; N, 10.24. Found: C, 70.12; H, 7.69; N, 10.10.

EXAMPLE 50

This example describes the preparation of methyl m-aminocarbanilate. To a suitable reaction vessel, cooled in an ice bath, was charged 500 parts m-nitroaniline, 315 parts potassium carbonate, 800 parts water, 800 parts ice and 900 parts ethylacetate. To this mixture, at below about 15°C, was added over about a 2 hour period with stirring 380 parts methyl chloroformate. To the resultant mixture was added 330 parts n-hexane and the mixture stirred for an additional 2 hours at a temperature in the approximate range of 25°–30°C. The mixture was filtered and the product washed with a 50:50 n-hexane-ethyl acetate solution, water and air dried — 148°–150°C.

The above solid was charged to a rocking autoclave and 9 parts 5% palladium on charcoal and 1236 parts dioxane. The autoclave was purged and charged with hydrogen to 800 psi. On rocking the reaction temperature increased to about 80°C as the pressure decreased. The autoclave was repressurized to 500 psi when necessary until the pressure remained essentially constant at about 60°C. The mixture was filtered and the filtrate vacuum distilled to a pot temperature of 80°C at 0.2 mm. pressure. The residue, an oil, crystallized on standing overnight. Recrystallized from aqueous methanol and then an ethyl acetate-toluene-methylcyclohexane solution — m.p 71°–71.5°C.

EXAMPLE 51

This example describes the preparation of methyl m-(2-methylvaleramido)carbanilate. To a suitable reaction vessel was charged with 16.6 parts methyl m-aminocarbanilate, 18 parts potassium carbonate, 100 parts water, 300 parts ice and 89 parts ethyl propionate. To this mixture was added over a 10 minute period, with stirring, a benzene solution of 2-methylvaleroyl chloride (20.2 parts 2-methylvaleroyl chloride and 52.8 parts benzene). The mixture was heated to about 75°C, then let stand overnight. Crystals separated on standing. The crystals were removed by filtration, washed with water and ethyl acetate-hexane solution and air dried — m.p. 110°–112°C.

EXAMPLE 52

This example describes the preparation of methyl m-propionamidothionocarbanilate. To a suitable reaction vessel was charged with m-propionamidophenyl isothiocyanate (prepared from m-aminopropionanilide and thiophosgene), 80 parts methanol and 7.3 parts triethylamine and the mixture refluxed for about 14 hours. The mixture was cooled and the mixture was vacuum "evaporated" leaving a solid residue. The solid was dissolved in 73 parts methanol, the mixture filtered and the filtrate heated to about 60°C, about 50 parts water added, seeded and cooled. The desired product was separated and dried — m.p. 150°–152°C.

EXAMPLE 53

This example describes the preparation of methyl m-propionamidothiolcarbanilate. To a suitable reaction vessel was charged with 16.4 parts 3'-aminopropionanilide, 14 parts potassium carbonate, 100 parts water, 100 parts ice and 90 parts ethyl acetate. To this mixture was added over a 5 minute period, with stirring, 13 parts methyl chlorothioformate. To this mixture was added 66 parts n-hexane and the mixture filtered. The desired product — a solid — was washed with 3:2 hexane-ethyl acetate mixture, water and air dried — m.p. 167°–168°C.

The following carbamoyloxyanilides were prepared by substantially the same procedure as previously shown. In the naming of the compounds a C=S in the amido group is referred to as a thioamido such as

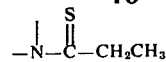

would be named "propionthioamido". In the case of "acetamido" the term "thioacetamido" will be used. Replacement of sulfur for oxygen in the carbamoyloxy group will be named as follows:

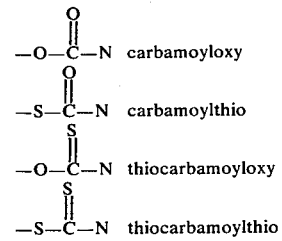

The nitrogen atom in the carbamoyl group will be referred to as "N" and the nitrogen atom in the amido group will be referred to as "N".

3'-(N-sec-butylcarbamoyloxy)formanilide
3'-(N-N-diallylcarbamoyloxy)formanilide
3'-(N-1-methyl-2-methoxyethylcarbamoyloxy)formanilide
3'-(N-benzylcarbamoyloxy)formanilide
3'-(N-4'-methylbenzylcarbamoyloxy(formanilide
3'-(N-4'-methoxybenzylcarbamoyloxy)formanilide
3'-(N-alpha-tertiarybutyl-4'-methoxybenzylcarbamoyloxy)formanilides
3'-(N-2',6'-dimethylphenylcarbamoyloxy)formanilide
3'-(N-alpha-methylbenzylcarbamoyloxy)formanilide
3'-(N-3-phenyl-i-propylcarbamoyloxy)formanilide
3'-(N-2-phenylethylcarbamoyloxy)formanilide
3'-(N-1,1-dimethyl-2-phenylethylcarbamoyloxy)formanilide
3'-(N-alpha-methyl-4'-chlorobenzylcarbamoyloxy)-formanilide
3'-(N-1-phenyl-n-propylcarbamoyloxy)formanilide
3'-(N-1-phenyl-n-butylcarbamoyloxy)formanilide
3'-(N-methyl-N-3'-chlorobenzylcarbamoyloxy)formanilide
3'-(N-i-propyl-N-4'-chlorobenzylcarbamoyloxy)formanilide
3'-(N-2-chloroallyl-N-benzylcarbamoyloxy)formanilide
3'-(N-methyl-N-alpha-methylbenzylcarbamoyloxy)-formanilide
3'-(N-1,1-diphenylmethylcarbamoyloxy)formanilide
3'-(N-methyl-N-1-naphthylmethylcarbamoyloxy)-formanilide
3'-(N-methylcarbamoyloxy)-2,2-dimethylbutanoanilide
3'-(N-methylcarbamoyloxy)tridecanoanilide
3'-(N-methylcarbamoyloxy)capranilide
3'-(N-methylcarbamoyloxy)caproanilide
3'-(N-1,2-dimethylbutylcarbamoyloxy)2,2-dimethylvaleranilide
3'-(N-n-butylcarbamoyloxy)-2,2-dimethylvaleranilide
3'-(N-ethylcarbamoyloxy)acetanilide
3'-(N,N-dimethylcarbamoyloxy)-2,2-dimethylvalderanilide
3'-(N,N-di-n-propylcarbamoyloxy)2,2,4-trimethylvalderanilide 3'-(N,N-di-i-propylcarbamoyloxy)2,2,4-trimethylvalderanilide
3'-(N-tert-butylcarbamoyloxy)2,2-dimethylvalderanilide
3'-(N-1,1,3,3-tetramethylbutylcarbamoyloxy)2,2,4-trimethylvaleranilide
3'-(N-2-ethylhexylcarbamoyloxy)2,2-dimethylpropionanilide
3'-(N-n-butylcarbamoyloxy)2,2,4-trimethylvaleranilide
3'-(N-1,3-dimethylbutylcarbamoyloxy)2,2-dimethylvaleranilide
3'-(N-1,1,3,3-tetramethylbutylcarbamoyloxy)2,2-dimethylvaleranilide
3'-(N-methylcarbamoyloxy)2,2-dimethylvalderanilide
3'-(N-1,1,3,3-tetramethylbutylcarbamoyloxy)acetanilide
3'-(N-sec.butylcarbamoyloxy)2,2-dimethylpropionanilide
3'-(N-sec.butylcarbamoyloxy)2-methylvaleranilide
3'-(N-1,2-dimethylbutylcarbamoyloxy)2,2-dimethylpropionanilide
3'-(N-1-methylheptylcarbamoyloxy)propionanilide
3'-(N-N-dimethylthiocarbamoyloxy)propionanilide
3'-(N,N-diethylcarbamoyloxy)2,2-dimethylpropionanilide
3'-(N-t-butylcarbamoyloxy)2,2-dimethylpent-4-enanilide
3'-(N-allylcarbamoyloxy)2,2-dimethylvaleranilide
3'-(N,N-diallylcarbamoyloxy)acetanilide
3'-(N,N-diallylcarbamoyloxy)2-methylvaleranilide
3'-(N-1-methyl-2-methoxyethylcarbamoyloxy)2-methylvaleranilide
3'-(N-n-butyl-N-2'-chlorobenzylcarbamoyloxy)propionanilide
3'-(N-t-butyl-N-2',4'-dichlorobenzylcarbamoyloxy)propionanilide
3'-(N-allyl-N-2-phenylethylcarbamoyloxy)acetanilide
3'-(N-allyl-N-2-phenylethylcarbamoyloxy)-2-methylvalderanilide
3'-(N-allyl-N-2'-chlorobenzylcarbamoyloxy)propionanilide
3'-(N-allyl-N-2'-chlorobenzylcarbamoyloxy)propionanilide
3'-(N-1,3-dimethylbutyl-N-4'-chlorobenzylcarbamoyloxy)propionanilide
3'-(N-cyclohexyl-N-4'-chlorobenzylcarbamoyloxy)propionanilide
3'-(N-2',6'-dimethylphenylcarbamoyloxy)2-methylvaleranilide
3'-(N-2-chloroallyl-N-benzylcarbamoyloxy)propionanilide
3'-(N-2,3,3-trichloroallyl-N-benzylcarbamoyloxy)propionanilide
3'-(N-methyl-N-alpha-t-butylbenzylcarbamoyloxy)propionanilide
3'-(N-2,3-dichloroallyl-N-benzylcarbamoyloxy)propionanilide
3'-(N-n-propyl-N-2',4'-dichlorobenzylcarbamoyloxy)propionanilide
3'-(N-methyl-N-2-phenylethylcarbamoyloxy)propionanilide
3'-(N-i-propyl-N-benzylcarbamoyloxy)propionanilide
3'-(N-methyl-N-alpha-ethylbenzylcarbamoyloxy)propionanilide 3'-(N-methyllyl-N-benzylcarbamoyloxy)propionanilide
3'-(N-t-butyl-N-4'-chlorobenzylcarbamoyloxy)propionanilide
3'-(N-2-chloroallyl-N-benzylcarbamoyloxy)propionanilide
3'-(N-methyl-N-3',4'-dichlorobenzylcarbamoyloxy)propionanilide
3'-(N-i-propyl-N-benzylcarbamoyloxy)propionanilide)
3'-[N-methyl-N-(2,4,6-trimethylbenzyl)carbamoyloxy]propionanilide
3'-[N-methyl-N-(2-chlorozenyl)carbamoyloxy]2-methylvaleranilide
3'-[N-(2-fluorophenyl)carbamoyloxy]2-methylpropionanilide
3'-[N-(2-fluorophenyl)carbamoyloxy]2,2-dimethylvaleranilide
3'-(N-t-butylcarbamoyloxy)2,2-dimethyl-3-phenyl-4-pentenoanilide
3'-(N-t-butylcarbamoyloxy)2,2-dimethyl-3-(3,4-dichlorophenyl)propionanilide
3'-[N-methyl-N-(1-methyl-2-phenylethyl)carbamoyloxy]2-methylvaleranilide
3'-[N-methyl-N-(1-methyl-2-phenylethyl)carbamoyloxy]2,2-dimethylvaleranilide
3'-(N-1,1-dimethyl-2-phenylethylcarbamoyloxy)acetanilide
3'-[N-(4-methoxybenzyl)carbamoyloxy]acetanilide
3'-[N-alpha-t-butyl-4-methoxybenzyl)carbamoyloxy]acetanilide
3'-[N-(alpha-t-butyl-4-methoxybenzyl)carbamoyloxy]2,2-dimethylvaleranilide
3'-(N-(1-methyl-2-phenylethylcarbamoyloxy)2-methylvalderanilide
3'-(N-(4methoxybenzyl)carbamoyloxy)2,2-dimethylvaleranilide
3'-(N-(1,1-dimethyl-2-phenylethyl)carbamoyloxy)2-methylvaleranilide
3'-(N-(alpha-isopropylbenzyl)carbamoyloxy)2,2-dimethylpropionanilide
3'-(N-(1,1-dimethyl-2-phenylethyl)carbamoyloxy)2,2-dimethylvaleranilide
3'-(N-(alpha-n-propylbenzyl)carbamoyloxy)2,2-dimethylvaleranilide
3'-(N-(alpha-isopropylbenzyl)carbamoyloxy)2,2-dimethylvaleranilide
3'-(N-diphenylmethylcarbamoyloxy)2,2-dimethylvaleranilide
3'-(N-diphenylmethylcarbamoyloxy)2,2-dimethylpropionanilide
3'-(N-diphenylmethylcarbamoyloxy)propionanilide
3'-(N-(4-dimethylphenyl)carbamoyloxy)acetanilide
3'-(N,N-diphenylcarbamoyloxy)2,2-dimethylvaleranilide
3'(N-(2,3-dimethylphenyl)carbamoyloxy)acetanilide
3'-(N-methyl-N-(2-methyl-2-t-butylphenyl)carbamoyloxy)2,2-dimethylpropionanilide
3'-(N-methyl-N-(2-methyl-2-t-butylphenyl)carbamoyloxy)2,2-dimethylvaleranilide
3'-(N-isopropyl-N-phenylcarbamoyloxy)propionanilide
3'-(N-methyl-N-(2,6-dimethylphenyl)carbamoyloxy)2,2-dimethylvaleranilide
3'-(N-(alpha-methylbenzyl)carbamoyloxy)acetanilide 3'-(N-(alpha-methylbenzyl)carbamoyloxy)2,2-dimethylpropionanilide
3'-(N-(alpha-methylbenzyl)carbamoyloxy)2,2,4-trimethylvaleranilide
3'-(N-phenylcarbamoyloxy)2,2-r-trimethylvaleranilide
3'-(N-(4-5-butylphenyl)carbamoyloxy)propionanilide
3'-(N-methyl-N-cinnamylcarbamoyloxy)propionanilide
3'-(N-methyl-N-(2-naphthyloxyethyl)carbamoyloxy)propionanilide
3'-(N-methyl-N-(2-phenoxyethyl)carbamoyloxy)propionanilde
3'-(N-ethyl-N-(1-naphthylmethyl)carbamoyloxy)propionanilide
3'-(N-isopropyl-N-cyclohexylcarbamoyloxy)2,2-dimethylpropionanilide
3'-(N-(2,6-diethylcyclohexyl)carbamoyloxy)methacrylanilide
3'-(piperidylcarbamoyloxy)2,2,3-trimethylvaleranilide
3'-(2,6-dimethylpiperidylcarbamoyloxy)2,2,3-trimethylvaleranilide
3'-(2,6-dimethylpiperidylcarbamoyloxy)2-methylvaleranilide
3'-(2,6-dimethylpiperidylcarbamoyloxy)2-methylvaleranilide
3'-(2,6-dimethylpiperidylcarbamoyloxy)2-methylvaleranilide
3'-(piperidylcarbamoyloxy)2,2-dimethylvaleranilide
3'-(pyrrolidylcarbamoyloxy)2,2,4-trimethylvaleranilide
3'-(pyrrolidylthiocarbamoyloxy)propionanilide
3'-(2,6-dimethylpiperidylcarbamoyloxy)2,2-dimethylpropionanilide
3'-(morpholinylcarbamoyloxy)2,2-dimethylpropionanilide
3'-(N-t-butylcarbamoyloxy)2-methyl-2-n-propyl-4-pentenoanilide
3'-(N-isopropylcarbamoyloxy)2,2-dimethyl-4-pentenoanilide
3'-(N-2-ethylhexylcarbamoyloxy)acrylanilide
3'-(N-2,2,4-trimethylbutylcarbamoyloxy)methacrylanilide
3'-(N-2,3-dimethylbutylcarbamoyloxy)crotonanilide
3'-(N-n-propylcarbamoyloxy)methacrylanilide
3'-(N-1-methylhexylcarbamoyloxy)acrylanilide
3'-(N,N-diallylcarbamoyloxy)methacrylanilide
3'-(N,N-diallycarbamoyloxy)crotonanilide
3'-(N,N-diallylcarbamoyloxy)acrylanilide
3'-(N-allylcarbamoyloxy)2,4-hexadieoanilide
3'-(N-(1-methyl-2-methoxyethyl)carbamoyloxy)methacrylanilide
3'-(N-(1-methyl-2-methoxyethyl)carbamoyloxy)acrylanilide
3'-(N-(2-fluorophenyl)carbamoyloxy)acrylanilide
3'-(N-(2-fluorophenyl)carbamoyloxy)2,2-dimethyl-4-pentenanilide
3'-(N-alpha-isopropylbenzyl)carbamoyloxy)methacrylanilide
3'-(N-(alpha-n-propylbenzyl)carbamoyloxy)methacrylanilide
3'-(N-(2-phenylethyl)carbamoyloxy)methacrylanilide
3'-(N-(alpha-methyl-2-phenylethyl)carbamoyloxy)methacrylanilide
3'-(N-(alpha-t-butyl-4-methoxybenzyl)carbamoyloxy)methacrylanilide
3'-(N,N-diphenylcarbamoyloxy)crotonanilide
3'-(N-methyl-N-(2-methyl-6-t-butylphenyl)carbamoyloxy)crotonanilide
3'-(N-benzylcarbamoyloxy)acrylanilide
3'-(N-(alpha-methyl-4-chlorobenzyl)carbamoyloxy)acrylanilide
3'-(N,N-diphenylcarbamoyloxy)acrylanilide
3'-(N-methyl-N-(2,6-dimethylphenyl)crotonanilide
3'-(N-isopropyl-N-phenylcarbamoyloxy)crotonanilide
3'-(N-methyl-N-(2,6-dimethylphenyl)carbamoyloxy)acrylanilide
3'-(N-isopropyl-N-phenylcarbamoyloxy)acrylanilide
3'-(N-(alpha-methylbenzyl)carbamoyloxy)methacrylanilide
3'-(N-(2,3-dimethylphenyl)carbamoyloxy)methacrylanilide
3'-(N-(2,6-dimethylphenyl)crotonanilide
3'-(N-(2,6-dimethylphenyl)carbamoyloxy)methacrylanilide
3'-(N-(4-t-butylphenyl)carbamoyloxy)crotonanilide
3'-(N-(4-t-butylphenyl)carbamoyloxy)methacrylanilide
3'-(N-(4-t-butylphenyl)carbamoyloxy)acrylanilide
3'-(N-(2,6-diethylcyclohexyl)carbamoyloxy)crotonanilide
3'-(N-cyclohexylcarbamoyloxy)crotonanilide
3'-(piperidylcarbamoyloxy)crotonanilide
3'-(piperidylcarbamoyloxy)methacrylanilide
3'-(N-(2-methylpiperidyl)carbamoyloxy)crotonanilide
3'-(N-(2,6-dimethylpiperidyl)carbamoyloxy)methacrylanilide
3'-(N-(2,6-dimethylpiperidyl)carbamoyloxy)acrylanilide
3'-(N-isobutylcarbamoyloxy)cyclopropylcarboxanilide
3'-(N-(1,2-diethylbutyl)carbamoyloxy)cyclopropylcarboxanilide
3'-(N-n-propylcarbamoyloxy)cyclopropylcarboxanilide
3'-(N,N-diallycarbamoyloxy)cyclopropylcarboxanilide
3'-(N-allylcarbamoyloxy)cyclopropylcarboxanilide
3'-(N-(1-methyl-2-methoxyethyl)carbamoyloxy)cyclopropylcarboxanilide
3'-(N-(alpha-isopropylbenzyl)carbamoyloxy)cyclopropylcarboxanilide
3'-(N-(1,1-dimethyl-2-phenylethyl)carbamoyloxy)cyclopropylcarboxanilide
3'-(N-(4-methoxybenzyl)carbamoyloxy)cyclopropylcarboxanilide
3'-(N-(2-phenylethyl)carbamoyloxy)cyclopropylcarboxanilide
3'-(N-(alpha-t-butyl-4-methoxybenzyl)carbamoyloxy)cyclopropylcarboxanilide
3'-(N-(2-fluorophenyl)carbamoyloxy)cyclopropylcarboxanilide
3'-(N-allyl-N-(2-phenylethyl)carbamoyloxy)cyclopropylcarboxanilide
3'-(N-(4-methylbenzyl)carbamoyloxy)cyclopropylcarboxanilide
3'-(N-diphenylmethylcarbamoyloxy)cyclopropylcarboxanilide
3'-(N-(1-phenyl-n-butyl)carbamoyloxy)cyclopropylcarboxanilide 3'-(N-(alpha-methyl-4-chlorophenyl)carbamoyloxy)cyclopropylcarboxanilide
3'-(N,N-diphenylcarbamoyloxy)cyclopropylcarboxanilide
3'-(N-methyl-N-phenylcarbamoyloxy)cyclopropylcarboxanilide
3'-(N-methyl-N-(2-methyl-6-t-butylphenyl)carbamoyloxy)cyclopropylcarboxanilide
3'-(N-isopropyl-N-phenylcarbamoyloxy)cyclopropylcarboxanilide
3'-(N-methyl-N-(2,6-dimethylphenyl)carbamoyloxy)cyclopropylcarboxanilide
3'-(N-(4-5-butylphenyl)carbamoyloxy)cyclopropylcarboxanilide
3'-(N-(2,6-diethylcyclohexyl)carbamoyloxy)cyclopropylcarboxanilide
3'-(N-cyclohexylcarbamoyloxy)cyclopropylcarboxanilide
3'-(2,6-piperidylcarbamoyloxy)cyclopropylcarboxanilide
3'-(piperidylcarbamoyloxy)cyclopropylcarboxanilide
3'-(N-methylcarbamoyloxy)dichloroacetanilide
3'-(N-methylcarbamoyloxy)2,2-dichloropropionanilide
3'-(N-n-butylcarbamoyloxy)2,2-dichloropropionanilide
3'-(N-(2-ethylhexyl)carbamoyloxy)2,2-dichloropropionanilide
3'-(N-t-butylcarbamoyloxy)2,2-dimethyl-3,3-dichloropropionanilide
3'-(N,N-dimethylcarbamoyloxy)benzoanilide
3'-(N-(1-methyl-2-phenylethyl)carbamoyloxy)cyclopropylcarboxanilide
'3'-(N-(1-methylheptyl)carbamoyloxy)cyclopropylcarboxanilide
3'-(N-allylcarbamoyloxy)crotonanilide
3'-(N-allylcarbamoyloxy)acrylanilide
3'-(N-allylcarbamoyloxy)2-methylpropionthionanilide
3'-(N,N-dimethylcarbamoylthio)butyrthioanilide
3'-(N-t-butylthiocarbamoylthio)butyrthioanilide
3'-(N,N-diethylcarbamoyloxy)-N'-(methoxy)butyrthioanilide
3'-(N,N-dimethylcarbamoyloxy)-N'-(hexyloxy)-2-methylpropionanilide
3'-(N,N-allylcarbamoyloxy)-N'-(decyloxy)butyranilide
3'-(N-benzyl-N-methylthiocarbamoyloxy)-N'-(1-ethyloctyloxy)propionanilide
3'-(N-isobutylcarbamoyloxy)-N'-(duodecyloxy)-2-methylvaleranilide
3'-(N-isopropylcarbamoyloxy)-N'-(1-methyl-7-methyloctyloxy)acetanilide
3'-(N-cyclohexyl-N-methylcarbamoyloxy)-N'-(2-hepteneoxy)-3,3-dichloropropionthioanilide
3'-(N-piperidinylcarbamoyloxy)-N'-(allyloxy)-3,4,4-trichlorobutyrthioanilide
3'-(N-3,4-dimethylcyclopentylcarbamoylthio)-N'-(2-propyneoxy)benzoanilide
3'-(N-pentylcarbamoyloxy)-N'-(2-pentyneoxy)2-phenylacetanilide
3'-(N-allyl-N-methylcarbamoyloxy)-N'-(4-methyl-2-pentyneoxy)-2-methylbutyranilide
3'-(N-phenyl-N-methylcarbamoyloxy)N'-(acetyl)2,4-dichlorobenzoanilide
3'-(N-2,6-cyclohexylcarbamoyloxy)N'-(2,2-dimethylhexoyl)3-pentynoanilide 3'-(N,N-dimethylcarbamoyloxy)N'-(2,2,4-trimethyldecoyl)-5-methyl-3-hexynoanilide
3'-(N-ethylcarbamoyloxy)-N'-(methacryloyl)acetanilide
3'-(N-methylcarbamoyloxy)-N'-(crotonoyl)2''-methyl-4''-t-butylbenzanilide
3'-(N-methylcarbamoylthio)-N'-(4-methyl-2-pentenoyl)propionanilide
3'-(N-cyclohexylcarbamoyloxy)-N'-(2-methyl-2-heptenoyl)acetanilide
3'-(N-methylcarbamoyloxy)-N'-(2-butynoyl)acetanilide
3'-(N,N-dimethyl-carbamoyloxy)-N'-(4-methyl-2-hexynoyl)butyranilide
3'-(N-n-propylcarbamoyloxy)3,4-dimethylcyclopentyl carboxanilide
3'-(N,N-dimethylthiocarbamoylthio)N-(ethyl)thiopropionanilide
3'-(N-allylcarbamoyloxy)-N-(isopropyl)acetanilide
3'-(N-cyclohexylcarbamoyloxy)2,6-diethylcyclohexylcarboxanilide
3'-(N-isopropylcarbamoylthio)-N-(methyl)thiopropionanilide
3'-(N-methylcarbamoyloxy)cyclopropylthiocarboxanilide
3'-(N-ethylcarbamoyloxy)cycloheptylthiocarboxanilide
3'-(N-ethylthiocarbamoylthio)-N-(allyl)acetanilide
3'-(N-2,2-dichlorothylcarbamoyloxy)2-t-butyl-4-(p-methylphenyl)butyranilide
3'-(N-ethylcarbamoylthio)-N-(2-methyl-2-propenyl)propionanilide
3'-(N-1,1-dimethylpentylcarbamoyloxy)3-ethoxypropionanilide
3'-(N-ethylcarbamoyloxy)5-(ethoxymethoxy)valeranilide
3'-(N-isobutylcarbamoyloxy)-N'-(methyl)-3-methoxy-4-ethoxybutyranilide
3'-(N-methyl-N-isopropylcarbamoyloxy)3-allyloxypropionanilide
3'-(N,N-dimethylcarbamoyloxy)-N'-(2-n-propoxyethyl)propionanilide
3'-(N-n-propylcarbamoyloxy)-N'-[3-(2-methoxyethoxy)propyl]acetanilide
3'-(N-t-butylcarbamoyloxy)-N'-[2-(butoxymethoxy)ethyl]thiopropionanilide
3'-(N-isobutylcarbamoyloxy)-N'-(allyloxymethyl)valeranilide
3'-(N-ethylcarbamoyloxy)-N'-[4-(2-allyloxyethoxy)butyl]acetanilide
3'-(N-ethylcarbamoyloxy)-N'-(methyl)2-(2''-carboxyphenyl)thioacetanilide
3'-(N,N-dimethylthiocarbamoyloxy)2,2-dichloromethyl-3-phenylpropionanilide
3'-(N-methylcarbamoylthio)N'-(ethyl)-2-(4''-methoxyphenyl)acetanilide The following amido-amides were prepared by substantially the same procedure as previously shown. A C═S group will be referred to as "thioamido" such as "propionthioamido" except for the sulfur analog of acetamido is named "thioacetamido". The nitrogen atom of the amido group will be represented by N and the nitrogen atom of the anilide group will be N'.

3'-(2,2-dimethyl-4-pentanamido)-2,2-dimethylpropionanilide
3'-(2,2-dimethyl-3-vinyl-3-phenylpropionamido)-propionanilide
3'-(2,2,4-trimethylvaleramido)-formanilide 3'-(2-methyl-2-chloromethyl-3,3-dichloropropionamido)-propionanilide
3'-(2,2-di-chloromethylpropionamido)-propionanilide
3'-[2,2-dimethyl-3-(p-chlorophenyl)propionamido]-cyclopropylcarboxanilide
3'-(2,2-dimethylmyristamido)cyclopropylcarboxanilide
3'-(2,2-dimethyl-5-phenylvaleramido)cyclopropylcarboxanilide
3'-(2,2,3-trimethyl-4-pentenamido)cyclopropylcarboxanilide
3'-(2,2-dimethyl-4-hexenamido)cyclopropylcarboxanilide
3'-(2,2-dimethylundecanamido)cyclopropylcarboxanilide
3'-[2,2-dimethyl-3-(3,4-dichlorophenyl)propionamido]cyclopropylcarboxanilide
3'-[2,2-dimethyl-3-(2,6-dichlorophenyl)propionamido]cyclopropylcarboxanilide
3'-[2,2-dimethyl-3-phenyl-4-pentenamido]cyclopropylcarboxanilide
3'-(2,2-dimethylheptanamido)cyclopropylcarboxanilide
3'-(propionamido)cyclopropylcarboxanilide
3'-(2,2-dimethylmyristamido)2,2-dimethylpropionanilide
3'-(2,2,4-trimethyl-4-pentenamido)2-methylvaleranilide
3'-(3,3-dimethylbutyramido)2,2-dimethylpropionanilide
3'-(2,2-dimethyl-3-chloropropionamido)2,2-dimethylvaleranilide
3'-[2,2-dimethyl-3-(4-chlorophenyl)propionamido]2,2-dimethylpropionanilide
3'-(2,2-dimethylmyristamido)2,2-dimethylvaleranilide
3'-(2,2,3-trimethyl-4-pentenamido)propionanilide
3'-(2,2-dimethyllauramido)2,2-dimethylvaleranilide
3'-(2,2,3-trimethyl-4-pentenamido)2,2-dimethylpropionanilide
3'-(2,2,3-trimethyl-4-pentenamido)2,2-dimethylvaleranilide
3'-(2,2,4-trimethyl-4-pentenamido)2,2-dimethylvaleranilide
3'-(2,2-dimethyl-4-hexenamido)2-methylvaleranilide
3'-(2,2-dimethyl-4-hexenamido)2-methylpropionanilide
3'-(2,2-dimethyl-3-(2-chlorophenyl)propionamido)2,2-dimethylpropionanilide
3'-(2,2-dimethylundecanamido)2-methylpropionanilide
3'-(2,2-dimethyl-3-(2,6-dichlorophenyl)propionamido)2,2-dimethylpropionanilide
3'-(2,2-dimethyl-3-(3,4-dichlorophenyl)propionamido)2,2-dimethylvaleranilide
3'-(2,2-dimethyl-3-phenyl-4-pentenamido)2,2-dimethylvaleranilide
3'-(2,2-dimethylcapramido)-2-methylpropionanilide
3'-(2,2-dimethylcaprylamido)2-methylvaleranilide
3'-(2,2-dimethylheptanamido)propionanilide
3'-(2-methyl-2-n-propyl-4-pentenamido)2,2-dimethylpropionanilide
3'-(2,2-dimethylpropionamido)2,2,4-trimethylvaleranilide
3'-(2-methylvaleramido)2,2,4-trimethylvaleranilide
3'-(cyclopropylcarboxamido)2,2-dimethylvaleranilide
3'-(2-carboxybenzamido)propionanilide
3'-(2-methylvaleramido)propionthioanilide
3'-(propionamido)2,2-dimethyl-3,3-dichloropropionanilide
3'-(propionamido)2-chloromethyl-2-dichloromethylpropionanilide
3'-(2,2-dimethyl-3-chloropropionamido)2,2-dimethyl-3-chloropropionanilide
3'-(2,2-dimethyl-3,3-dichloropropionamido)2,2-dimethyl-3,3-dichloropropionanilide
3'-(N-methoxybutyrthioamido)-N'-(methoxy)benzanilide
3'-(N-hexoxy-2-methylpropionamido)-N'-(hexoxy)propionanilide
3'-(N-decoxybutyramido)-N'-(allyloxymethyl)butyranilide
3'[N-(1-ethyloctoxy)propionamido]-N'-(hexoxy)cyclohexylthioanilide
3'-(N-dodecoxy-1-methylbutyramido)-N'-(n-hexyl)2,2-dimethylpropionthioanilide
3'-[N-(1,2,7-trimethyloctoxy)acetamido]-N'-(acetyl)2,2-dimethylbutyranilide
3'-[N-(2-heptenoxy)3,3-dichloropropionthioamido]-N'-(allyl)-3-butenthioanilide
3'[N-(allyloxy)-3,4,4-trichlorobutyrthioamido]-N'-(2-methoxyethoxymethyl)propionanilide
3'-[N-(2-propynoxy)benzamido]-N'-(allyl)propionanilide
3'-[N-(2-pentynoxy)2-phenylacetamido]-N'-(ethyl)-3-pentynanilide
3'-[N-(4-methyl-2-pentynoxy)-2-methylbutyramido]-2-methylvalerthioanilide
3'-[N-(acetyl)2,4-dichlorobenzamido]-N'-(acetyl)2,2-dimethyl-3-(2'',4''-dimethylphenyl)propionanilide
3'-[N-(2,2-dimethylcaproyl)3-pentynamido]-N'-(methoxy)-2-n-propoxyacetanilide
3'-[N-(2,2,4-trimethylcapryl)5-methyl-3-hexynamido]-2,2-dimethylphenylpropionanilide
3'[N-(methacryl)acetamido]-N'-(methoxymethyl)3-butenthioanilide
3'-[N-(crotonyl)2-methyl-4-t-butylbenzamido]-N'-(crotonyl)-2-methyl-4-t-butylbenzanilide
3'-[N-(4-methyl-2-hexanoyl)propionamido]-N'(4-methyl-2-hexenoyl)propionanilide
3'-[N-(2-methyl-2-heptenoyl)acetamido]-propionthioanilide
3'-[N-(22-butynoyl)acetamido]-N'-(n-propyl)2,2-dimethylvaleranilide
3'-[N-(4-ethyl-2-pentynoyl)butyramido]-N'-methoxybutyranilide
3'-(3,4-dimethylcyclopentylcarboxamido)-N'-(alloxymethyl)-2-chloroacetanilide
3'-[N-(ethyl)propionthioamido]-N'-(2-allyloxy-4-ethoxybutyl)cyclopropylcarboxanilide
3'-[N-(1-propyl)acetamido]-N'-(dodecoxy)cyclopropylthiocarboxanilide
3'-(2,6-diethylcyclohexyl)-N'-(4-ethyl-2-pentynoyl)-2-methyl butyranilide
3'-[N-(methyl)propionthioamido]-N'-(2-butynoyl)-thioacetanilide
3'-(cyclopropylthiocarboxamido)-N'-(2-methyl-2-heptenoyl)-2,2-di-chloromethylpropionanilide
3'-(cycloheptylthiocarboxamido)-N'-(allyl3'',4''-dichlorobenzthioanilide 3'-[N-(allyl)acetamido]-N'-(allyl)cyclopropylcarboxanilide
3'-(2-t-butyl-5-(4-methylphenyl)valeramido)-N'-(allyloxymethyl)-2-methylvaleranilide
3'-[N'-(methallyl)propionamido]-N'-(ethyl)3-ethoxypropionanilide
3'-(3-ethoxypropionamido)-N'-(allyl)2-(2''-methyl-4''-t-butylphenyl)acetanilide
3'-[4-(ethoxymethoxy)butyramido]-N'-(ethyl)-2(2'',4''-dimethoxyphenyl)acetanilide
3'-[N-(methyl)3-methoxy-4-ethoxybutyramido]2,2-di-chloromethylacetanilide
3'-(3-allyloxypropionamido)-N'-(i-propyl)crotonthioanilide
3'-[N-(2-n-propoxyethyl)propionamido]-N'-(hexyl)-2,2-dimethyl-3(3'',4''-dichlorophenyl)propionanilide
3'-[N-(3-(2-methoxyethoxy)propyl)thioacetamido]-N'-(2-pentenoxymethyl)-2-vinyl-2-methyl-3-phenylpropionanilide
3'-[N-(2-butoxymethoxyethyl)propionthioamido]-N'-methylbenzanilide
3'-[N-(allyloxymethyl)valeramido]-N'-methoxymethyl-2-t-butyl-3-phenylpropionanilide
3'-[N-(4-(2-allyloxyethoxy)-n-butyl)acetamido]-N'-(methoxy)cyclohexylcarboxanilide
3'-[N-(allyl)-2-methyldodecanamido]-2''-methylbenzanilide
3'-[N-(i-propyl)-3-octenamido]N'-(2-methoxyethoxy)-2-methoxyacetanilide
3'-(2-methyl-3-heptenamido)-N'-(methyl)-2,2-dimethyl-3-phenylpropionanilide
3'-[N-(ethyl)2,5-dimethylhexenamido]-N'-(2-n-butoxymethoxyethyl)2,2-dimethyl-3-phenyl-4-pentenanilide
3'-[N-(ethyl)-2-butynamido]-N'-(acetyl)caproanilide
3'-(5-methyl-2-hexynamido)-N'-(methoxy)2,2-dimethylpropionanilide
3'-[N-(allyl)6-chlorohexanthioamido]-methyl-2-n-propyl-3-phenyl propionthioanilide
3'-[N-(methallyl)5,5-dichlorovaleramido]-N'-(methyl)-3-butenanilide
3'-[N-(hexyl)2-carboxybenzamido]-N'-(6-methylheptanoyl)-3-methoxy-4-ethoxybutyranilide
3'-[N-(ethyl)2,2-dimethyl-3-phenyl-4-pentenamido]-N'-(2-n-propoxy ethyl)2,2-diethylcyclohexylcarboxanilide
3'-(2-t-butyl-3-phenylpropionamido)-N'-(methallyl)-3,3-dimethylbutyranilide
3'-[N-(methoxymethyl)2,2-dimethyl-3-(3,4-dichlorophenyl)propionamido]2-methyldodecananilide
3'-[N-((3-methoxypropoxy)methyl)2,2-dimethyl-3-(4-methoxyphenyl]-N'-(acryl)2,2-dimethyl-3-phenylpropionanilide
3'-[N-(4-methyl-2-pentenoxy)3-(2,4-dimethylphenyl)propionamido]N'-(methyl)cyclopropylcarboxyanilide
3'-[N-(dodecoxy)2-(2-methyl-4-t-butylphenyl)acetamido]N'-(methyl)2,2,3-trimethyl-4-pentenanilide
3'-(2,2-di-chloromethyl-3-phenylpropionamido)-N'-N'-(propionoyl)2-(ethoxymethoxy)acetanilide
3'-[N-((2-methoxyethoxy)methyl)2-(2-carboxyphenyl)thioacetamido]N'-(ethoxy)2,2-dimethylvaleranilide 3'[N-(methyl)2-methyl-2-n-propyl-4-pentenamido]-cyclopropylcarboxanilide
3'-[N-(2-butynoyl)3,4-dichlorobenzamido]-N'-(methyl)2,2-dimethyltetradecananilide
3'-(crotonthioamido)-N'-(hexoxy)3,4,4-trichlorobutyrthioanilide
3'-[N-(propionoyl)3-chloropropionthioamido]-N'-(decoxy)2-phenyl thioacetanilide The following amido-carbanilates were prepared by substantially the same procedure as previously shown. Sulfur analogs of the carbanilate group will be represented as follows:

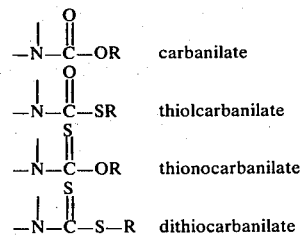

The nomenclature of the thioamido group and the nitrogen atom of the amido group will be as previously described. The nitrogen atom of the carbanilate group will be represented as N'.

n-propyl m-(acetamido)thiolcarbanilate
n-propyl m-(propionamido)thiolcarbanilate
phenyl m-(propionamido)thiolcarbanilate
methyl m-(acetamido)thiolcarbanilate
ethyl m-(acetamido)thiolcarbanilate
n-propyl m-(acetamido)thionocarbanilate
allyl m-(propionamido)dithiocarbanilate
methyl m-(2-methylpropionamido)dithiocarbanilate
methyl m-(2,2-dimethylpropionamido)dithiocarbanilate
isopropyl m-(acetamido)thionocarbanilate
methyl m-(butyramido)dithiocarbanilate
phenyl m-(acetamido)thiolcarbanilate
2,4-dichlorobenzyl m-(2-methylpropionamido)dithiocarbanilate
2,4-dichlorobenzyl m-(butyramido)dithiocarbanilate
2,6-dichlorobenzyl m-(2-methylpropionamido)dithiocarbanilate
n-propyl m-(butyramido)dithiocarbanilate
n-butyl m-(butyramido)dithiocarbanilate
ethyl m-(butyramido)dithiocarbanilate
allyl m-(propionamido)carbanilate
allyl m-(acetamido)dithiocarbanilate
2-cyclohexenyl m-(2-methylpropionamido)dithiocarbanilate
methyl m-(2,2-dimethylvaleramido)thiolcarbanilate
ethyl m-(2,2-dimethylvaleramido)thiolcarbanilate
n-propyl m-(2,2-diemthylvaleramido)thiolcarbanilate
phenyl m-(2,2-dimethylvaleramido)thiolcarbanilate
ethyl m-(2,2-dimethylpropionamido)thiolcarbanilate
ethyl m-(2-methylvaleramido)thiolcarbanilate
ethyl m-(2-methylvaleramido)thionocarbanilate
i-propyl m-(2-methylvaleramido)thionocarbanilate
methyl m-(2-methylvaleramido)carbanilate
methyl m-(2,2-dimethylvaleramido)carbanilate
methyl m-(2,2,4-trimethylvaleramido)carbanilate
methyl m-(2-methylpropionamido)thiolcarbanilate
i-propyl m-(2-methylpropionamido)carbanilate
methyl m-(2-methylpropionamido)carbanilate n-propyl m-(propionamido)thionocarbanilate
i-propyl m-(propionamido)carbanilate
methyl m-(2-methyl valeramido)thiolcarbanilate
methyl m-(propionamido)thionocarbanilate
ethyl m-(propionamido)thiolcarbanilate
ethyl m-(2-methylpropionamido)thiolcarbanilate
methyl m-(cyclopropylcarboxamido)thiolcarbanilate
ethyl m-(cyclopropylcarboxamido)thiolcarbanilate
phenyl m-(cyclopropylcarboxamido)thiolcarbanilate
i-propyl m-[N-(i-propyl)2-chloroacetamido]carbanilate
methyl m-(2-methyl-2-n-propyl-4-pentenamido)carbanilate
methyl m-(2,2-dimethyl-3-phenyl-4-pentenamido)carbanilate
methyl m-(2,2-dimethyl-4-pentenamido)carbanilate
n-propyl m-(benzamido)thiolcarbanilate
methyl m-(benzamido)dithiocarbanilate
methyl m-(2-carboxybenzamido)carbanilate
i-propyl m-(2-methylpropionthioamido)-N'-(ethyl)dithiocarbanilate
n-pentyl m-(butyrthioamido)N'-(methyl)carbanilate
allyl m-(butyrthioamido)carbanilate
cyclohexyl m-[N-(methoxy)butyrthioamido]dithiocarbanilate
allyl m-[N-(n-hexoxy)2-methylpropionamido]carbanilate
1,2-dimethylhexyl m-[N-(decoxy)butyramido]carbanilate
methyl m-[N-(1-ethyloctoxy)propionamido]carbanilate
2-butenyl m-[N-(dodecoxy)2-methylvaleramido]carbanilate
cyclopentyl m-[N-(1,2,7-trimethyloctoxy)acetamido]carbanilate
1,2-dimethylbutyl m-[N-(2-heptenoxy)3,3-dichloropropionthioamido]carbanilate
cyclopropyl m-[N-(allyloxy)3,4,4-trichlorobutyrthioamido]carbanilate
methyl m-[N-(2-propynoxy)benzamido]-N'-(methyl)carbanilate
cyclopropyl m-[N-(2-pentynoxy)2-phenylacetamido]carbanilate
methyl m-[N-(4-methyl-2-pentynoxy)2-methylbutyramido]-N'-(ethyl)carbanilate
methyl m-[N-(acetyl)2,4-dichlorobenzamido]carbanilate
methyl m-[N-(2,2-dimethylcaproyl)3-pentynamido]carbanilate
1,1-dimethylbutyl m-[N-)2,2,4-trimethyldecoyl)4-methyl-3-hexynamido]carbanilate
methyl m-[N-(methaeryl)acetamido]carbanilate
n-propyl m-[N-(crotonoyl)2-methyl-4-t-butylbenzamido]carbanilate
methyl m-[N-(4-methyl-2-pentenoyl)propionamido]carbanilate
ethyl m-[N-(2-methyl-2-heptenoyl)acetamido]carbanilate
n-propyl m-[N-(2-butynoyl)acetamido]carbanilate
methyl m-[N-(4-methyl-2hexynoyl)butyramido]carbanilate
phenyl m-(3,4-cyclopentylcarboxamido)carbanilate
benzyl m-[N-(ethyl)propionthioamido]carbanilate
4-methyl-2-pentenyl m-[N-(isopropyl)acetamido]-N'-(allyl)carbanilate
methyl m-(2,6-diethylcyclohexylcarboxamido)-N'-(t-butyl)carbanilate
4-nitrophenyl m-[N-(methyl)propionthioamido]thionocarbanilate
ethyl m-(cyclopropylcarboxthioamido)-N'-(3-methyl-2-butenyl)carbanilate
methyl m-(cyclohexylcarboxthioamido)carbanilate
allyl m-[N-(allyl)acetamido]carbanilate
methyl m-[2-t-butyl-4-(4-methylphenyl)butyramido]thiolcarbanilate
methyl m-[N-(methallyl)propionamido]carbanilate
2,4-dimethylphenyl m-(2-ethoxypropionamido)-N'-(4-methyl-2-pentenyl)carbanilate
isopropyl m-[5-(ethoxymethoxy)caproamido]carbanilate
1-chloromethyl-2-phenylethyl m-[N-(methyl)3-methoxy)4-ethoxy butyramido]dithiocarbanilate
t-butyl m-(3-allyloxypropionamido)carbanilate
1,1-dimethyl-2-phenyl-3-butenyl m-[N-(2-n-propoxyethyl)propionamido]-N'-(1,1-dimethylbutyl)carbanilate
cycloheptyl m-[N-(3-(2-methoxyethoxy)propyl)acetamido]carbanilate
n-butyl m-[N-(2-(n-butoxymethoxy)ethyl)propionthioamido]thiolcarbanilate
1,1-dimethyl-2-(2,4-dimethylphenyl)ethyl m-[N-(allyloxymethyl)valeramido]N'-(n-propyl)carbanilate
ethyl m-[N-(4-(2-allyloxyethoxy)butyl)acetamido]carbanilate
1,1-dimethyl-2-(2-methyl-4-t-butyl)ethyl m-[N-(methyl)2-(2-carboxyphenyl)thioacetamido]-N'-(methyl)thionocarbanilate
methyl m-(2,2-di-chloromethyl-2-phenylpropionamido)carbanilate
3,4-dichlorophenyl m-[N-(ethyl)2-(4-methoxyphenyl)acetamido]dithiocarbanilate The following amido-ureas were prepared by substantially the same procedure as previously shown.

The nomenclature of the thioamido group and the nitrogen atom of the amido group will be as previously described.

Sulfur analogs of the urea group will be referred to as thiourea.

1,1-di-n-butyl-3-[(3'-propionanilide)phenyl]thiourea
1,1-dimethyl-3[(3'-propionamido)phenyl]thiourea
1-t-butyl-3-[3'-(2,2-dimethyl-3,3-dichloropropionamido)phenyl]urea
1,1-dimethyl-3-[3'-(2-chloromethyl-2-dichloromethylpropionamido)phenyl]urea
1-t-butyl-3-[3'-(2,2-di-chloromethylproopionamido)phenyl]urea
1-methyl-1-n-butyl-3-[3'-(2-methyl-2-n-propyl-4-pentenamido)phenyl]urea
1,1-dimethyl-3-[3'-(2-methyl-2-n-propyl-4-pentenamido)phenyl]urea
1,1-dimethyl-3-[3'-(2,2-dimethyl-3-phenyl-4-pentenamido)phenyl]urea
1,1-diethyl-3-[3'-(2,2-dimethyl-[4-pentenamido)-phenyl]urea
1-t-butyl-3-[3'-(2,2-dimethyl-4-pentenamido)-phenyl]urea
1-t-butyl-3-[3'-(cyclopropylcarboxamido)phenyl]urea
1-phenyl-3-[3'-(cyclopropylcarboxamido)phenyl]thiourea
1-allyl-3-[3'-(cyclopropylcarboxamido)phenyl]thiourea 1,1-dimethyl-3-[3'-(cyclopropylcarboxamido)-phenyl]urea
1,1-dimethyl-3-[3'-(2,3,4,5-tetrachlorocarboxy-phenylamido)phenyl]urea
1,1-diethyl-3-[3'-(2-carboxyphenylamido)phenyl]urea
1-t-butyl-3-[3'-(2,2-dimethylcaprylamido)phenyl]urea
1-t-butyl-3-[3'-(caprylamido)phenyl]thiourea
1-t-butyl-3-[3'-(2,2,4-trimethylvaleramido)phenyl]thiourea
1-t-butyl-3-[3'-(2,2-dimethylpropionamido)phenyl]urea
1-(1,1,3,3-tetramethylbutyl)-3-[3'-(2-methylvaleramido)phenyl]urea
1,1-diethyl-3-[3'-(2,2,4-trimethylvaleramido)-phenyl]thiourea
1-(2-chloroallyl)-3-[3'-(2,2-dimethylvaleramido)-phenyl]thiourea
1-(2-chloroallyl)-3-[3'-(2,2,4-trimethylvaleramido)-phenyl]thiourea
1-allyl-3-[3'-(2,2-dimethylvaleramido)phenyl]thiourea
1-allyl-3-[3'-(2,2,4-trimethylvaleramido)phenyl]thiourea
1,1-di-n-propyl-3-[3'-(2,2-dimethylvaleramido)-phenyl]thiourea
1,1-di-n-propyl-3-[3'-(2,2,4-trimethylvaleramido)-phenyl]thiourea
1-methyl-1-n-butyl-3-[3'-(2,2-dimethylvaleramido)-phenyl]thiourea
1-methyl-1-n-butyl-3-[3'-(2,2,4-trimethylvaleramido)phenyl]thiourea
1-t-butyl-3-[3'-(propionamido)phenyl]thiourea
1-t-butyl-3-[3'-(2,2-dimethylpropionamido)phenyl]thiourea
1-t-butyl-3-[3'-(2-methylvaleramido)phenyl]thiourea
1-t-butyl-3-[3'-(2,2,4-trimethylvaleramido)phenyl]urea
1,1-diethyl-3-[3'-(caprylamido)phenyl]urea
1,1-diethyl-3-[3'-(2,2-dimethylvaleramido)phenyl]thiourea
1-(1-methylheptyl)-3-[3'-(2-methylvaleramido)-phenyl]urea
1-(2,6-diethylphenyl)-3-[3'-2-methylvaleramido)-phenyl]urea
1-(1,3-dimethylbutyl)-3-[3'-(2-methylvaleramido)-phenyl]urea
1-(2,6-diethylcyclohexyl)-3-[3'-(2-methylvaleramido)phenyl]urea
1,1-dimethyl-3-[3'-(2,2-dimethylvaleramido)phenyl]urea
1,1-diethyl-3-[3'-(2-methylvaleramido)phenyl]thiourea
1-pyrrolidinyl-3-[3'-(2-methylvaleramido)phenyl]-thiourea
1,1-dimethyl-3-[3'-(2-methylvaleramido)phenyl]thiourea
1-cyclohexyl-3-[3'-(2-methylvaleramido)phenyl]-urea
1-sec-butyl-3-[3'-(2-methylvaleramido)phenyl]urea
1-n-butyl-3-[3'-(2-methylvaleramido)phenyl]urea
1-(2-chloroallyl)-3-[3'-(2-methylvaleramido)-phenyl]thiourea
1-phenyl-3-[3'-(2-methylvaleramido)phenyl]urea
1-(3-chlorophenyl)-3-[3'-(2-methylvaleramido)-phenyl]urea
1-phenyl-3-[3'-(2-methylvaleramido)phenyl]urea
1-(2-chloroallyl)-3-[3'-propionamido)phenyl]urea
1-(4-chlorophenyl)-3-[3'-(Propionamido)phenyl]urea
1,1-diallyl-3-[3'-(2,2-dimethylpropionamido)-phenyl]urea
1-phenyl-3-[3'-(2-methylvaleramido)phenyl]thiourea
1-phenyl-3-[3'-(2,2-dimethylpropionamido)phenyl]thiourea
1-phenyl-3-[3'-(2-methylpropionamido)phenyl]thiourea
1-phenyl-3-[3'-(propionamido)phenyl]thiourea
1,1-diallyl-3-[3'-(propionamido)phenyl]thiourea
1-allyl-3-[3'-(2,2-dimethylpropionamido)phenyl]thiourea
1-allyl-3-[3'-(2-methylvaleramido)phenyl]thiourea
1-allyl-3-[3'-(2-methylpropionamido)phenyl]thiourea
1,1-dimethyl-3-[3'-(2,2-dimethylpropionamido)-phenyl]thiourea
1-methyl-1-methoxy-3-[3'-(2,2-dimethylpropionamido)phenyl]thiourea
1-methyl-1-methoxy-3-[3'-(propionamido)phenyl]thiourea
1,1-dimethyl-3-[3'-(2,2-dimethylpropionamido)-phenyl]thiourea
1-morpholinyl-3-[3'-(propionamido)phenyl]thiourea
1-methyl-1-n-butyl-3-[3'-(propionamido)phenyl]thiourea
1,1-di-n-propyl-3-[3'-(propionamido)phenyl]thiourea
1,1-diethyl-3-[3'-(propionamido)phenyl]thiourea
1-(3,4-dichlorophenyl)-3-[3'-(propionamido)-phenyl]thiourea
1-(2,6-diethylphenyl)-3-[3'-propionamido)phenyl]thiourea
1-allyl-3-[3'-propionamido)phenyl]thiourea
1,1-di-n-butyl-3-[3'-(propionamido)phenyl]thiourea
1-[3'-(propionamido)phenyl]thiourea
1-methyl-3-[3'-(propionamido)phenyl]urea
1-methyl-1-n-butyl-3-[3'-(2,2-dimethyl-3-(3,4-dichlorophenyl)propionamido)phenyl]urea
1,1-diethyl-3-[3'-(2,2-dimethyl-3-(3,4-dichlorophenyl)propionamido)phenyl]urea
1,1-dimethyl-3-[3'-(2,2-dimethyl-3-(3,4-dichlorophenyl)propionamido)phenyl]urea
1-t-butyl-3-[3'-(2,2-dimethyl-3-phenylpropionamido)phenyl]urea
1-methyl-3-[3'-(2,2-dimethylpropionamido)phenyl]thiourea
1-methyl-1-allyl-3-[3'-N-(methoxy)butyrthioamidophenyl]-3-allylurea
1-methyl-1-(1,1-di-chloromethyl-2-chloroethyl)-3-[3'-N-(hexoxy)-2-methylpropionamidophenyl]urea
1-methyl-1-(1,1-dimethyl-2-hexenyl)-3-[3'-N-(decoxy)butyramidophenyl]-3-n-propylurea
1-(2,2-di-chloromethyl-4-chlorobutyl)-3-[3'-N-(1-ethyloctoxy)propionthioamidophenyl]-3-ethylurea
1,1-dimethyl-3-[3'-N-(dodecoxy)-2-methyl-valeramidophenyl]-3-methylurea
1-(2,4,4-trichlorobutyl)-3-[3'-N-(1,2,7-trimethyloctoxy)acetamidophenyl]urea
1-methyl-1-n-propyl-3-[3'-N-(2-heptenoxy)3,3-dichloropropionthioamidophenyl]urea 1-(2,6-diethylpiperdinyl)-3-[3'-N-(allyloxy)3,4,4-trichlorobutyrthioamidophenyl]-3-methylthiourea 1-(pyrrolidinyl)3-[3'-N-(2-propynoxy)benzamidophenyl]urea 1-(benzyl)-3-[3'-N-(2-pentynoxy)2-phenylacetamidophenyl]-3-(1,1-dimethylhexyl)urea 1,1-diethyl-3-[3'-N-(4-methyl-2-pentynoxy)2-methylbutyramidophenyl]-3-methylurea 1-(1,1-dimethyl-2-phenyl-4-butenyl)-3-[3'-N-(acetyl)-2,4-dichlorobenzamidophenyl]urea 1-(n-propyl)-3-[3'-N-(2,2-dimethylcaproyl)3-butynamidophenyl]-3-methylurea 1,1-dimethyl-3-[3'-N-(2,2,4-trimethylpelargonoyl)-5-methyl-3-hexynamidophenyl]-3-(n-octyl)urea 1-methyl-1-(n-hexyl)-3-[3'-N-(methacryl)acetamidophenyl]-3-methylurea 1-ethyl-3-[3'-N-(crotonoyl)2-methyl-4-t-butylbenzamidophenyl]urea 1-(n-butyl)-3-[3'-N-(4-methyl-2-pentenoyl)propionamidophenyl]urea 1,1-diethyl-3-[3'-N-(2-methyl-2-heptenoyl)acetamidophenyl]-3-n-propylurea 1,1-dimethyl-3-[3'-N-(2-butynoyl)acetamidophenyl]urea 1-methyl-1-dodecyl-3-[3'-(3,4-dimethylpyrrolidinyl)carboxamidophenyl]-3-allylurea 1-(1,1,3,4-tetramethylpentyl)-3-[3'-N-(ethyl)propionthioamidophenyl]-3-(1,3-dimethyl-2-butenyl)thiourea 1-(1,1-dimethyldecyl)-3-[3'-N-(isopropyl)acetamidophenyl]-3-(3-methyl-2-butenyl)urea 1-methyl-1-n-propyl-3-[3'-(2,6-diethylcyclohexyl-carboxamidophenyl]urea 1-methyl-1-(2,4-dichlorophenyl)-3-[3'-(cycloheptylcarboxthioamidophenyl)]thiourea 1-methyl-1-t-butyl-3-[3'-N-(allyl)acetamidophenyl]urea 1,1-dimethyl-3-[3'-(2-t-butyl-2-(4-methylphenyl)acetamidophenyl]thiourea 1-methyl-1-methoxy-3-[3'-N-(methallyl)propionthioamidophenyl]-3-n-butylurea 1,1-dimethyl-3-[3'-(3-ethoxypropionamido)]-3-methylthiourea 1-(4-nitrophenyl)-3-[3'-(2-methyl-2-(isopropoxymethoxy)acetamidophenyl]-3-methylurea 1,1-dihexyl-3-[3'-N-(methyl)-3-methoxy-4-ethoxybutyramidophenyl]-3-n-propylurea 1-n-propoxy-3-[3'-(2-allyloxypropionamidophenyl)-]urea 1,1-diethyl-3-[3'-N-(2-n-propoxyethyl)propionamidophenyl]-3-(2,5-dimethylhexyl)urea 1-methyl-1-(1,1,3-trimethyl-2-butenyl)-3-[3'-N-[3-(2-methoxyethoxy)propyl]acetamidophenyl]urea 1-n-propyl-3-[3'-N-(2-(butoxymethoxy)ethyl)propionthioamidophenyl]-3-ethylurea 1-(1-methyl-2,5-dichloro-2-pentenyl)-3-[3'-N-(allyloxymethyl)valeramidophenyl]-3-methylurea 1-n-hexoxy-3-[3'-N-(4-(2-allyloxyethoxy)n-butyl)-acetamidophenyl]urea 1,1-dimethyl-3-[3'-N-(methyl)-2-(2-carboxyphenyl)thioacetamido]-3-allylurea 1-(2,4,4-trichloro-2-butenyl)-3-[3'-(2,2-dichloromethyl-2-phenyl)acetamidophenyl]urea 1-(3-methyl-2-butenyl)-3-[3'-N-(ethyl)-2-(4-methoxyphenyl)acetamidophenyl]-3-(1,1,3-trimethylpentyl)urea 1-methyl-1-n-propyl-3-[3'-N-(methyl)-2-t-butyl-3-phenylpropionamido]thiourea While the present compounds are useful exposing fungicides, nematocides, bactericides, bacteriostats and fungistats, their most outstanding characteristic is the regulation of plant growth. In accordance with this invention it has been found that the growth of dormant seeds, germinant seeds, germinative seeds, emerging seedlings, established woody and herbaceous vegetation and aquatic plants can be modified by exposing the seeds, emerging seedlings, or the roots or above-ground portions of established vegetation, or the aquatic plants to the action of an effective amount of the compounds of the present invention. The compounds can be used as individual compounds, as admixtures of two or more compounds, or in admixture with an adjuvant. These compounds are effective as general plant growth regulants, including postemergent phytotoxicants and pre-emergent phytotoxicants, but their most outstanding utility is as selective pre-emergent and post-emergent phytotoxicants, e.g. the selective control of the growth of one or more monocotyledonous species and/or one or more dicotyledonous species in the presence of other monocotyledons and/or dicotyledons. Furthermore, these compounds are characterized by broad spectrum activity; i.e. they modify the growth of a wide variety of plants including but not limited to ferns, conifers (pine, fir and the like), aquatic, monocotyledons and dicotyledons.

For the sake of brevity and simplicity, the term "active ingredient" will be used hereinafter to describe the present 3'-(carbamoyloxy)anilides; amidoanilides; amido-ureas and amidocarbanilates.

The plant growth regulant compositions of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The term "plant growth regulant composition" as used herein and in the appended claims is intended to mean not only compositions in a suitable form for application but also concentrated compositions which require dilution or extension with a suitable quantity of liquid or solid adjuvant prior to application.

The pre-emergent plant growth regulant activity of illustrative compounds of this invention is demonstrated as follows:

A good grade of top soil is placed in aluminum pans and compacted to a depth of three-eighth inch to one-half inch from the top of each pan. A predetermined number of seeds of each of various plant species are placed on top of the soil in each pan. The plant growth regulant compositions are applied to the soil by two methods: (1) application to the surface of the top soil layer and (2) admixture with or incorporation in the top soil layer.

In the surface application method the seeds are covered with a ⅜ inch layer of prepared soil and the pan leveled. The plant growth regulant composition is applied by spraying the surface of the top layer of soil, prior to watering the seeds, with a solution containing a sufficient amount of active ingredient to obtain the desired rate per acre on the soil surface.

In the soil incorporation method, the soil required to cover the seeds is weighed and admixed with a plant growth regulant composition containing a known amount of active ingredient. The pans are then filled with the admixture and leveled. Watering is carried out by permitting the soil in the pans to absorb moisture through the apertured bottom of the pans. The seed containing pans are placed on a wet sand bench and maintained for approximately 14 or 28 days under ordinary conditions of sunlight and watering. The plants are observed at the end of approximately 14 or 28 days and the results recorded.

The pre-emergent phytotoxic activity of the active ingredients is measured by the average percent control of each seed lot. The average percent control is converted to a relative numerical scale for the sake of brevity and simplicity in the examples. The pre-emergent phytotoxic activity index used in the Tables is defined as follows:

| Average Percent Control | | Numerical Scale |
|---|---|---|
| 0 – 25 | = | 0 |
| 26 – 50 | = | 1 |
| 51 – 75 | = | 2 |
| 76 – 100 | = | 3 |

The pre-emergent phytotoxic activity of some of the 3'-(carbamoyloxy)anilides of this invention is recorded in Table I for various application rates of the active ingredients in both surface and soil-incorporation applications. The terms "SA" and "SI" in the Comments column of Table I mean surface application method and soil incorporation method, respectively. The term (a) in the Comments column of Table I means that the phytotoxic activity was observed and recorded at the end of approximately 14 days. The term (b) in the Comments column of Table I means that the phytotoxic activity was observed and recorded at the end of approximately 28 days. In Table I the various plant species are represented by letters as follows:

| | |
|---|---|
| C — Morning Glory | O — Soybean |
| D — Wild Oats | P — Wild Buckwheat |
| E — Brome Grass | Q — Tomato |
| F — Rye Grass | R — Sorghum |
| G — Radish | S — Rice |
| H — Sugar Beets | T — Smartweed |
| I — Cotton | U — Cocklebur |
| J — Corn | V — Lambsquarter |
| K — Foxtail | W — Hemp sesbania |
| L — Barnyard Grass | X — Wheat |
| M — Crab Grass | Y — Velvet Leaf |
| N — Pigweed | |

TABLE I

PRE-EMERGENT PHYTOTOXIC ACTIVITY OF VARIOUS 3'-(CARBAMOYLOXY)ANILIDES

| Compound | Comments | Rate lbs./acre | C | D | E | F | G | H | I | J | K | L | M |
|---|---|---|---|---|---|---|---|---|---|---|---|---|---|
| N-isopropyl-3'-(methylcarbamoyloxy)-alpha-chloroacetanilide | SA(a) | 5 | 0 | 1 | 0 | 0 | 0 | 0 | — | — | 3 | — | 3 |
|  | SI(a) | 0.25 | — | 0 | 1 | — | — | 0 | 0 | 0 | — | 3 | 3 |
| N-isopropyl-3'-(t-butylcarbamoyloxy)-alpha-chloroacetanilide | SA(a) | 5 | 0 | 2 | 2 | 2 | 0 | 0 | — | — | 3 | — | 3 |
| 3'-(methylcarbamoyloxy)acetanilide | SA(a) | 10 | 0 | 0 | 1 | 0 | 0 | 1 | — | — | 0 | — | 1 |
| 3'-(methylcarbamoyloxy)propionanilide | SA(a) | 10 | 1 | 0 | 1 | 0 | 2 | 2 | — | — | 0 | — | 3 |
|  | SI(a) | 1 | — | 0 | 0 | — | — | 1 | 0 | 0 | — | 1 | 3 |
| 3'-(t-butylcarbamoyloxy)propionanilide | SA(b) | 10 | 2 | 2 | 2 | 2 | 3 | 3 | — | — | 3 | — | 3 |
|  | SI(b) | 0.25 | — | 0 | 0 | — | — | 0 | 0 | 0 | — | 0 | 0 |
| 3'-(ethylcarbamoyloxy)propionanilide | SA(b) | 10 | 3 | 2 | 3 | 2 | 2 | 3 | — | — | 3 | — | 3 |
|  | SI(b) | 1 | — | 1 | 0 | — | — | 0 | 0 | 0 | — | 1 | 3 |
| 3'-(isopropylcarbamoyloxy)propionanilide | SA(b) | 10 | 2 | 2 | 2 | 3 | 2 | 3 | — | — | 3 | — | 3 |
|  | SI(b) | 1 | — | 0 | 2 | — | — | 3 | 0 | 1 | — | 1 | 0 |
| 3'-(n-butylcarbamoyloxy)propionanilide | SA(a) | 10 | 1 | 1 | 1 | 0 | 3 | 1 | — | — | 1 | — | 3 |
| 3'-(phenylcarbamoyloxy)propionanilide | SA(a) | 10 | 0 | 0 | 1 | 1 | 2 | 1 | — | — | 0 | — | 2 |
| 3'-(m-chlorophenylcarbamoyloxy)propionanilide | SA(a) | 10 | 0 | 0 | 0 | 0 | 0 | 0 | — | — | 0 | — | 0 |
| 3'-(cyclohexylcarbamoyloxy)propionanilide | SI(a) | 1 | — | 0 | 1 | — | — | 1 | 1 | 0 | — | 2 | 2 |
| 3'-(dimethylcarbamoyloxy)propionanilide | SA(a) | 10 | 2 | 0 | 0 | 0 | 0 | 3 | — | — | 3 | — | 3 |
| 3'-(methylcarbamoyloxy)-2-methylpropionanilide | SA(a) | 10 | 1 | 0 | 1 | 0 | 1 | 1 | — | — | 3 | — | 3 |
| 3'-(n-propylcarbamoyloxy)-2-methylpropionanilide | SI(a) | 1 | — | 0 | 0 | — | — | 1 | 0 | 0 | — | 1 | 3 |
| 3'-(methylcarbamoyloxy)-2-methylvaleranilide | SA(b) | 10 | 3 | 1 | 2 | 0 | 3 | 3 | — | — | 3 | — | 3 |
|  | SI(b) | 1 | — | 1 | 1 | — | — | 2 | 0 | 0 | — | 1 | 3 |
| 3'-(n-propylcarbamoyloxy)-2-methylvaleranilide | SI(a) | 0.25 | — | 0 | 0 | — | — | 1 | 1 | 1 | — | 1 | 3 |
| 3'-(t-butylcarbamoyloxy)-2-methylvaleranilide | SI(a) | 0.25 | — | 0 | 0 | — | — | 3 | 0 | 0 | — | 2 | 3 |
| 3'-(n-butylcarbamoyloxy)-2-methylvaleranilide | SA(a) | 10 | 0 | 0 | 0 | 0 | 0 | 0 | — | — | 0 | — | 2 |
| 3'-(1,1,3,3-tetramethylbutylcarbamoyloxy)propionanilide | SI(b) | 1 | — | 0 | 0 | — | — | 0 | 0 | 1 | — | — | 0 |
| 3'-(1,1,3,3-tetramethylbutylcar- | | | | | | | | | | | | | |

TABLE I-continued
PRE-EMERGENT PHYTOTOXIC ACTIVITY OF VARIOUS 3'-(CARBAMOYLOXY)ANILIDES

| Compound | Comments | Rate lbs./acre | | | | | | | | | | |
|---|---|---|---|---|---|---|---|---|---|---|---|---|
| bamoyloxy)-2-methylpropionanilide | SI(b) | 1 | — | 0 | 0 | — | — | 0 | 1 | 0 | — | 0 | 0 |
| 3'-(isopropylcarbamoyloxy)-propionanilide | SI(b) | 1 | — | 0 | 0 | — | — | 0 | 2 | 0 | — | 2 | 0 |
| 3'-(methylcarbamoyloxy)acrylanilide | SA(a) | 0.25 | — | 0 | 0 | — | — | 0 | 0 | 0 | — | 0 | 0 |
| 3'-(methylcarbamoyloxy)cyclopropylcarboxanilide | SI(b) | 1 | — | 0 | 0 | — | — | 2 | 2 | 0 | — | 0 | 0 |
| 3'-(t-butylcarbamoyloxy)cyclopropylcarboxanilide | SI(b) | 1 | — | 2 | 3 | — | — | 3 | 1 | 2 | — | 3 | 3 |
| 3'-(1,1,3,3-tetramethylbutylcarbamoyloxy)-2-methylacrylanilide | SI(b) | 1 | — | 0 | 1 | — | — | 0 | 0 | 0 | — | 0 | 0 |
| 3'-(diethylcarbamoyloxy)propionanilide | SA(a) | 10 | 0 | 1 | 0 | 1 | 3 | 3 | — | — | 3 | — | 3 |
| 3'-(t-butylcarbamoyloxy)-2-methylacrylanilide | SI(b) | 1 | — | 0 | 1 | — | — | 3 | 0 | 1 | — | 0 | 3 |
| 3'-(cyclohexylcarbamoyloxy)-2-methylacrylanilide | SI(b) | 1 | — | 0 | 3 | — | — | 2 | 1 | 0 | — | 0 | 0 |
| 3'-(n-propylcarbamoyloxy)-2-methylacrylanilide | SI(b) | 0.25 | — | 0 | 3 | — | — | 2 | 3 | 0 | — | 0 | 1 |

| Compound | Comments | Rate lbs./acre | Plant | | | | | | | | | | |
|---|---|---|---|---|---|---|---|---|---|---|---|---|---|
| | | | N | O | P | Q | R | S | T | U | V | W | X | Y |
| N-isopropyl-3'-(methylcarbamoyloxy)-alpha-chloroacetanilide | SA(a) | 5 | 3 | 0 | 0 | 0 | 1 | — | — | — | — | — | — | — |
|  | SI(a) | 0.25 | 0 | 0 | — | — | — | 0 | 0 | 0 | 0 | 0 | 0 | 0 |
| N-isopropyl-3'-(t-butylcarbamoyloxy)-alpha-chloroacetanilide | SA(a) | 5 | — | 0 | 3 | 0 | 3 | — | — | — | — | — | — | — |
| 3'-(methylcarbamoyloxy)acetanilide | SA(a) | 10 | 3 | 0 | 0 | 0 | 1 | — | — | — | — | — | — | — |
| 3'-(methylcarbamoyloxy)propionanilide | SA(a) | 10 | 3 | 0 | 0 | 3 | 0 | — | — | — | — | — | — | — |
|  | SI(a) | 1 | 3 | 0 | — | — | — | 1 | 3 | — | 3 | 1 | 0 | 1 |
| 3'-(t-butylcarbamoyloxy)propionanilide | SA(b) | 10 | 3 | 3 | 3 | 3 | 2 | — | — | — | — | — | — | — |
|  | SI(b) | 0.25 | 3 | 0 | — | — | — | 0 | 3 | 0 | 0 | 3 | 0 | 3 |
| 3'-(ethylcarbamoyloxy)propionanilide | SA(b) | 10 | 3 | 2 | 3 | 3 | 3 | — | — | — | — | — | — | — |
|  | SI(b) | 1 | 3 | 0 | — | — | — | 1 | 3 | — | 2 | 3 | 0 | 3 |
| 3'-(isopropylcarbamoyloxy)-propionanilide | SA(b) | 10 | 3 | 2 | 3 | 3 | 3 | — | — | — | — | — | — | — |
|  | SI(b) | 1 | 1 | 1 | — | — | — | 3 | 3 | — | 3 | 3 | 3 | 3 |
| 3'-(n-butylcarbamoyloxy)propionanilide | SA(a) | 10 | 3 | 1 | 3 | 1 | 0 | — | — | — | — | — | — | — |
| 3'-(phenylcarbamoyloxy)propionanilide | SA(a) | 10 | 3 | 0 | 3 | 1 | 0 | — | — | — | — | — | — | — |
| 3'-(m-chlorophenylcarbamoyloxy)-propionanilide | SA(a) | 10 | 3 | 0 | 0 | 0 | 0 | — | — | — | — | — | — | — |
| 3'-(cyclohexylcarbamoyloxy)-propionanilide | SI(a) | 1 | 3 | 0 | — | — | — | 0 | 3 | — | 2 | 3 | 0 | 3 |
| 3'-(dimethylcarbamoyloxy)-propionanilide | SA(a) | 10 | 3 | 0 | 2 | 1 | 0 | — | — | — | — | — | — | — |
| 3'-(methylcarbamoyloxy)-2-methylpropionanilide | SA(a) | 10 | 3 | 1 | 0 | 1 | 1 | — | — | — | — | — | — | — |
| 3'-(n-propylcarbamoyloxy)-2-methylpropionanilide | SI(a) | 1 | 3 | 0 | — | — | — | 0 | 3 | — | 3 | 3 | 0 | 3 |
| 3'-(methylcarbamoyloxy)-2-methylvaleranilide | SA(b) | 10 | 3 | 2 | 3 | 3 | 3 | — | — | — | — | — | — | — |
|  | SI(b) | 1 | 3 | 0 | — | — | — | 0 | 3 | — | 3 | 2 | 0 | 3 |
| 3'-(n-propylcarbamoyloxy)-2-methylvaleranilide | SI(a) | 0.25 | 2 | 0 | — | — | — | 0 | 2 | — | 3 | 2 | 0 | 0 |
| 3'-(t-butylcarbamoyloxy)-2-methylvaleranilide | SI(a) | 0.25 | 3 | 0 | — | — | — | 1 | 3 | 0 | 3 | 2 | 0 | 3 |
| 3'-(n-butylcarbamoyloxy)-2-methylvaleranilide | SA(a) | 10 | 3 | 1 | 0 | 0 | 0 | — | — | — | — | — | — | — |
| 3'-(1,1,3,3-tetramethylbutylcarbamoyloxy)propionanilide | SI(b) | 1 | 2 | 0 | — | — | — | 1 | 3 | 0 | 3 | 3 | 0 | 3 |
| 3'-(1,1,3,3-tetramethylbutylcarbamoyloxy)-2-methylpropionanilide | SI(b) | 1 | 0 | 0 | — | — | — | 1 | 1 | 0 | 3 | 3 | 0 | 3 |
| 3'-(isopropylcarbamoyloxy)-propionanilide | SI(b) | 1 | 3 | 0 | — | — | — | 2 | 2 | 0 | 2 | 3 | 0 | 3 |
| 3'-(methylcarbamoyloxy)acrylanilide | SA(a) | 0.25 | 0 | 0 | — | — | — | 0 | 3 | 0 | 0 | 3 | 0 | 0 |
| 3'-(methylcarbamoyloxy)cyclopropylcarboxanilide | SI(b) | 1 | 3 | 0 | — | — | — | 0 | 1 | 0 | 3 | 0 | 0 | 2 |
| 3'-(t-butylcarbamoyloxy)cyclopropylcarboxanilide | SI(b) | 1 | 3 | 1 | — | — | — | 3 | 3 | 3 | 3 | 3 | 0 | 3 |
| 3'-(1,1,3,3-tetramethylbutylcarbamoyloxy)-2-methylacrylanilide | SI(b) | 1 | 2 | 0 | — | — | — | 0 | 1 | 0 | 1 | 3 | 0 | 3 |
| 3'-(diethylcarbamoyloxy)propionanilide | SA(a) | 10 | 3 | 0 | 2 | 0 | 1 | — | — | — | — | — | — | — |
| 3'-(t-butylcarbamoyloxy)-2-methylacrylanilide | SI(b) | 1 | 3 | 0 | — | — | — | 1 | 3 | 0 | 3 | 3 | 0 | 3 |
| 3'-(cyclohexylcarbamoyloxy)-2-methylacrylanilide | SI(b) | 1 | 2 | 0 | — | — | — | 1 | 2 | 0 | 0 | 0 | 0 | 3 |
| 3'-(n-propylcarbamoyloxy)-2-methylacrylanilide | SI(b) | 0.25 | 3 | 0 | — | — | — | 0 | 1 | 0 | 0 | 3 | 0 | 1 |

While carrying out the above and other pre-emergent tests with 3'-(carbamoyloxy)anilides, numerous specific plant growth responses were observed and recorded. Some of the observed plant growth responses are given in Table II.

TABLE II

| Compound | Rate Lbs./Acre | Response |
|---|---|---|
| 3'-(methylcarbamoyloxy)-propionanilide | 5 | Stunting of broadleaf species. |
| 3'-(methylcarbamoyloxy)-2-methylpropionanilide | 1 | Stunting of grass and broadleaf species |
| 3'-(isopropylcarbamoyloxy)-propionanilide | 1 | Barnyard grass stunted. |
| 3'-(t-butylcarbamoyloxy)-2-methylpropionanilide | 10 | Morning glory stunted. |
| 3'-(n-propylcarbamoyloxy)-2-methylvaleranilide | 0.25 | Chlorosis of lambsquarter and hemp sesbania. |
| 3'-(n-butylcarbamoyloxy)-2-methylacrylanilide | 10 | Desiccation of broadleaf species. |

The pre-emergent phytotoxic activity of 3'-(carbamoyloxy) anilides on perennial species is demonstrated as follows. The surface of soil containing vegetative propagules of Canada thistle, bindweed and horsenettle was sprayed with 3'-(cyclohexylcarbamoyloxy)propionanilide at an application rate of one pound of active ingredient per acre. At the end of 8 weeks each species was 100% controlled.

Pre-emergent activity of amidoanilides, amido-ureas and amido carbanilates are given in Tables III, IV and V respectively. The procedure followed was as described for the 3'-(carbamoyloxy) anilides and the observations were made 14 days after application.

TABLE III

PRE-EMERGENT PHYTOTOXIC ACTIVITIES OF VARIOUS AMIDO-ANILIDES

| Compound | Rate lb/acre | Morning Glory | Wild Oat | Brome Grass | Rye Grass | Radish | Sugar Beet | Foxtail | Crab Grass | Pigweed | Soybean | Wild Buckwheat | Tomato | Sorghum |
|---|---|---|---|---|---|---|---|---|---|---|---|---|---|---|
| I | 5 | 3 | 1 | 1 | 1 | 1 | 2 | 2 | 1 | 3 | 0 | 1 | 1 | 1 |
| II | 5 | 1 | 1 | 0 | 0 | 0 | 1 | — | 0 | 2 | 0 | 2 | 2 | 0 |
| III | 5 | 0 | 0 | 0 | 0 | 1 | 2 | 0 | 2 | 3 | 0 | 1 | 0 | 0 |
| IV | 5 | 1 | 0 | 3 | 1 | 1 | 1 | 1 | 2 | 0 | 0 | 2 | 1 | 1 |
| V | 5 | 1 | 1 | 1 | 1 | 3 | 3 | 1 | 2 | 3 | 0 | 1 | 1 | 3 |

I 3'-[2,2-dimethyl-3-(o-chlorophenyl)propionamido]propionanilide
II 3'-(2,2-dimethyl-4-hexenamido) 2,2-dimethylvaleranilide
III 3'-(2,2,3-trimethyl-4-pentenamido)2-methylvaleranilide
IV 3'-(2,2-dimethylbutyramido)2,2-dimethylpropionanilide
V 3'-(2-methyl-2-n-propyl-4-pentenamido)cyclopropylcarboxanilide

TABLE IV

Pre-Emergent Phytoxic Activity of Various Amido-Urea

| Compound | Rate lb/acre | Canada Thistle | Cockelbur | Velvet Leaf | Morning Glory | Lambsquarter | Smartweed | Nutsedge | Quackgrass | Johnson Grass | Bromus tectorium |
|---|---|---|---|---|---|---|---|---|---|---|---|
| I | 1 | 3 | 0 | 3 | 0 | 3 | 2 | 0 | 1 | 1 | 0 |
| II | 5 | 1 | 1 | 2 | 0 | 2 | 3 | 0 | 1 | 0 | 2 |
| III | 1+ | — | 0 | 1 | — | 3 | 1 | — | — | — | — |
| IV | 1+ | — | — | 3 | — | 2 | 3 | — | — | — | — |
| V | 2 | — | 0 | 3 | — | 3 | 3 | — | — | — | — |
| VI | 1+ | — | 0 | 3 | — | 2 | 1 | — | — | — | — |

+ Soil incorporated

| Compound | Rate lb/acre | Barnyard Grass | Sugar Beet | Cotton | Soybean | Corn | Wheat | Rice | Pigweed | Coffee Weed | Wild Oat | Brome Grass | Crab Grass |
|---|---|---|---|---|---|---|---|---|---|---|---|---|---|
| I | 1 | 0 | — | — | — | — | — | — | — | — | — | — | — |
| II | 5 | 1 | — | — | — | — | — | — | — | — | — | — | — |
| III | 1+ | 1 | 2 | 0 | 0 | 0 | 1 | 0 | 3 | 0 | 0 | 2 | 2 |
| IV | 1+ | 1 | 3 | 0 | 0 | 0 | 0 | 1 | 3 | 1 | 2 | 1 | 0 |
| V | 2 | 2 | 2 | 1 | 1 | 1 | 0 | 0 | 3 | 2 | 0 | 0 | 3 |
| VI | 1+ | 1 | 3 | 2 | 3 | 0 | 0 | 1 | 3 | 3 | 0 | 0 | 0 |

+ Soil incorporated

Compound I    3-[3'-(2,2-di-chloromethylpropionamido)phenyl]-1-t-butylurea
Compound II   3-[3'-(2,2-dimethyl-3-chloropropionamido)phenyl]-1,1-dimethylurea
Compound III  3-[3'-(2,2-dimethyl-4-pentenamido)phenyl]-1,1-diethylurea
Compound IV   3-[3'-(2,2-dimethylvaleramido)phenyl]-1-t-butylurea
Compound V    3-[3'-(2,2-dimethylpropionamido)phenyl]-1,1-dimethylurea
Compound VI   3-[3'-(2,2-dimethyl-3-phenylpropionamido)phenyl]-1-t-butylurea

TABLE V

Pre-emergent Activities of Various Amido-Carbanilates

| Compound | Rate lb/acre | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|---|
| I | 5 | 3 | 0 | 3 | 0 | 2 | 3 | 1 | 3 | 3 | 0 | 2 | 3 | 2 | — | — | — | — | — | — | — | — | — | — |
| II | 1+ | — | 0 | 0 | — | — | 2 | — | 0 | 3 | 0 | — | — | — | 0 | 0 | 0 | 1 | 1 | 2 | 0 | 0 | 0 | 1 |
| III | 10 | 2 | 1 | 1 | 1 | 2 | 2 | 2 | 2 | 3 | 0 | 1 | 2 | 0 | — | — | — | — | — | — | — | — | — | — |
| IV | 1+ | — | 1 | 1 | — | — | 1 | — | 0 | 2 | 1 | — | — | — | 1 | 0 | 0 | 0 | 1 | 0 | 2 | 0 | 0 | 1 |
| V | 1+ | — | 2 | 0 | — | — | 1 | — | 3 | 3 | 0 | — | — | — | 1 | 2 | 0 | 2 | 2 | — | 3 | 2 | 2 | 1 |

+ Soil incorporated
Compound I methyl 3'-(2,2-dimethyl-4-pentenamido)carbanilate
Compound II methyl 3'-(2-methylvaleramido)thiolcarbanilate
Compound III methyl 3'-(2-methylvaleramido)carbanilate
Compound IV n-propyl 3'-(2,2-dimethylvaleramido)thiolcarbanilate
Compound V methyl 3'-(2,2-dimethylvaleramido)carbamilate A Morning Glory
B Wild Oat
C Brome Grass
D Rye Grass
E Radish
F Sugar Beet
G Foxtail
H Crab Grass
I Pigweed
J Soybean
K Wild Buckwheat
L Tomato
M Sorghum
N Cotton
O Corn
P Wheat
Q Rice
R Smartweed
S Cockelbur
T Lambsquarter
U Coffee Weed
V Velvet Leaf
W Barnyard Grass The post-emergent plant growth regulant activity of various compounds of this invention is demonstrated as follows. The active ingredients are applied in spray form to 14-day or 21-day old specimens of many of the same plant species used in the preceding pre-emergent tests. The spray, an aqueous-organic solvent containing active ingredient, is applied to the plants in different sets of pans at several rates of active ingredient per acre. The treated plants are placed in a greenhouse and the effects are observed and recorded after approximately 14 days or approximately 28 days, as is indicated in Table VI (3'-carbamoyloxyanilides) by the terms (a) and (b), respectively. In Tables VII (amido-anilides), VIII (amido ureas) and IX (amido-carbanilates) 14 day old plants were treated and observations made after 14 days.

The post-emergent phytotoxic activity index used in Table VI is measured by the average percent control of each plant species and is defined as follows:

| Phytotoxicity | | Numerical Scale |
|---|---|---|
| None | = | 0 |
| Slight | = | 1 |
| Moderate | = | 2 |
| Severe | = | 3 |
| Dead (kill) | = | 4 |

The identification of the plants used in Table VI is the same as in Table I. The terms (c) and (d) as used in the Comments column of Table VI mean 14-day old plants and 21-day old plants, respectively. Results and further details are given in Table VI.

TABLE VI

POST-EMERGENT PHYTOTOXIC ACTIVITY OF VARIOUS 3'-(CARBAMOYLOXY)ANILIDES

| Compound | Comments | Rate lbs./acre | C | D | E | F | G | H | I | J | K | L | M | N | O | P | Q | R | S |
|---|---|---|---|---|---|---|---|---|---|---|---|---|---|---|---|---|---|---|---|
| 3'-(diethylthiocarbamoyloxy)-propionanilide | (a) (d) | 10 | 4 | 3 | 3 | 3 | 4 | 4 | — | — | 3 | — | 4 | 4 | 4 | 4 | 4 | 3 | — |
| N-isopropyl-3'-(methylcarbamoyl-oxy)-alpha-chloroacetanilide | (a) (c) | 10 | 2 | 0 | 0 | 0 | 0 | 0 | — | — | 2 | — | 3 | 4 | 0 | 0 | 1 | 0 | — |
| 3'-(2,6-dimethyl-1-piperidine-carboxy)propionanilide | (a) (d) | 10 | 4 | 3 | 2 | 0 | 4 | 4 | — | — | 3 | — | 3 | 4 | 4 | 4 | 4 | 1 | — |
| 3'-(methylcarbamoyloxy)propion-anilide | (a) (c) | 10 | 4 | 3 | 3 | 3 | 4 | 4 | — | — | 3 | — | 3 | 4 | 4 | 4 | 4 | 0 | — |
| | (b) (c) | 1 | — | 0 | 1 | — | — | 2 | 0 | 1 | — | 1 | 0 | 4 | 1 | — | — | — | 2 |
| 3'-(diethylcarbamoyloxy)propionanilide | (a) (d) | 10 | 4 | 3 | 3 | 2 | 4 | 4 | — | — | 3 | — | 3 | 4 | 4 | 4 | 4 | 2 | — |
| 3'-(t-butylcarbamoyloxy)propionanilide | (a) (c) | 10 | 4 | 1 | 3 | 4 | 4 | 4 | — | — | 3 | — | 4 | 4 | 2 | 4 | 4 | 0 | — |
| | (b) (c) | 0.1 | — | 1 | 1 | — | — | 2 | 1 | 3 | — | 0 | 3 | 4 | 1 | — | — | — | 1 |
| 3'-(ethylcarbamoyloxy)propionanilide | (a) (c) | 10 | 4 | 0 | 0 | 0 | 4 | 4 | — | — | 2 | — | 2 | 4 | 4 | 4 | 4 | 2 | — |
| | (b) (c) | 1 | 2 | 1 | 1 | — | — | 3 | 3 | 2 | — | 1 | 0 | 4 | 3 | — | — | — | 3 |
| 3'-(isopropylcarbamoyloxy)propion-anilide | (a) (c) | 10 | 3 | 2 | 3 | 3 | 4 | 3 | — | — | 3 | — | 3 | 4 | 4 | 4 | 4 | 3 | — |
| 3'-(n-propylcarbamoyloxy)propion-anilide | (a) (c) | 10 | 4 | 3 | 3 | 3 | 4 | 4 | — | — | 3 | — | 4 | 4 | 4 | 4 | 4 | 3 | — |
| | (b) (c) | 0.2 | — | 0 | 0 | — | — | 2 | 1 | 0 | — | 0 | 0 | 4 | 0 | — | — | — | 1 |
| 3'(4-morpholinecarboxy)propion-anilide | (a) (d) | 10 | 3 | 1 | 0 | 0 | 3 | 3 | — | — | 1 | — | 1 | 4 | 1 | 4 | 3 | 0 | — |
| 3'-(phenylcarbamoyloxy)propion-anilide | (a) (c) | 10 | 4 | 3 | 3 | 2 | 4 | 4 | — | — | 3 | — | 3 | 4 | 4 | 4 | 4 | 3 | — |

TABLE VI-continued
POST-EMERGENT PHYTOTOXIC ACTIVITY OF VARIOUS 3'-(CARBAMOYLOXY)ANILIDES

| Compound | | | | | | | | | | | | | | | | | | | |
|---|---|---|---|---|---|---|---|---|---|---|---|---|---|---|---|---|---|---|---|
| 3'-(1-piperidinecarboxy)-2,2,2-trimethylacetanilide | (a) | (d) | 10 | 4 | 1 | 1 | 1 | 4 | 4 | — | — | 1 | — | 2 | 4 | 4 | 4 | 4 | 1 | — |
| 3'-(m-chlorophenylcarbamoyloxy)-propionanilide | (a) | (c) | 10 | 4 | 3 | 3 | 2 | 4 | 4 | — | — | 3 | — | 3 | 4 | 3 | 4 | 4 | 2 | — |
| 3'-(2,6-dimethyl-1-piperidinecarboxy)-2,2,2-trimethylacetanilide | (a) | (d) | 10 | 4 | 0 | 0 | 0 | 4 | 4 | — | — | 0 | — | 1 | 4 | 2 | 1 | 1 | 1 | — |
| 3'-(cyclohexylcarbamoyloxy)propionanilide | (a) | (c) | 10 | 2 | 1 | 0 | 0 | 4 | 2 | — | — | 0 | — | 1 | 4 | 3 | 4 | 4 | 0 | — |
| | (b) | (d) | 1 | — | 1 | 1 | — | — | 0 | 0 | 0 | — | 1 | 3 | 4 | 1 | — | — | — | 0 |
| 3'-(dimethylcarbamoyloxy)propionanilide | (b) | (c) | 10 | 4 | 1 | 0 | 0 | 2 | 3 | — | — | 2 | — | 1 | 4 | 2 | 4 | 3 | 0 | — |
| 3'-(methylcarbamoyloxy)-2-methyl-propionanilide | (b) | (c) | 10 | 2 | 0 | 0 | 0 | 1 | 4 | — | — | 0 | — | 0 | 4 | 0 | 4 | 3 | 0 | — |
| | (a) | (d) | 4 | — | 1 | 1 | — | — | 2 | 0 | 1 | 0 | — | 1 | 4 | 2 | — | — | — | 0 |
| 3'-(ethylcarbamoyloxy)-2-methyl-propionanilide | (a) | (d) | 4 | — | 0 | 1 | — | — | 2 | 0 | 0 | — | 1 | 1 | 4 | 1 | — | — | — | 1 |
| 3'-(n-propylcarbamoyloxy)-2-methyl-propionanilide | (b) | (c) | 1 | — | 0 | 0 | — | — | 2 | 0 | 0 | — | 0 | 1 | 4 | 0 | — | — | — | 1 |
| 3'-(n-butylcarbamoyloxy)-2-methyl-propionanilide | (b) | (c) | 0.1 | — | 0 | 0 | — | — | 0 | 0 | 0 | — | 0 | 0 | 0 | 0 | — | — | — | 0 |
| 3'-(p-chlorophenylcarbamoyloxy)-2-methylpropionanilide | (a) | (c) | 4 | — | 1 | 1 | — | — | 2 | 1 | 0 | — | 1 | 3 | 4 | 1 | — | — | — | 0 |
| 3'-(diphenylcarbamoyloxy)-2-methyl-propionanilide | (b) | (d) | 10 | 2 | 0 | 0 | 0 | 4 | 4 | — | — | 0 | — | 0 | 4 | 0 | 4 | 4 | 0 | — |
| 3'-(ethylcarbamoyloxy)-2-methyl-valeranilide | (a) | (c) | 1 | — | 0 | 1 | — | — | 4 | 0 | 0 | — | 0 | 1 | 4 | 1 | — | — | — | 1 |
| 3'-(n-propylcarbamoyloxy)-2-methyl-valeranilide | (a) | (c) | 1 | — | 0 | 0 | — | — | 4 | 1 | 0 | — | 1 | 2 | 4 | 1 | — | — | — | 0 |
| 3'-(n-butylcarbamoyloxy)-2-methyl-valeranilide | (a) | (c) | 4 | — | 0 | 0 | — | — | 1 | 0 | — | 1 | 2 | 4 | 1 | — | — | — | 1 | |
| 3'-(1,1,3,3-tetramethylbutylcarbamoyloxy)propionanilide | (a) | (d) | 4 | | 2 | 2 | | | 4 | 4 | 2 | | 2 | 3 | 4 | 4 | | | | 1 |
| 3'-(1,1,3,3-tetramethylbutylcarbamoyloxy)-2-methylpropionanilide | (a) | (d) | 1 | | 0 | 0 | | | 0 | 1 | 1 | | 0 | 1 | 3 | 1 | | | | 2 |
| 3'-(p-chlorophenylcarbamoyloxy)-cyclopropylcarboxanilide | (b) | (d) | 1 | | 0 | 1 | | | 0 | 0 | 0 | | 0 | 2 | 4 | 0 | | | | 1 |
| 3'-(p-chlorophenylcarbamoyloxy)-acrylanilide | (b) | (d) | 4 | | 1 | 0 | | | 3 | 0 | 0 | | 1 | 0 | 0 | 0 | | | | 3 |
| 3'-(n-butylcarbamoyloxy)cyclopropylcarboxanilide | (b) | (d) | 1 | | 1 | 1 | | | 4 | 0 | 1 | | 1 | 1 | 4 | 2 | | | | 0 |
| 3'-(ethylcarbamoyloxy)cyclopropylcarboxanilide | (a) | (d) | 4 | | 0 | 0 | | | 4 | 0 | 0 | | 1 | 0 | 4 | 0 | | | | 0 |
| 3'-(n-butylcarbamoyloxy)acryl-anilide | (b) | (d) | 1 | | 0 | 0 | | | 0 | 0 | 0 | | 0 | 0 | 0 | 0 | | | | 0 |
| 3'-(t-butylcarbamoyloxy)acryl-anilide | (a) | (d) | 1 | | 1 | 0 | | | 0 | 0 | 0 | | 0 | 0 | 0 | 0 | | | | 0 |
| 3'-(t-butylcarbamoyloxy)-2-methoxy-acetanilide | (b) | (d) | 4 | | 0 | 0 | | | 3 | 0 | 1 | | 0 | 1 | 4 | 0 | | | | 2 |
| 3'-(n-butylcarbamoyloxy)-2-methoxy-acetanilide | (b) | (d) | 1 | | 0 | 0 | | | 3 | 0 | 3 | | 0 | 0 | 3 | 0 | | | | 2 |
| 3'-(t-butylcarbamoyloxy)croton-anilide | (b) | (d) | 1 | | 1 | 2 | | | 4 | 0 | 2 | | 1 | 2 | 4 | 1 | | | | 1 |
| 3'-(methylcarbamoyloxy)croton-anilide | (b) | (d) | 4 | | 1 | 0 | | | 2 | 4 | 1 | | 1 | 3 | 1 | 3 | | | | 3 |
| 3'-(methylcarbamoyloxy)phenyl-carboxanilide | (b) | (d) | 4 | | 0 | 0 | | | 0 | 0 | 0 | | 0 | 0 | 4 | 0 | | | | 0 |
| 3'-(methylcarbamoyloxy)-2-phenyl-acetanilide | (b) | (d) | 4 | | 0 | 0 | | | 2 | 1 | 0 | | 0 | 0 | 4 | 1 | | | | 0 |
| 3'-(methylcarbamoyloxy)cyclopropylcarboxanilide | (b) | (d) | 4 | | 2 | 2 | | | 4 | 3 | 3 | | 2 | 2 | 4 | 4 | | | | 3 |
| 3'-(methylcarbamoyloxy)-2-methoxy-acetanilide | (b) | (d) | 4 | | 2 | 1 | | | 4 | 1 | 3 | | 0 | 0 | 4 | 1 | | | | 1 |
| 3'-(1,1,3,3-tetramethylbutylcarbamoyloxy)acrylanilide | (b) | (d) | 4 | | 0 | 1 | | | 4 | 3 | 2 | | 1 | 1 | 4 | 3 | | | | 3 |
| 3'-(1,1,3,3-tetramethylbutylcarbamoyloxy)cyclopropylcarboxanilide | (b) | (d) | 1 | | 0 | 1 | | | 0 | 2 | 0 | | 0 | 1 | 4 | 0 | | | | 0 |
| 3'-(t-butylcarbamoyloxy)cyclopropylcarboxanilide | (b) | (d) | 4 | | 1 | 1 | | | 4 | 1 | 0 | | 1 | 3 | 4 | 3 | | | | 1 |
| 3'-(1,1,3,3-tetramethylbutylcarbamoyloxy)-2-methylvaleranilide | (a) | (d) | 1 | | 0 | 0 | | | 0 | 0 | 0 | | 0 | 3 | 0 | 2 | | | | 1 |
| 3'-(1,1,3,3-tetramethylbutylcarbamoyloxy)-2-methylacrylanilide | (b) | (d) | 1 | | 0 | 1 | | | 0 | 1 | 1 | | 0 | 1 | 4 | 3 | | | | 0 |
| 3'-(p-chlorophenylcarbamoyloxy)-2-methylacrylanilide | (b) | (d) | 1 | | 1 | 2 | | | 4 | 2 | 2 | | 1 | 2 | 4 | 0 | | | | 1 |
| 3'-(ethylcarbamoyloxy)-2-methyl-acrylanilide | (b) | (d) | 4 | | 0 | 0 | | | 3 | 0 | 0 | | 0 | 1 | 0 | 1 | | | | 0 |

| Compound | | | | T | U | V | W | X | Y |
|---|---|---|---|---|---|---|---|---|---|
| 3'-(diethylthiocarbamoyloxy)-propionanilide | (a) | (d) | 10 | — | — | — | — | — | — |
| N-isopropyl-3'-(methylcarbamoyloxy)-alpha-chloroacetanilide | (a) | (c) | 10 | — | — | — | — | — | — |
| 3'-(2,6-dimethyl-1-piperidinecarboxy)propionanilide | (a) | (d) | 10 | — | — | — | — | — | — |
| 3'-(methylcarbamoyloxy)propionanilide | (a) | (c) | 10 | — | — | — | — | — | — |
| | (b) | (c) | 1 | 4 | 2 | — | 2 | 0 | 2 |
| 3'-(diethylcarbamoyloxy)propionanilide | (a) | (d) | 10 | — | — | — | — | — | — |
| 3'-(t-butylcarbamoyloxy)propionanilide | (a) | (c) | 10 | — | — | — | — | — | — |
| | (b) | (c) | 0.1 | 4 | — | 3 | 4 | 1 | 3 |
| 3'-(ethylcarbamoyloxy)propionanilide | (a) | (c) | 10 | — | — | — | — | — | — |
| | (b) | (c) | 1 | 4 | — | 4 | 3 | 2 | 4 |
| 3'-(isopropylcarbamoyloxy)propionanilide | (a) | (c) | 10 | — | — | — | — | — | — |
| 3'-(n-propylcarbamoyloxy)propionanilide | (a) | (c) | 10 | — | — | — | — | — | — |

TABLE VI-continued

POST-EMERGENT PHYTOTOXIC ACTIVITY OF VARIOUS 3'-(CARBAMOYLOXY)ANILIDES

| anilide | | | | | | | | | |
|---|---|---|---|---|---|---|---|---|---|
| 3'-(4-morpholinecarboxy)propion-anilide | (b) | (c) | 0.2 | 4 | — | 4 | 0 | 1 | 1 |
| 3'-(4-morpholinecarboxy)propion-anilide | (a) | (d) | 10 | — | — | — | — | — | — |
| 3'-(phenylcarbamoyloxy)propion-anilide | (a) | (c) | 10 | — | — | — | — | — | — |
| 3'-(1-piperidinecarboxy)-2,2,2-trimethylacetanilide | (a) | (d) | 10 | — | — | — | — | — | — |
| 3'-(m-chlorophenylcarbamoyloxy)-propionanilide | (a) | (c) | 10 | — | — | — | — | — | — |
| 3'-(2,6-dimethyl-1-piperidinecarboxy)-2,2,2-trimethylacetanilide | (a) | (d) | 10 | — | — | — | — | — | — |
| 3'-(cyclohexylcarbamoyloxy)propion-anilide | (a) | (c) | 10 | — | — | — | — | — | — |
| 3'-(cyclohexylcarbamoyloxy)propion-anilide | (b) | (d) | 1 | 4 | — | 4 | 4 | 0 | 2 |
| 3'-(dimethylcarbamoyloxy)propion-anilide | (b) | (c) | 10 | — | — | — | — | — | — |
| 3'-(methylcarbamoyloxy)-2-methyl-propionanilide | (b) | (c) | 10 | — | — | — | — | — | — |
| 3'-(ethylcarbamoyloxy)-2-methyl-propionanilide | (a) | (d) | 4 | 4 | 1 | 4 | 3 | 0 | 0 |
| 3'-(n-propylcarbamoyloxy)-2-methyl-propionanilide | (b) | (c) | 1 | 4 | 0 | 4 | 3 | 0 | 0 |
| 3'-(n-butylcarbamoyloxy)-2-methyl-propionanilide | (b) | (c) | 0.1 | 0 | 0 | 4 | 0 | 0 | 0 |
| 3'-(p-chlorophenylcarbamoyloxy)-2-methylpropionanilide | (a) | (c) | 4 | 4 | 0 | 4 | 2 | 0 | 1 |
| 3'-(diphenylcarbamoyloxy)-2-methyl-propionanilide | (b) | (d) | 10 | — | — | — | — | — | — |
| 3'-(ethylcarbamoyloxy)-2-methyl-valeranilide | (a) | (c) | 1 | 4 | — | 4 | 3 | 0 | 0 |
| 3'-(n-propylcarbamoyloxy)-2-methyl-valeranilide | (a) | (c) | 1 | 4 | — | 4 | 3 | 0 | 0 |
| 3'-(n-butylcarbamoyloxy)-2-methyl-valeranilide | (a) | (c) | 4 | 4 | 0 | 4 | 4 | 0 | 2 |
| 3'-(1,1,3,3-tetramethylbutylcarbamoyloxy)propionanilide | (a) | (d) | 4 | 4 | 4 | 4 | 4 | 1 | 4 |
| 3'-(1,1,3,3-tetramethylbutylcarbamoyloxy)-2-methylpropionanilide | (a) | (d) | 1 | 1 | — | 4 | 4 | 1 | 1 |
| 3'-(p-chlorophenylcarbamoyloxy)-cyclopropylcarboxanilide | (b) | (d) | 1 | 0 | 0 | 4 | 4 | 0 | 0 |
| 3'-(p-chlorophenylcarbamoyloxy)-acrylanilide | (b) | (d) | 4 | 0 | 0 | 3 | 4 | 1 | 0 |
| 3'-(n-butylcarbamoyloxy)cyclopropylcarboxanilide | (b) | (d) | 1 | 4 | 3 | 4 | 4 | 0 | 0 |
| 3'-(ethylcarbamoyloxy)cyclopropylcarboxanilide | (a) | (d) | 4 | 4 | 1 | 4 | 4 | 0 | 0 |
| 3'-(n-butylcarbamoyloxy)acryl-anilide | (b) | (d) | 1 | 4 | 0 | 0 | 1 | 0 | 0 |
| 3'-(t-butylcarbamoyloxy)acryl-anilide | (a) | (d) | 1 | 4 | 0 | 0 | 4 | 0 | 0 |
| 3'-(butylcarbamoyloxy)-2-methoxy-acetanilide | (b) | (d) | 4 | 2 | 0 | 0 | 2 | 1 | 0 |
| 3'-(n-butylcarbamoyloxy)-2-methoxy-acetanilide | (b) | (d) | 1 | 4 | 0 | 4 | 1 | 0 | 2 |
| 3'-(t-butylcarbamoyloxy)croton-anilide | (b) | (d) | 1 | 4 | 4 | 4 | 4 | 1 | 4 |
| 3'-(methylcarbamoyloxy)croton-anilide | (b) | (d) | 4 | 4 | 4 | 4 | 2 | 1 | 1 |
| 3'-(methylcarbamoyloxy)phenyl-carboxanilide | (b) | (d) | 4 | 0 | 0 | 0 | 0 | 0 | 0 |
| 3'-(methylcarbamoyloxy)-2-phenyl-acetanilide | (b) | (d) | 4 | 4 | 0 | 3 | 4 | 0 | 0 |
| 3'-(methylcarbamoyloxy)cyclopropylcarboxanilide | (b) | (d) | 4 | 4 | 4 | 4 | 4 | 1 | 4 |
| 3'-(methylcarbamoyloxy)-2-methoxy-acetanilide | (b) | (d) | 4 | 2 | 2 | 4 | 1 | 0 | 2 |
| 3'-(1,1,3,3-tetramethylbutylcarbamoyloxy)acrylanilide | (b) | (d) | 4 | 4 | 4 | 4 | 4 | 0 | 4 |
| 3'-(1,1,3,3-tetramethylbutylcarbamoyloxy)cyclopropylcarboxanilide | (b) | (d) | 1 | 2 | 1 | 3 | 4 | 0 | 1 |
| 3'-(t-butylcarbamoyloxy)cyclopropylcarboxanilide | (b) | (d) | 4 | 4 | 3 | 4 | 4 | 0 | 2 |
| 3'-(1,1,3,3-tetramethylbutylcarbamoyloxy)-2-methylvaleranilide | (a) | (d) | 1 | 1 | 0 | 4 | 4 | 0 | 0 |
| 3'-(1,1,3,3-tetramethylbutylcarbamoyloxy)-2-methylacrylanilide | (b) | (d) | 1 | 4 | 4 | 4 | 4 | 0 | 4 |
| 3'-(p-chlorophenylcarbamoyloxy)-2-methylacrylanilide | (b) | (d) | 1 | 1 | 1 | 4 | 2 | 1 | 1 |
| 3'-(ethylcarbamoyloxy)-2-methyl-acrylanilide | (b) | (d) | 4 | 4 | 1 | 3 | 3 | 0 | 4 |

TABLE VII

Post-emergent Phytotoxic Activity of Various Amido-Amido

| Compound | % Conc. | A | B | C | D | E | F | G | H | I | J | K | L | M | N | O | P | Q | R | S | T | U | V | W | X |
|---|---|---|---|---|---|---|---|---|---|---|---|---|---|---|---|---|---|---|---|---|---|---|---|---|---|
| I | 0.2 | 2 | 0 | 1 | 0 | 3 | 4 | 1 | 2 | 3 | 2 | 4 | 4 | 1 | — | — | — | — | — | — | — | — | — | — | — |
| II | 0.2 | 3 | 3 | 2 | 2 | 3 | 4 | 2 | 3 | 4 | 3 | 4 | 3 | 2 | — | — | — | — | — | — | — | — | — | — | — |
| III | 0.05 | 4 | — | 3 | — | — | 2 | — | 2 | — | 0 | 4 | — | 1 | — | — | 2 | 2 | 4 | 4 | — | 4 | 2 | 2 | 1 |
| IV | 0.05 | 3 | — | 3 | — | — | 4 | — | 3 | — | 4 | 4 | — | 0 | — | — | 1 | 2 | 4 | 4 | 4 | 4 | 4 | 2 | 2 |

TABLE VII-continued

Post-emergent Phytotoxic Activity of Various Amido-Amido

| Compound | % Conc. | A | B | C | D | E | F | G | H | I | J | K | L | M | N | O | P | Q | R | S | T | U | V | W | X |
|---|---|---|---|---|---|---|---|---|---|---|---|---|---|---|---|---|---|---|---|---|---|---|---|---|---|
| V | 0.2 | 4 | 2 | 1 | 1 | 4 | 4 | 2 | 3 | 4 | 1 | 4 | 3 | 2 | — | — | — | — | — | — | — | — | — | — | — |

Compound I 3'-(2,2-dimethyl-4-pentenamido)2,2-dimethylpropionanilide
Compound II 3'-(2,2-dimethyl-4-pentenamido)cyclopropylcarboxanilide
Compound III 3'-(2,2-di-chloromethylpropionamido)propionanilide
Compound IV 3'-(2,2-dimethyl-3,3-dichloropropionamido)propionanilide
Compound V 3'-(2,2-dimethyl-3-phenylpropionamido)cyclopropylcarboxanilide
Compound VI 3'-[2,2-dimethyl-3-(p-chlorophenyl)propionamido]propionanilide
A MorningGlory
B Wild Oat
C Downy Brome
D Rye Grass
E Radish
F Sugar Beet
G Foxtail
H Crab Grass
I Pigweed
J Soybean
K Wild Buckwheat
L Tomato
M Sorghum
N Cotton
O Corn
P Wheat
Q Rice
R Smartweed
S Cockelbur
T Lambsquarter
U Coffee Weed
V Velvet Leaf
W Barnyard Grass
X Panicum

TABLE VIII

Post-emergent Phytotoxic Activity of Various Amido-Ureas

| Compound | % Conc. | A | B | C | D | E | F | G | H | I | J | K | L | M | N | O | P | Q | R | S | T | U |
|---|---|---|---|---|---|---|---|---|---|---|---|---|---|---|---|---|---|---|---|---|---|---|
| I | 0.05 | 2 | 0 | 0 | 1 | 0 | 0 | 4 | 4 | 2 | 4 | 3 | 0 | 2 | 2 | 1 | 1 | — | — | — | — | — |
| II | 0.05 | 4 | — | 4 | — | 3 | 3 | — | 4 | 4 | 4 | 4 | 4 | — | — | 2 | 2 | 3 | — | 4 | 1 | 4 |
| III | 0.05 | 1 | 0 | 1 | 0 | 0 | 1 | 4 | 2 | 0 | 2 | 2 | 0 | 1 | 1 | 1 | 1 | — | — | — | — | — |
| IV | 0.05 | 4 | 3 | 4 | 2 | 2 | 2 | 4 | 4 | 4 | 4 | 4 | 2 | 3 | 4 | 4 | 4 | — | — | — | — | — |
| V | 0.05 | 1 | 0 | 0 | 1 | 0 | 1 | 3 | 1 | 1 | 3 | 2 | 1 | 0 | 3 | 1 | 2 | — | — | — | — | — |
| VI | 0.05 | 3 | 0 | 2 | 2 | 0 | 2 | 3 | 1 | 2 | 2 | 2 | 2 | 0 | 0 | 1 | 0 | — | — | — | — | — |

Compound I 3-[3'-(propionamido)phenyl]1,1-di-n-butylthiourea
Compound II 3-[3'-(2,2-dimethyl-3,3-dichloropropionamido)phenyl]-1,1-dimethylurea
Compound III 3-[3'-(2,2-dimethylpropionamido)phenyl]-1,1-diallylthiourea
Compound IV 3-[3'-(2-methylvaleramido)phenyl]-1-t-butylurea
Compound V 3-[3'-(2-methylvaleramido)phenyl]-1-phenylthiourea
Compound VI 3-[3'-(2,2-dimethylpropionamido)phenyl]-1-methyl-1-methoxythiourea
A Sugar Beet
B Cotton
C Soybean
D Corn
E Wheat
F Rice
G Pigweed
H Smartweed
I Cockelbur
J Lambsquarter
K Coffee Weed
L Velvet Leaf
M Wild Oat
N Brome Grass
O Barnyard Grass
P Crab
Q Sorghum
R Wild Buckwheat
S Morning Glory
T Downy Brome
U Panicum

TABLE IX

Post-Emergent Phytotoxic Activity of Various amido-carbanilates

| Compound | % Conc. | A | B | C | D | E | F | G | H | I | J | K | L | M | N | O | P |
|---|---|---|---|---|---|---|---|---|---|---|---|---|---|---|---|---|---|
| I | 0.05 | 4 | 1 | 2 | 3 | 1 | 2 | 4 | 4 | 4 | 4 | 4 | 1 | 1 | 1 | 1 | 2 |
| II | 0.05 | 3 | 0 | 1 | 1 | 1 | 1 | 4 | 3 | 1 | 2 | 2 | 1 | 1 | 1 | 1 | 1 |
| III | 0.05 | 4 | 0 | 1 | 0 | 1 | 0 | 4 | 4 | 1 | 4 | 2 | 1 | 1 | 2 | 1 | 2 |
| IV | 0.05 | 4 | 1 | 2 | 1 | 3 | 3 | 4 | 4 | 4 | 4 | 3 | 2 | 2 | 2 | 3 | 2 |

TABLE IX-continued

Post-Emergent Phytotoxic Activity of Various amido-carbanilates

| Compound | % Conc. | A | B | C | D | E | F | G | H | I | J | K | L | M | N | O | P |
|---|---|---|---|---|---|---|---|---|---|---|---|---|---|---|---|---|---|
| V | 0.05 | 1 | 0 | 0 | 0 | 0 | 1 | 4 | 4 | 0 | 4 | 1 | 0 | 1 | 0 | 0 | 2 |

Compound I methyl 3'-(2-methylpropionamido)thiolcarbanilate
Compound II ethyl 3'-(2-methylvaleramido)thiolcarbanilate
Compound III ethyl 3'-(2,2-dimethylvaleramido)thiolcarbanilate
Compound IV methyl 3'-(2,2-dimethylvaleramido)thiolcarbanilate
Compound V isopropyl 3'-(propionamido)carbanilate
A Sugar Beet
B Cotton
C Soybean
D Corn
E Wheat
F Rice
G Pigweed
H Smartweed
I Cocklebur
J Lambsquarter
K Coffee Weed
L Velvet Leaf
M Wild Oat
N Brome
O Barnyard Grass
P Crab While carrying out the above and other post-emergent tests with 3'-(carbamoyloxy)anilides, numerous specific plant growth responses were observed and recorded. Some of the observed plant growth responses at various application rates are as follows:

TABLE X

| Compound | Application Rate, lb/acre | Plant Growth Response |
|---|---|---|
| 3'-(t-butylcarbamoyloxy)-propionanilide | 0.1 | Stunting of corn, wild oats, brome, crab grass, barnyard grass, wheat and rice. |
| 3'-(n-butylcarbamoyloxy)-2-methylpropionanilide | 1 | Stunting of corn, wild oats, brome, crab grass, barnyard grass, wheat and rice. |
| 3'-(methylcarbamoyloxy)-2-methylvaleranilide | 1 | Stunting of corn, wild oats, brome, crab grass, barnyard grass, wheat and rice. |
| 3'-(ethylcarbamoyloxy)-2-methylvaleranilide | 1 | Stunting of corn, wild oats, brome, crab grass, barnyard grass, wheat and rice. |
| 3'-(cyclohexylcarbamoyloxy)propionanilide | 1 | Stunting of wild oats, brome, crab grass, barnyard grass, wheat and rice. |
| 3'-(1,1,3,3-tetramethylbutylcarbamoyloxy)-2-methylacrylanilide | 1 | Stunting of cotton and corn. |
| 3'-(1,1,3,3-tetramethylbutylcarbamoyloxy)-2-methylacrylanilide | 4 | Dessication of soybean leaf. |
| 3'-(t-butylcarbamoyloxy)cyclopropylcarboxanilide | 4 | Stunting of cotton. Defoliation of cotton. Tillering of wheat. |
| 3'-(ethylcarbamoyloxy)-2-methoxyacetanilide | 4 | Stunting of cotton, corn and soybean. |
| 3'-(ethylcarbamoyloxy)-2-methoxyacetanilide | 10 | Defoliation of soybean. |
| 3'-(p-chlorophenylcarbamoyloxy)acrylanilide | 10 | Stunting of sorghum. |
| 3'-(p-chlorophenylcarbamoyloxy)cyclopropylcarboxanilide | 10 | Stunting of sorghum |
| 3'-(1,1,3,3-tetramethylbutylcarbamoyloxy)cyclopropylcarboxanilide | 0.2 | Stunting of corn. |
| 3'-(1,1,3,3-tetramethylbutylcarbamoyloxy)cyclopropylcarboxanilide | 4 | Defoliation of soybean. |
| 3'-(1,1,3,3-tetramethylbutylcarbamoyloxy)propionanilide | 0.2 | Stunting of corn. |
| 3'-(1,1,3,3-tetramethylbutylcarbamoyloxy)-2-methylvaleranilide | 1 | Defoliation of cotton. |
| 3'-(1,1,3,3-tetramethylbutylcarbamoyloxy)-acrylanilide | 4 | Defoliation of soybean. |
| 3'-(t-butylcarbamoyloxy)-crotonanilide | 4 | Defoliation of soybean. |
| 3'-(n-butylcarbamoyloxy)-2- | 4 | Defoliation of soybean. |

TABLE X-continued

| Compound | Application Rate, lb/acre | Plant Growth Response |
|---|---|---|
| methoxyacetanilide | | |
| 3'-(o-chlorophenylcarbamoyl-oxy)-2-methylacrylanilide | 10 | Defoliation of soybean. |
| 3'-(methylcarbamoyloxy)-cyclopropylcarboxanilide | 0.2 | Leaf necrosis followed by dessication. |
| 3'-(m-chlorophenylcarbamoyl-oxy)-2-methylacrylanilide | 10 | Tillering of rye grass. |
| 3'-(n-butylcarbamoyloxy)-2-methylacrylanilide | 4 | Dessication of lambs-quarter, smartweed, sugar beet and coffee weed. |
| 3'-(t-butylcarbamoyloxy)-acrylanilide | 4 | Stimulation of corn. The treated corn was 4 inches taller than control corn. |

The plant growth regulant activity of the active ingredients of this invention on woody plant species is demonstrated as follows: Established trees about 18 inches in height were sprayed with active ingredient at a rate of 5 pounds per acre. The active ingredients were sprayed in the form of the emulsion used in the above post-emergent tests. The post-emergent phytotoxic index used in Table XI is defined as in the above post-emergent tests. The trees were observed about 6 months after spraying and the results recorded. Results are given in Table XI below.

TABLE XI

| Compound | Woody Plant | | | | |
|---|---|---|---|---|---|
| | Maple | Elm | Pin Oak | Arborvitae | Green Ash |
| 3'-(metylcarbamoyl-oxy)-2-methylvaler-anilide | 1 | 4 | 1 | 1 | 2 |
| 3'-(ethylcarbamoyl-oxy)-2-methylvaler-anilide | 1 | 4 | 2 | 0 | 0 |
| 3'-(n-propylcarbam-oyloxy)-2-methyl-valeranilide | 4 | 4 | 2 | 1 | 1 |
| 3'-(t-butylcarbam-oyloxy)-2-methyl-valeranilide | 4 | 4 | 4 | 0 | 1 |
| 3'-(ethylcarbamoyl-oxy)propionanilide | 4 | 4 | 4 | 3 | 4 |
| 3'-(isopropylcarbam-oyloxy)propion-anilide | 4 | 4 | 4 | 4 | 4 |
| 3'-(n-propylcarbam-oyloxy)propion-anilide | 4 | 4 | 4 | 4 | 2 |

The post-emergent phytotoxic activity of 3'-(carbamoyloxy) anilides ingredients of this invention on perennial species is demonstrated as follows. The active ingredients listed in Table VI below were sprayed on 4 week old Canada thistle, bindweed and horsenettle at the rate of 1 pound of active ingredient per acre. The plants were observed 3 weeks after spraying and the results recorded. The post-emergent phytotoxic activity index used in Table XII is defined as in the above post-emergent tests.

TABLE XII

| Compound | Plant | | |
|---|---|---|---|
| | Canada Thistle | Bindweed | Horsenettle |
| 3'-(n-butylcarbam-oyloxy)propion-anilide | 4 | 4 | 3 |

The aquatic plant phytotoxic activity of illustrative 3'-(carbamoyloxy)anilides of this invention is demonstrated as follows: 3'-(ethylcarbamoyloxy)propionanilide was added to a vessel containing aqueous inorganic nutrient media and Duckweed (Spirodela). The active ingredient was used at a concentration of 100 ppm. based on the aqueous nutrient media. After 48 hours all of the treated Duckweed was dead. Untreated Duckweed remained healthy and continued to grow during the tests.

As mentioned hereinbefore the plant growth regulant compositions of this invention comprise an active ingredient and one or more adjuvants which can be solid or liquid extenders, carriers, diluents, conditioning agents and the like. Preferred plant growth regulant compositions containing the active ingredients of this invention have been developed so that the active ingredients can be used to the greatest advantage to modify the growth of plants. The preferred compositions comprise wettable powders, aqueous suspensions, dust formulations, granules, emulsifiable oils and solutions in solvents. In general, these preferred compositions can all contain one or more surface-active agents.

Surface-active agents which can be used in the phytotoxic compositions of this invention are set out, for example, in Searle U.S. Pat. No. 2,426,417, Todd U.S. Pat. No. 2,655,447, Jones U.S. Pat. No. 2,412,510 and Lenher U.S. Pat. No. 2,139,276. A detailed list of such agents is also set forth by J. W. McCutcheon in "Soap and Chemical Specialties", November 1947, page 8011 et seq., entitled "Synthetic Detergents"; "Detergents and Emulsifiers — Up to Date" (1960), by J. W.

McCutcheon, Inc., and Bulletin E-607 of the Bureau of Entomology and Plant Quarantine of the U.S.D.A. In general, less than 50 parts by weight of the surface active agent is present per 100 parts by weight of plant growth regulant composition.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylinic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

The wettable powders compositions of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed coverage is very uniform.

Dusts are dense finely-divided particulate compositions which are intended for application to the soil in dry form. Dusts are characterized by their free-flowing and rapid settling properties so that they are not readily wind-borne to areas where they are of no value. Dusts contain primarily an active ingredient and a dense, free-flowing finely-divided particulate extender. However, their performance is sometimes aided by the inclusion of a wetting agent such as those listed hereinbefore under wettable powder compositions and convenience in manufacture frequently demands the inclusion of an inert, absorptive grinding aid. Suitable classes of grinding aids are natural clays, diatomaceous earth and synthetic minerals derived from silica or silicate. Preferred grinding aids include attapulgite clay, diatomaceous silica, synthetic fine silica and synthetic calcium and magnesium silicates.

The inert finely-divided solid extender for the dusts can be either of vegetable or mineral origin. The solid extenders are characterized by possessing relatively low surface areas and are poor in liquid absorption. Suitable inert solid extenders for plant growth regulant dusts include micaceous talcs, pyrophyllite, dense kaolin clays, ground calcium phosphate rock and tobacco dust. The dusts usually contain from about 0.5 to 95 parts active ingredient, 0 to 50 parts grinding aid, 0 to 50 parts wetting agent and 5 to 99.5 parts dense solid extender, all parts being by weight and based on the total weight of the dust.

The wettable powders described above may also be used in the preparation of dusts. While such wettable powders could be used directly in dust form, it is more advantageous to dilute them by blending with the dense dust diluent. In this manner, dispersing agents, corrosion inhibitors, and anti-foam agents may also be found as components of a dust.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. Suitable surface active agents are anionic, cationic and non-ionic such as alkyl aryl polyethoxy alcohols, polyethylene sorbitol or sorbitan fatty acid esters, polyethylene glycol fatty esters, fatty alkylol amide condensates, amine salts of fatty alcohol sulfates together with long chain alcohols and oil soluble petroleum sulfonates or mixtures thereof. The emulsifiable oil compositions generally contain from about 5 to 95 parts active ingredient, about 1 to 50 parts surface active agent and about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore under wettable powders can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely-divided clays such as kaolin clays, hydrated attapulgite or bentonitic clays. These extenders are sprayed or blended with the active ingredient to form the phytotoxic granules.

The mineral particles which are used in the granular plant growth regulant compositions of this invention usually have a size range of 10 to 100 mesh, but preferably such that a large majority of the particles have from 14 to 60 mesh with the optimum size being from 20 to 40 mesh. Clay having substantially all particles between 14 and 80 mesh and at least about 80 percent between 20 and 40 mesh is particularly preferred for use in the present granular composition. The term "mesh" as used herein means U.S. Sieve Series.

The granular plant growth regulant compositions of this invention generally contain from about 5 parts to about 30 parts by weight of active ingredient per 100 parts by weight of clay and 0 to about 5 parts by weight of surface active agent per 100 parts by weight of particulate clay. The preferred plant growth regulant granular compositions contain from about 10 parts to about 25 parts by weight of active ingredient per 100 parts by weight of clay.

The plant growth regulant compositions of this invention can also contain other additaments, for example fertilizers, phytotoxicants, other plant growth regulants, pesticides and the like used as adjuvant or in combination with any of the abovedescribed adjuvants. Chemicals useful in combination with the active ingredients of this invention include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
   3-amino-1,2,4-triazole
   2-methoxy-4-ethylamino-6-isopropylamino-s-triazine
   2-chloro-4-ethylamino-6-isopropylamino-s-triazine
   2-chloro-N,N-diallylacetamide
   2-chloroallyl diethyldithiocarbamate
   N'-(4-chlorophenoxy) phenyl-N,N-dimethylurea
   isopropyl M-(3-chlorophenyl)carbamate
   2,2-dichloropropionic acid
   S-2,3-dichloroallyl N,N-diisopropylthiolcarbamate
   2-methoxy-3,6-dichlorobenzoic acid
   2,6-dichlorobenzonitrile
   6,7-dihydrodipyrido(1,2-a:2',1'-c)-pyrazidiinium salt
   3-(3,4-dichlorophenyl)-1,1-dimethylurea
   4,6-dinitro-o-sec-butylphenol
   2-methyl-4,6-dinitrophenol
   ethyl N,N-dipropylthiolcarbamate
   2,3,6-trichlorophenylacetic acid
   5-bromo-3-isopropyl-6-methyluracil
   3-(3,4-dichlorophenyl)-1-methoxy-1-methylurea
   2-methyl-4-chlorophenoxyacetic acid
   3-(p-chlorophenyl)-1,1-dimethylurea
   1-butyl-3-(3,4-dichlorophenyl)-1-methylurea
   N-1-naphthylphthalamic acid
   1,1'-dimethyl-4,4'-bipyridinium salt
   2-chloro-4,6-bis(isopropylamino)-s-triazine
   2-chloro-4,6-bis(ethylamino)-s-triazine
   2,4-dichlorophenyl-4-nitrophenyl ether
   alpha, alpha, alpha-trifluoro-2,6-dinitro-N,N-dipropyl-p-toluidine
   S-propyl dipropylthiolcarbamate
   2,4-dichlorophenoxyacetic acid
   2',6'-diethyl-N-methoxymethyl-2-chloroacetanilide Fertilizers useful in combination with the active ingredients include for example ammonium nitrate, urea, potash, and superphosphate. Other useful additaments include materials in which plant organisms take root and grow such as compost, manure, humus, sand and the like.

When operating in accordance with the present invention, effective amounts of the active ingredient are dispersed in or on soil or plant growth media and/or applied to above-ground portions of plants, or are incorporated into aquatic media in any convenient fashion. Application to the soil or growth media can be carried out by simply admixing with the soil, by applying to the surface of the soil and thereafter dragging or discing into the soil to the desired depth, or by employing a liquid carrier to accomplish the penetration and impregnation. The application of liquid and particulate solid plant growth regulant compositions to the surface of soil or to above-ground portions of plants can be carried out by conventional methods, e.g. power dusters, boom and hand sprayers and spray dusters. The compositions can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the plant growth regulants. The application of plant growth regulant compositions to aquatic plants is usually carried out by adding the compositions to the aquatic media in the area where control of the aquatic plants is desired.

The application of an effective amount of the 3'-(carbamoyloxy)anilides of this invention to the soil or growth media and/or plant is essential and critical for the practice of one embodiment of the present invention. The exact amount of active ingredient to be employed is dependent upon the response desired in the plant as well as such other factors as the plant species and stage of development thereof, the specific soil and depth at which the active ingredients are distributed in the soil and the amount of rainfall as well as the specific active ingredient employed. In foliar treatment for the modification of vegetative growth, the active ingredients are applied in amounts from about 1 to about 50 or more pounds per acre. In applications to soil for the modification of the growth of germinant seeds, germinative seeds, emerging seedlings and established vegetation, the active ingredients are applied in amounts from about 0.001 to about 25 or more pounds per acre. In such soil applications, it is desirable that the active ingredients be distributed to a depth of at least 0.2 inches. In selective pre-emergence phytotoxic applications the active ingredients are usually applied in amounts from about 0.1 to 20 pounds per acre. In applications for increasing the maturation rate of plants including increasing the sugar content of plants, e.g. sugar cane, and facilitating the defoliation of plants, e.g. cotton and soybeans, the active ingredients are applied in amounts of at least 0.1 pound per acre. In applications for stimulating the growth of plants to obtain improved yield of plant products, the active ingredients are applied in amounts of at least 0.1 pounds per acre. In applications for the control of aquatic plants, the active ingredients are applied in amounts from about 0.01 parts per million to about 1000 parts per million, based on the aquatic medium. Thus the effective amount for each response can be stated in terms of the response, e.g. a plant growth regulant amount for general modification, a phytotoxic amount for overall control or selective control, a tillering amount for tillering, an amount sufficient to increase the maturation rate for responses such as defoliation, increased sugar content and the like, and a desiccating amount for desiccation. It is believed that one skilled in the art can readily determine from the teachings of this specification, including examples, the approximate application rate for any situation.

The terms "soil" and "growth media" are employed in the present specification and claims in their broadest sense to be inclusive of all conventional soils as defined in Webster's New International Dictionary, Second Edition, Unabridged (1961). Thus, the terms refer to any substance or media in which vegetation may take root and grow, and are intended to include not only earth but also compost, manure, muck, humus, sand and the like, adapted to support plant growth.

Although the invention is described with respect to specific modifications, the details thereof are not to be construed as limitations except to the extent indicated in the following claims.

We claim:
1. A compound of the formula

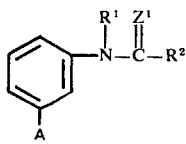

wherein
- $Z^1$ is selected from the group consisting of oxygen and sulfur;
- $R^1$ is selected from the group consisting of:
  I. Hydrogen,
  II. $R^3 - (B)_n$ - wherein B is selected from the group consisting of carbonyl and oxygen; $R^3$ is selected from the group consisting of alkyl having a maximum of 12 carbon atoms; alkenyl having a maximum of 7 carbon atoms and alkynyl having at least 3 and a maximum of 6 carbon atoms; and $n$ is an integer from 0 to 1; and
  III. $R^6O - (R^5O)_m - R^4$ - wherein $R^4$ is alkylene of not more than 4 carbon atoms; $R^5$ is alkylene of not more than 4 carbon atoms; $R^6$ is selected from the group consisting of alkyl and alkenyl of not more than 6 carbon atoms; and $m$ is an integer from 0 to 1;
- $R^2$ is selected from the group consisting of
  I. hydrogen,
  II. hydrocarbyl selected from the group consisting of alkyl having a maximum of 12 carbon atoms, alkenyl having a maximum of 8 carbon atoms, alkynyl having a maximum of 6 carbon atoms and haloalkyl having a maximum of 6 carbon atoms, and a maximum of 3 halogen atoms;
  III. $R^6O - (R^5O)_m - R^4$ - wherein $R^4$, $R^5$, $R^6$ and $m$ are as previously defined,
  IV. cycloalkyl and alkylcycloalkyl having 3 to 7 ring carbon atoms and a maximum of 4 chain carbon atoms;
  V. phenyl and substituted phenyl having a maximum of two substituents said substituent being selected from the group consisting of halogen, and alkyl having a maximum of 4 carbon atoms; and
  VI. aralkyl of the formula

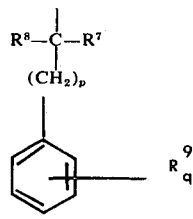

wherein
$R^7$ is selected from the group consisting of hydrogen, alkyl having a maximum of 4 carbon atoms, alkenyl having a maximum of 3 carbon atoms and haloalkyl having a maximum of 4 carbon atoms and a maximum of 3 halogen atoms; $R^8$ is selected from the group consisting of hydrogen, alkyl having a maximum of 4 carbon atoms and haloalkyl having a maximum of 4 carbon atoms and a maximum of 3 halogen atoms; $R^9$ is independently selected from the group consisting of alkyl having a maximum of 4 carbon atoms, alkoxy having a maximum of 2 carbon atoms, and halogen; $p$ is one of the integers 0 to 2; and $q$ is one of the integers 0 to 2; and A is

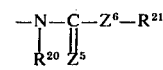

wherein
$Z^5$ and $Z^6$ are oxygen;
$R^{20}$ is selected from the group consisting of hydrogen, alkyl having a maximum of 6 carbon atoms and alkenyl having a maximum of 6 carbon atoms; and
$R^{21}$ is selected from the group consisting of alkyl having a maximum of 8 carbon atoms, alkenyl having a maximum of 6 carbon atoms, cycloalkyl having from 3 to 7 ring carbon atoms; cyclohexenyl, phenyl, substituted phenyl having a maximum of two substituents said substituents being selected from the group consisting of halogen, nitro and alkyl having a maximum of 4 carbon atoms, the group

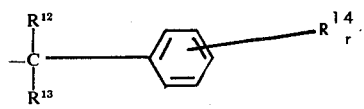

and the group

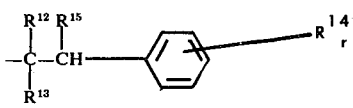

wherein
$R^{12}$ and $R^{13}$ are each independently selected from the group consisting of hydrogen, alkyl having a maximum of 4 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, provided that only one of $R^{12}$ and $R^{13}$ can be alkenyl or chloroalkenyl; $R^{14}$ is selected from the group consisting of halogen, alkyl having a maximum of 4 carbon atoms, nitro, alkoxy having a maximum of 3 carbon atoms, $R^{15}$ is selected from the group consisting of alkyl and alkenyl each having a maximum of 4 carbon atoms, provided that $R^{15}$ is other than alkenyl where either $R^{12}$ or $R^{13}$ is alkenyl, and $r$ is one of the integers 0 to 2.

2. A compound in accordance with claim 1 wherein $R^1$ is selected from the group consisting of hydrogen, alkoxy having a maximum of 6 carbon atoms, alkyl having a maximum of 6 carbon atoms and alkenyl having a maximum of 6 carbon atoms; $R^2$ is selected from the group consisting of alkyl having a maximum of 12 carbon atoms, alkenyl having a maximum of 10 carbon atoms, haloalkyl having a maximum of 6 carbon atoms and a maximum of 4 chlorine atoms, cycloalkyl having 3 to 7 ring carbon atoms and a maximum of 4 chain carbon atoms, phenyl, substituted phenyl having a maximum of two substituents, said substituent being selected from the group consisting of halogen, alkyl having a maximum of 4 carbon atoms and the group

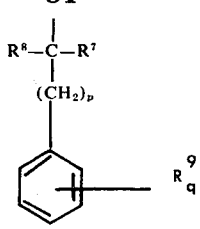

wherein
R$^7$ is selected from the group consisting of hydrogen, alkyl having a maximum of 4 carbon atoms, alkenyl having a maximum of 3 carbon atoms, and haloalkyl having a maximum of 4 carbon atoms and a maximum of 3 halogen atoms; R$^8$ is selected from the group consisting of hydrogen, alkyl having a maximum of 4 carbon atoms and haloalkyl having a maximum of 4 carbon atoms and a maximum of 3 halogen atoms; R$^9$ is independently selected from the group consisting of alkyl having a maximum of 4 carbon atoms, alkoxy having a maximum of 2 carbon atoms, and halogen; $p$ is one of the integers 0 to 2.

3. A compound in accordance with claim 2 which is methyl m-(2,2-dimethyl-3,3-dichloropropionamido)-carbanilate.

4. A compound in accordance with claim 2 which is methyl m-(2,2-dimethylvaleramido)carbanilate.

5. A phytotoxic composition having a phytotoxically effective amount of a compound of claim 1.

6. A phytotoxic method which comprises contacting a plant with a phytotoxic effective amount of a compound of claim 1.

* * * * *